US011267867B2

(12) United States Patent
Botten et al.

(10) Patent No.: US 11,267,867 B2
(45) Date of Patent: Mar. 8, 2022

(54) METHODS AND COMPOSITIONS FOR REDUCING INFECTIVITY OF VIRUS PARTICLES COMPRISING AN ERGIC-53 POLYPEPTIDE

(71) Applicant: University of Vermont and State Agricultural College, Burlington, VT (US)

(72) Inventors: Jason Botten, Burlington, VT (US); Joseph Klaus, Burlington, VT (US); Anne Mason, Burlington, VT (US)

(73) Assignee: University of Vermont and State Agricultural College, Burlington, VT (US)

( * ) Notice: Subject to any disclaimer, the term of this patent is extended or adjusted under 35 U.S.C. 154(b) by 0 days.

(21) Appl. No.: 16/093,520

(22) PCT Filed: Apr. 13, 2017

(86) PCT No.: PCT/US2017/027435
§ 371 (c)(1),
(2) Date: Oct. 12, 2018

(87) PCT Pub. No.: WO2017/180884
PCT Pub. Date: Oct. 19, 2017

(65) Prior Publication Data
US 2019/0127441 A1    May 2, 2019

Related U.S. Application Data

(60) Provisional application No. 62/321,928, filed on Apr. 13, 2016.

(51) Int. Cl.
*C07K 14/745*   (2006.01)
*C07K 14/47*    (2006.01)
*A61K 38/16*    (2006.01)
*A61K 38/17*    (2006.01)
*A61K 38/36*    (2006.01)
*A61P 31/14*    (2006.01)
*C07K 16/18*    (2006.01)
*C07K 16/36*    (2006.01)
*C07K 1/18*     (2006.01)
*C07K 1/36*     (2006.01)

(52) U.S. Cl.
CPC ............ *C07K 14/745* (2013.01); *A61K 38/16* (2013.01); *A61K 38/1709* (2013.01); *A61K 38/36* (2013.01); *A61P 31/14* (2018.01); *C07K 14/47* (2013.01); *C07K 16/18* (2013.01); *C07K 16/36* (2013.01)

(58) Field of Classification Search
None
See application file for complete search history.

(56) References Cited

U.S. PATENT DOCUMENTS

2004/0259157 A1   12/2004   Ginsburg et al.
2005/0260195 A1   11/2005   Dagan et al.

OTHER PUBLICATIONS

Cornillez-Ty et al., "Severe Acute Respiratory Syndrome Coronavirus Nonstructural Protein 2 Interacts with a Host Protein Complex Involved in Mitochondrial Biogenesis and Intracellular Signaling." Journal of Virology, vol. 83, No. 19, Oct. 2009, 10314-10318.
Hauri et al., "ERGIC-53 and traffic in the secretory pathway." Jouranl of Cell Science 113, 587-596 (2000).
International Preliminary Report on Patentability dated Oct. 16, 2018 from corresponding PCT/US2017/027435.
International Search Report dated Jul. 14, 2017 from corresponding PCT/US2017/027435.
Klaus et al., "The Intracellular Cargo Receptor ERGIC-53 is Required for the Production of Infectious Arenavirus, Coronavirus, and Filovirus Particles." Cell Host & Microbe 14, 522-534, Nov. 13, 2013.
Klaus J., "Determining the role of the ERGIC-53 cargo receptor complex in arenavirus propogation." Thesis, The University of Vermont, Oct. 2014: 175-219.
Lawson et al., "Recombinant vesicular stomatitis viruses from DNA." Proc. Natl. Acad. Sci. USA 92 (1995), 4477-4481.
Nishio et al., "Structural basis for the cooperative interplay between the two causative gene products of combind factor V and factor VIII deficiency." PNAS, Mar. 2, 2010, vol. 107., No. 9: 4034-4039.
Nyfeler et al., "Cargo Selectivity of the ERGIC-53/MCFD2 Transport Receptor Complex." Traffic 2006; 7: 1473-1481.
Written Opinion of the International Searching Authority dated Jul. 14, 2017 from corresponding PCT/US2017/027435.
Zhang et al. "Bleeding due to disruption of a cargo-specific ER-to-Golgi transport complex." Nature Genetics 34, 220-225 (2003).
Zhang et al. "Genotype-phenotype correlation in combined deficiency of factor V and factor VIII." Blood, Jun. 15, 2008, vol. 111, No. 12: 5592-5600.
Zheng et al., "EF-hand domains of MCFD2 mediate interactions with both LMAN1 and coagulation factor V or VIII." Blood, Feb. 4, 2010, vol. 115, No. 5: 1081-1087.
Zheng et al., "Molecular basis of LMAN1 in coordinating LMAN1-MCFD2 cargo receptor formation and ER-to-Golgi transport of FV/FVIII." Blood, 2010, vol. 116, No. 25: 5698-5706.

(Continued)

*Primary Examiner* — Nicole Kinsey White
(74) *Attorney, Agent, or Firm* — Pierce Atwood LLP

(57) ABSTRACT

The invention relates, in part, to compounds, compositions, and methods to reduce infectivity of virus particles and to treat viral infections in subjects.

9 Claims, 14 Drawing Sheets
Specification includes a Sequence Listing.

(56) References Cited

OTHER PUBLICATIONS

Zheng et al., "Structural Characterization of Carbohydrate Binding by LMAN1 Protein Provides New Insight into the Endoplasmic Reticulum Export of Factors V (FV) and VIII (FVIII)." Journal of Biological Chemistry vol. 288, No. 28 (2013), 20499-20509.
Yee, Carol M.Y, et al. "Selection of human antibody fragments by phage display" Nature Protocols vol. 2 No. 11 (2007) 3001-3008.

Legend:
- Empty Vector
- ERGIC-53 ΔCRD  * p = 0.0002
- MCFD2           * p < .0001
- ERGIC-53 WT     * p = .0011

Y-axis: Relative JUNV PFU
X-axis: 48 Hours post-infection

GPC binding zone

Mannose binding

MCFD2 binding motif

Lumen

FIG. 7

SEQUENCE LISTING

```
<160> NUMBER OF SEQ ID NOS: 16

<210> SEQ ID NO 1
<211> LENGTH: 146
<212> TYPE: PRT
<213> ORGANISM: Homo sapiens

<400> SEQUENCE: 1

Met Thr Met Arg Ser Leu Leu Arg Thr Pro Phe Leu Cys Gly Leu Leu
1               5                   10                  15

Trp Ala Phe Cys Ala Pro Gly Ala Arg Ala Glu Glu Pro Ala Ala Ser
                20                  25                  30

Phe Ser Gln Pro Gly Ser Met Gly Leu Asp Lys Asn Thr Val His Asp
            35                  40                  45

Gln Glu His Ile Met Glu His Leu Glu Gly Val Ile Asn Lys Pro Glu
        50                  55                  60

Ala Glu Met Ser Pro Gln Glu Leu Gln Leu His Tyr Phe Lys Met His
65                  70                  75                  80

Asp Tyr Asp Gly Asn Asn Leu Leu Asp Gly Leu Glu Leu Ser Thr Ala
                85                  90                  95

Ile Thr His Val His Lys Glu Glu Gly Ser Glu Gln Ala Pro Leu Met
            100                 105                 110

Ser Glu Asp Glu Leu Ile Asn Ile Ile Asp Gly Val Leu Arg Asp Asp
        115                 120                 125

Asp Lys Asn Asn Asp Gly Tyr Ile Asp Tyr Ala Glu Phe Ala Lys Ser
    130                 135                 140

Leu Gln
145

<210> SEQ ID NO 2
<211> LENGTH: 4115
<212> TYPE: DNA
<213> ORGANISM: Homo sapiens

<400> SEQUENCE: 2
gaagccgagg aagagcgttt tggggacggg ggctggtgag gctcacgttg gagggcttcg      60
cgtctgcttc ggagaccgta aggatattga tgaccatgag atccctgctc agaaccccct     120
tcctgtgtgg cctgctctgg gccttttgtg ccccaggcgc cagggctgag gagcctgcag     180
ccagcttctc ccaacccggc agcatgggcc tggataagaa cacagtgcac gaccaagagc     240
atatcatgga gcatctagaa ggtgtcatca acaaaccaga ggcggagatg tcgccacaag     300
aattgcagct ccattacttc aaaatgcatg attatgatgg caataatttg cttgatggct     360
tagaactctc cacagccatc actcatgtcc ataaggagga agggagtgaa caggcaccac     420
taatgagtga agatgaactg attaacataa tagatggtgt tttgagagat gatgacaaga     480
acaatgatgg atacattgac tatgctgaat ttgcaaaatc actgcagtag atgttatttg     540
gccatctcct ggttatatac aaatgtgacc cgtgataatg tgattgaaca ctttagtaat     600
```

```
gcaaaataac tcatttccaa ctactgctgc agcattttgg taaaaacctg tagcgattcg    660
ttacactggg gtgagaagag ataagagaaa tgaaagagaa gagaaatggg acatctaata    720
gtccctaagt gctattaaat accttattgg acaagggctt gcttcaagca tctgtattag    780
tctgtattaa tgctgctgat aaagacgtac ccgagactgg gaagaaaaag aggtttactt    840
ggacttacag ttccacatgg ctggggaggc ctcagaatca tggcgggagg tgaaaggcac    900 ttcttcatg gcagcaagag aaaatgagga agaagcaaaa gtggaaaccc ctgataagcc    960
atcagatctt gtgaaactta ttcactatca caagaatagc atgggaaaga ctggccccca   1020
tgattcaatt acctcccctt gggtctctcc cacaacacgt gggaattctg gtagatacaa   1080
tttcaagttg agatttgggt ggggacatag ccaaaccata tcattctacc cctggcccct   1140
ccaaatctca tgtcctcact attcaaaacc aatcatgcct tcctaacagt cccccaaagt   1200
cttaactctt ttcagcatta acgcaaaaat ccacagtcca aagtctcatc tgagacaagg   1260
caagtccctt ccacctatga gcctgtaaaa tcaaaagcaa gctagttact tcctagatac   1320
caacaggggt acaggtattg attaaagacg gctgttccaa atgggagaaa ttggccaaaa   1380
taaaggggtt acagggccca tgcaagtccg aaatccagca gggctgtcaa attttaaagt   1440
tccagaataa tctcctttga ctccaggtct cacatccagg tcatactgat gcaagaagtg   1500
ggttcccatg gtcttgggca gctctgcccc tgtggctttg tagggtacag cctccctcct   1560
ggctgctttc acggctgttg ttcagtgcct gcggcttttc caggtgcacg gtgcaagctg   1620
ttggtggatc taccattctg gggtctggag gacggtggcc ctcttctcac agctccacta   1680
ggcagtgccc cagtagggac tctgtgtggg ggctcccaca ccacatttcc cttctgcact   1740
gccctagcag aggttctctc ccctgccgct gagagggcct ctcccctgca gcaaacgttt   1800
gcctgggcat tgaggcattt ccatacatct tctgaaaact aggcggaggt ttccaaatct   1860
caattcttga cttctgtgca cctgcaggct taacagcaca tagaagctgc caaggcttgg   1920
ggcttccact ctgaagccac agcccgagct gtatgttggc ccctttcagc catggctgga   1980
gtggctggga cacaagacac caagtcccta ggctgcacac acatgtcagg ggctgccctg   2040
acatggcctg gagacatttt ccccatggtg ttggggatta acattaggct ccttgctact   2100
tatgcaaatt tctgcagctg gcttgaattt ctccccagaa aatgggtttt tcttttctat   2160
tgcatagtca ggctgcaaat ttccaaactt ttatgctttg cttcccttat ttataaggga   2220
atgcctttaa aagcacccaa gtcacctgtt gaacactttg ctgcttagaa atttcttccg   2280
ctagttaacc taaatcatct ctctcaagtt caaagttcca caaatcccta tggaaggggc   2340
aaaatgctgc cagtctcttt gctaaaacat aacaagagtc acctttactc cagttcccaa   2400
caagttcctc atcttcatct gaggccacct cagcctggac tttgttgtcc atattgctat   2460
cagcatttgg ggcaaagcca ttcaacaagt ctgtaggaag ttccaaactt tcccacattt   2520
tcctgttttc ttctgagccc tccaaactgt tccagcctct gcctgttacc cagttccaaa   2580
gtcacttcca catttgggt atttcttcag caggtcccaa tctactggta ccaatttact   2640
gtattagtcc gttttcacgc tgctgataaa gacatacccg agactgggaa gaaaaagtgg   2700
tttaattgga cttaaagttc cacatggctg gggaggcctc agaatcatgg tgggaggcaa   2760 aagcacttc ttacattgtg gcaagaaaaa atgaggaaga agcaaaagca gaaacccctg   2820
ataaactgat cagatctcat gagacttatt cactgtcacg agaatagcac gggaaagact   2880
ggcccccatg attcaattac ctccccctgg gtctgtccca caacgtgg gaattctggg   2940 agatacaatt caagttgaga tttgtggggg gacacaacca aaccatatca gcatcctttc   3000
```

-continued

```
aagaatatta gataattgga gctgagtact caggaacttg actgtagtag aatactgcta    3060
gtttcttaat tttaattcac atcacctgaa agtaaaaca acaggctttg ccaagtggat    3120
gcttttcagt aacagtgaag tggagtgaat accaaatgtt tgccctggtg gttcctatct    3180
cttcaggcaa acatggtcag tattctgtaa agttcccctg cctaaatga ttacttgctc    3240 tgggcaagtg gatatttatt aggctatttc aaagccacag cataagaatg tcagcctagc    3300
cacagagtct gagattctga gttcagccta gccacagagt ctaagattct gtatcctctg    3360
acattttgga aatgatacac tactggctta agtgatgact ctttcagatt ttcagtattt    3420
tatacaacta ctgccacatc cttatacttt attgcttttc tgtcttcttc aacctgggag    3480
agaccctgaa tttgagtgtg ttctctaatc aatagtggtt tagctttctt ttctatttca    3540
ctcgtttcta gggttttta tttgcagttt aggaactatt aggaatgtca ggactttatc    3600 agcagggta aaactaccac ctggcctagc ctaagtagga agtgaaaaga taattcacca    3660
aacaatgatt aatcagatag aagttctagt caagagggga attgttgaag ttacctcttt    3720
tagcctagat acatggattc ttttcaaatc aggaaagatt agaaaaggaa cccaaaaaac    3780
cctttaacag tgtgaatctt tatagtattt gaaaatgaga agaagcagca gattgtaatt    3840
tggtttattg gatgtgatgg acgttctgta atagaaaacc tgaaacgatg attgaatggg    3900
aaaaagagac tacaaaattt gtcgtaggat gtatacagac ttattttctt tattacagta    3960
ttataagaaa acatatgtat ttgtaaaaat ggtttcctgt gtcaagtatt tgtgcagtca    4020
gagctgactt gtaaactatt cttgtaatag ctcattattt tgaaagattt atatatgatg    4080
aattctggat atatgaccaa taaaactgat gaagc                              4115
```

<210> SEQ ID NO 3
<211> LENGTH: 510
<212> TYPE: PRT
<213> ORGANISM: Homo sapiens

<400> SEQUENCE: 3

```
Met Ala Gly Ser Arg Gln Arg Gly Leu Arg Ala Arg Val Arg Pro Leu
1               5                   10                  15

Phe Cys Ala Leu Leu Ser Leu Gly Arg Phe Val Arg Gly Asp Gly
            20                  25                  30

Val Gly Gly Asp Pro Ala Val Ala Leu Pro His Arg Arg Phe Glu Tyr
        35                  40                  45

Lys Tyr Ser Phe Lys Gly Pro His Leu Val Gln Ser Asp Gly Thr Val
    50                  55                  60

Pro Phe Trp Ala His Ala Gly Asn Ala Ile Pro Ser Ser Asp Gln Ile
65                  70                  75                  80

Arg Val Ala Pro Ser Leu Lys Ser Gln Arg Gly Ser Val Trp Thr Lys
                85                  90                  95

Thr Lys Ala Ala Phe Glu Asn Trp Glu Val Glu Val Thr Phe Arg Val
            100                 105                 110

Thr Gly Arg Gly Arg Ile Gly Ala Asp Gly Leu Ala Ile Trp Tyr Ala
        115                 120                 125

Glu Asn Gln Gly Leu Glu Gly Pro Val Phe Gly Ser Ala Asp Leu Trp
    130                 135                 140

Asn Gly Val Gly Ile Phe Phe Asp Ser Phe Asp Asn Asp Gly Lys Lys
145                 150                 155                 160

Asn Asn Pro Ala Ile Val Ile Gly Asn Asn Gly Gln Ile His Tyr
                165                 170                 175
```

Asp His Gln Asn Asp Gly Ala Ser Gln Ala Leu Ala Ser Cys Gln Arg
            180                 185                 190

Asp Phe Arg Asn Lys Pro Tyr Pro Val Arg Ala Lys Ile Thr Tyr Tyr
        195                 200                 205

Gln Asn Thr Leu Thr Val Met Ile Asn Asn Gly Phe Thr Pro Asp Lys
    210                 215                 220

Asn Asp Tyr Glu Phe Cys Ala Lys Val Glu Asn Met Ile Ile Pro Ala
225                 230                 235                 240

Gln Gly His Phe Gly Ile Ser Ala Ala Thr Gly Gly Leu Ala Asp Asp
                245                 250                 255

His Asp Val Leu Ser Phe Leu Thr Phe Gln Leu Thr Glu Pro Gly Lys
            260                 265                 270

Glu Pro Pro Thr Pro Asp Lys Glu Ile Ser Glu Lys Glu Lys Glu Lys
        275                 280                 285

Tyr Gln Glu Glu Phe Glu His Phe Gln Gln Glu Leu Asp Lys Lys Lys
    290                 295                 300

Glu Glu Phe Gln Lys Gly His Pro Asp Leu Gln Gly Gln Pro Ala Glu
305                 310                 315                 320

Glu Ile Phe Glu Ser Val Gly Asp Arg Glu Leu Arg Gln Val Phe Glu
                325                 330                 335

Gly Gln Asn Arg Ile His Leu Glu Ile Lys Gln Leu Asn Arg Gln Leu
            340                 345                 350

Asp Met Ile Leu Asp Glu Gln Arg Arg Tyr Val Ser Ser Leu Thr Glu
        355                 360                 365

Glu Ile Ser Lys Arg Gly Ala Gly Met Pro Gly Gln His Gly Gln Ile
    370                 375                 380

Thr Gln Gln Glu Leu Asp Thr Val Val Lys Thr Gln His Glu Ile Leu
385                 390                 395                 400

Arg Gln Val Asn Glu Met Lys Asn Ser Met Ser Glu Thr Val Arg Leu
                405                 410                 415

Val Ser Gly Met Gln His Pro Gly Ser Ala Gly Gly Val Tyr Glu Thr
            420                 425                 430

Thr Gln His Phe Ile Asp Ile Lys Glu His Leu His Ile Val Lys Arg
        435                 440                 445

Asp Ile Asp Asn Leu Val Gln Arg Asn Met Pro Ser Asn Glu Lys Pro
    450                 455                 460

Lys Cys Pro Glu Leu Pro Pro Phe Pro Ser Cys Leu Ser Thr Val His
465                 470                 475                 480

Phe Ile Ile Phe Val Val Gln Thr Val Leu Phe Ile Gly Tyr Ile
                485                 490                 495

Met Tyr Arg Ser Gln Gln Glu Ala Ala Ala Lys Lys Phe Phe
            500                 505                 510

<210> SEQ ID NO 4
<211> LENGTH: 4848
<212> TYPE: DNA
<213> ORGANISM: Homo sapiens

<400> SEQUENCE: 4
ctcccgccct cctccgcgtt ccagaatcca agatggcggg atccaggcaa agggtctcc      60 gggccagagt tcggccgctg ttctgcgcct tgctgctgtc actcggtcgc ttcgtccggg     120
gcgacggcgt gggaggagac cccgcggtcg cgttgccaca tcgccgtttc gagtacaaat     180
acagcttcaa ggggccgcac ctggtgcaga gcgacgggac cgtgcccttc tgggcccacg     240

```
cggggaatgc tattccaagt tcagatcaaa ttcgagtagc accatcttta aaaagccaaa    300
gaggctcagt gtggacaaag acaaaagcgg cctttgagaa ctgggaagtt gaggtgacat    360
ttcgagtgac tggaagaggt cgaattggag ctgatggcct agcaatttgg tatgcagaaa    420
atcaaggctt ggagggccct gtgtttggat cagctgatct gtggaatggt gttggaatat    480 ttttttgattc ttttgacaat gatggaaaga aaataatcc tgctatagta attataggca    540
acaatggaca aatccattat gaccatcaaa atgacgggc tagtcaagct ttggcaagtt    600
gccagaggga cttccgcaac aaaccctatc ctgtccgagc aaagattacc tattaccaga    660
acacactgac agtaatgatc aataatggct ttacaccaga taaaaatgat tatgaatttt    720
gtgccaaagt ggaaaatatg attatccctg cacaagggca ttttggaata tctgctgcaa    780
ctggaggtct tgcagatgac catgatgtcc tttcttttct gactttccag ttgactgaac    840
ctggaaaaga gccgcccaca ccagataaag aaatttcgga aaggaaaaa gaaaagtatc    900 aggaggaatt tgagcacttt caacaagaat tggataaaaa aaagaggaa ttccagaagg    960 gccaccccga cctccaaggg cagcctgcgg aggaaatatt tgagagtgta ggagatcgag   1020
agctaagaca agtctttgaa ggacagaatc gtattcatct tgaaatcaag cagctgaacc   1080
ggcagttaga tatgattctt gatgaacaga aagatatgt ctcttcctta acagaggaaa   1140
tctctaaaag aggagcagga atgcctgggc agcatgggca gattactcaa caagaactgg   1200
atactgttgt gaaaactcag catgagattc tgagacaagt aaatgaaatg aaaaattcca   1260
tgagtgaaac cgtcagactg gtcagtggaa tgcagcaccc tggctctgct ggaggcgtct   1320
atgagacaac acagcacttc attgacatca aagagcacct gcacatagta aagagggaca   1380
tagataactt agtgcagcga aatatgccat caaatgaaaa gccgaaatgc ccagaactac   1440
caccatttcc atcatgtttg tctacggtcc acttcattat atttgttgtg gtgcaaactg   1500
tattattcat tggttatatc atgtataggt ctcagcaaga agcagctgcc aaaaaattct   1560
tttgactacc attttcctgt gtacttcatc tatttgtgta caaaatgatg tcgttttgag   1620
ggaatttaag tatttaaatt gcttcatagt ctaaattatt aattttctta ataaaataac   1680
tgtttaaaca ttgatttgca gttaagaata aaccttaaag caaagacaac cacatttttaa   1740 tttgttcaca gtatgtaaat ctgtctaaat ttcagtgaat ttctggtcag tatgatgcag   1800
cctctgagca gaatattgac cagtaagagg gtaaataaag tggggcaac ccctggatat   1860 gaatgttacc ccctaagtct ccaatattgc aggtttccct gtataacgta aacacacttg   1920
ccctcatgcc tcccagaata tgaggtctaa ttaagaagtc ccatcaggtt tatttttgtaa   1980 ccaaagtctt ttttagaggt cagacttcct aatcaaaggc ctgggcctgc agtcctttca   2040
tcttaatgca acttcctttg aaatcaaaga atattttgtc tgagagcttt aaggatctgg   2100
taatagactt caaaatgtta agtgaaattt ttttttcctc tatttatcaa tgatatattt   2160 cactttttaaa ggaaattta gaggaaaatt aatagctgct ttttgcctaa aaaaccttgt   2220
gggtggaaac attcctctga gaatggcttt tataggtatt ttgcctggta atgtattcat   2280
tcatgattgc ccatattctt gaatgtcttc attccaatgg ggtcaggtca atattatgaa   2340
aataattttt atatttatat ttgtaactta aggaattat ttctcccttt actacagcat   2400
gtaaattcag ctcaaattgc atgatctgag gatttaaatt cacaaaacct gccactacat   2460
tctggtttac attagttact tcatgctggc tggggttagt gaccatttgc atactctttt   2520
aaatcaagga ggctgtagta gaagcagttt taagattctt gaaggcaaaa tttgaaaaac   2580
```

```
agtgaatact tctaattgtt tccttttagt gccagaacta aggacattgt gaagcacttg    2640
ttagtaaact taaccttgaa atgtcagact ggaaggagtt tttatagtct ttgtgcatac    2700
ttctaggtat tacagaaaca gtctgtaaat gacattttaa gatgcaaatt taattctgtt    2760
cacagctgat ttatactgat ttttgctgcc ttcaaaatac tcttttactt cttttagcta    2820
aaatggttgt ctttcatttg ccatagaatt ccaaacaata ctatcttata aaatagtact    2880
gttgaattat tccaagcctc cctaggtttg ctctcaaatg tcatttacag attgggctaa    2940
cgacctaaaa tctatatata aagactttct gaagaactct gtattatagc aataccaaac    3000
gagtgctgtg tgtgcaaaca gtctggcgtt gcttttatg ttgatattta tcctagaaca    3060
ctgaaagaga atatgccagt gataactcac tttacttcag tcatttcaac acagaaaatg    3120
cttctctagc attttttctt tgtagtgtta acattttgaa attcatgttt cagaggcttc    3180
atcatcacag aatttactct tgctccatga aaaaaaatta aataccttca gaggaatatt    3240
taagttgtaa actatgaaac ttgagaaatc ctcttgagat aaaaggctgc caaatccagt    3300
attataaagt ccatggtcat atgtgcctgt gcattaaagg aataccagat ctatgcagta    3360 tacattttc aggctgaaat tcaaggggaa tcattctgat tattcttact acaaatggag    3420
atggctatta tgaaacagca tgagcatgag ccttttatct tttatactta gtgatatact    3480
ttgcttgaaa atcactcagc aaagtagttc acatgatgtg tatcatattt gaagtgtggt    3540
ttttctcaaa atcattgact ttaaggagct catttctgaa caaaaggtt tgctctgtgg    3600 aaaaatcaat cactgccagg attctttcat ttctgtacta ttttgtataa ttgaatttgt    3660
tcacttctct cacaccagca agtgttttac aggtgccttg gattaaaaca aaattgattt    3720
taaaattttt atgtaagtca ttgtgtctat gatgccactt ttaaaaggaa aatgcaattg    3780
cgtaatggct tatatcctta tttaatgtac ctatttgtgt tctaataatt gtttgaatgt    3840
tttattcagc ttaaaacttt accatgaagt cataaacagt aaacaatgtt tgttatgta    3900 ttaagggggat atcagtgttt ctcaaagtat gatccatgga ccatctgggt catggcgcct    3960
ggtttcagac aacctgaatc aaatcttagg ggtggggctt tgggatgtca ttgttcaata    4020
ggcacctcag gagattctga gcacaccaat gtttgagaac cactaaaatg aggagtggga    4080 aaaaaaaat aggtgttttg ttaatttaga gctgagctga aagataata tattttttatt    4140 gtcaatgaca ttaacagata tgcactgatt cttttatacc tacaatttac ttaatgttcc    4200
ttttattaaa acgcgtggtt catgagcaac tacagactga atccagatta ttacctgttg    4260
ctttcagtat tttcgtgatg gcttttaatc ttatgaaatc atcttgagat cattcatggt    4320
caagccatga aaactcccat cttcaagcct gcctgctaaa gcttctttgc cttcctgatt    4380
gtgattatgg taacaattta tatcagacag ttgtactttt tgataactta gggaaaacag    4440
aaatgacttg aacaagggat tgcctgcctc actgcattgc agagatacaa tttttgtaaa    4500
gaacacaaat agcagttgtg aatattaagg tgtgattatc tttccctgtc catgtgctta    4560
ttgaaagaag atagtgaaca aatgattata ttgaggattt ttttaattta taagatctaa    4620
tgtgaaatcc acacttggaa cttttttagat ctgtctgttg cttgtttaat atatttctt    4680 tatgacatta cttaaagttt aaagggtttt tctatccact gtcaatttca attggataac    4740 atttttgtcaa gttttttttt tcctgattat ttgatgctag ctggaattca agaaatggca    4800 ttgacccttat tcaaataaag aaatattta gtaaaaaaaa aaaaaaaa    4848

<210> SEQ ID NO 5
<211> LENGTH: 143
```

```
<212> TYPE: PRT
<213> ORGANISM: Homo sapiens

<400> SEQUENCE: 5

Met Thr Met Arg Ser Leu Leu Arg Thr Pro Phe Leu Cys Gly Leu Leu
1               5                   10                  15

Trp Ala Phe Cys Ala Pro Gly Ala Arg Ala Glu Glu Pro Ala Ala Ser
            20                  25                  30

Phe Ser Gln Pro Gly Ser Met Gly Leu Asp Lys Asn Thr Val His Asp
        35                  40                  45

Gln Glu His Ile Met Glu His Leu Glu Gly Val Ile Asn Lys Pro Glu
    50                  55                  60

Ala Glu Met Ser Pro Gln Glu Leu Gln Leu His Tyr Phe Lys Met His
65                  70                  75                  80

Asp Tyr Asp Gly Asn Asn Leu Leu Asp Gly Leu Glu Leu Ser Thr Ala
                85                  90                  95

Ile Thr His Val His Lys Glu Glu Gly Ser Glu Gln Ala Pro Leu Met
            100                 105                 110

Ser Glu Asp Glu Leu Ile Asn Ile Ile Asp Gly Val Leu Arg Asp Asp
        115                 120                 125

Asp Lys Asn Asn Asp Gly Tyr Ile Asp Tyr Ala Glu Phe Ala Lys
    130                 135                 140

<210> SEQ ID NO 6
<211> LENGTH: 118
<212> TYPE: PRT
<213> ORGANISM: Homo sapiens

<400> SEQUENCE: 6

Pro Ala Ala Ser Phe Ser Gln Pro Gly Ser Met Gly Leu Asp Lys Asn
1               5                   10                  15

Thr Val His Asp Gln Glu His Ile Met Glu His Leu Glu Gly Val Ile
            20                  25                  30

Asn Lys Pro Glu Ala Glu Met Ser Pro Gln Glu Leu Gln Leu His Tyr
        35                  40                  45

Phe Lys Met His Asp Tyr Asp Gly Asn Asn Leu Leu Asp Gly Leu Glu
    50                  55                  60

Leu Ser Thr Ala Ile Thr His Val His Lys Glu Glu Gly Ser Glu Gln
65                  70                  75                  80

Ala Pro Leu Met Ser Glu Asp Glu Leu Ile Asn Ile Ile Asp Gly Val
                85                  90                  95

Leu Arg Asp Asp Asp Lys Asn Asn Asp Gly Tyr Ile Asp Tyr Ala Glu
            100                 105                 110

Phe Ala Lys Ser Leu Gln
        115

<210> SEQ ID NO 7
<211> LENGTH: 69
<212> TYPE: PRT
<213> ORGANISM: Homo sapiens

<400> SEQUENCE: 7

Lys Met His Asp Tyr Asp Gly Asn Asn Leu Leu Asp Gly Leu Glu Leu
1               5                   10                  15

Ser Thr Ala Ile Thr His Val His Lys Glu Glu Gly Ser Glu Gln Ala
            20                  25                  30

Pro Leu Met Ser Glu Asp Glu Leu Ile Asn Ile Ile Asp Gly Val Leu
```

```
                35                  40                  45
Arg Asp Asp Asp Lys Asn Asn Asp Gly Tyr Ile Asp Tyr Ala Glu Phe
         50                  55                  60

Ala Lys Ser Leu Gln
 65
```

<210> SEQ ID NO 8
<211> LENGTH: 51
<212> TYPE: PRT
<213> ORGANISM: Homo sapiens

<400> SEQUENCE: 8

```
Asn Asn Leu Leu Asp Gly Leu Glu Leu Ser Thr Ala Ile Thr His Val
 1               5                  10                  15

His Lys Glu Glu Gly Ser Glu Gln Ala Pro Leu Met Ser Glu Asp Glu
             20                  25                  30

Leu Ile Asn Ile Ile Asp Gly Val Leu Arg Asp Asp Asp Lys Asn Asn
         35                  40                  45

Asp Gly Tyr
     50
```

<210> SEQ ID NO 9
<211> LENGTH: 10
<212> TYPE: PRT
<213> ORGANISM: Homo sapiens

<400> SEQUENCE: 9

```
Gln Gln Glu Ala Ala Ala Lys Lys Phe Phe
 1               5                  10
```

<210> SEQ ID NO 10
<211> LENGTH: 33
<212> TYPE: PRT
<213> ORGANISM: Homo sapiens

<400> SEQUENCE: 10

```
Thr Val His Phe Ile Ile Phe Val Val Gln Thr Val Leu Phe Ile
 1               5                  10                  15

Gly Tyr Ile Met Tyr Arg Ser Gln Gln Glu Ala Ala Ala Lys Lys Phe
             20                  25                  30

Phe
```

<210> SEQ ID NO 11
<211> LENGTH: 477
<212> TYPE: PRT
<213> ORGANISM: Homo sapiens

<400> SEQUENCE: 11

```
Met Ala Gly Ser Arg Gln Arg Gly Leu Arg Ala Arg Val Arg Pro Leu
 1               5                  10                  15

Phe Cys Ala Leu Leu Leu Ser Leu Gly Arg Phe Val Arg Gly Asp Gly
             20                  25                  30

Val Gly Gly Asp Pro Ala Val Ala Leu Pro His Arg Arg Phe Glu Tyr
         35                  40                  45

Lys Tyr Ser Phe Lys Gly Pro His Leu Val Gln Ser Asp Gly Thr Val
     50                  55                  60

Pro Phe Trp Ala His Ala Gly Asn Ala Ile Pro Ser Ser Asp Gln Ile
 65                  70                  75                  80

Arg Val Ala Pro Ser Leu Lys Ser Gln Arg Gly Ser Val Trp Thr Lys
```

```
                    85                  90                  95
Thr Lys Ala Ala Phe Glu Asn Trp Glu Val Glu Val Thr Phe Arg Val
                100                 105                 110

Thr Gly Arg Gly Arg Ile Gly Ala Asp Gly Leu Ala Ile Trp Tyr Ala
            115                 120                 125

Glu Asn Gln Gly Leu Glu Gly Pro Val Phe Gly Ser Ala Asp Leu Trp
        130                 135                 140

Asn Gly Val Gly Ile Phe Phe Asp Ser Phe Asp Asn Asp Gly Lys Lys
145                 150                 155                 160

Asn Asn Pro Ala Ile Val Ile Gly Asn Asn Gly Gln Ile His Tyr
                165                 170                 175

Asp His Gln Asn Asp Gly Ala Ser Gln Ala Leu Ala Ser Cys Gln Arg
            180                 185                 190

Asp Phe Arg Asn Lys Pro Tyr Pro Val Arg Ala Lys Ile Thr Tyr Tyr
        195                 200                 205

Gln Asn Thr Leu Thr Val Met Ile Asn Asn Gly Phe Thr Pro Asp Lys
    210                 215                 220

Asn Asp Tyr Glu Phe Cys Ala Lys Val Glu Asn Met Ile Ile Pro Ala
225                 230                 235                 240

Gln Gly His Phe Gly Ile Ser Ala Ala Thr Gly Gly Leu Ala Asp Asp
                245                 250                 255

His Asp Val Leu Ser Phe Leu Thr Phe Gln Leu Thr Glu Pro Gly Lys
            260                 265                 270

Glu Pro Pro Thr Pro Asp Lys Glu Ile Ser Glu Lys Glu Lys Glu Lys
        275                 280                 285

Tyr Gln Glu Glu Phe Glu His Phe Gln Gln Glu Leu Asp Lys Lys Lys
    290                 295                 300

Glu Glu Phe Gln Lys Gly His Pro Asp Leu Gln Gly Gln Pro Ala Glu
305                 310                 315                 320

Glu Ile Phe Glu Ser Val Gly Asp Arg Glu Leu Arg Gln Val Phe Glu
                325                 330                 335

Gly Gln Asn Arg Ile His Leu Glu Ile Lys Gln Leu Asn Arg Gln Leu
            340                 345                 350

Asp Met Ile Leu Asp Glu Gln Arg Arg Tyr Val Ser Ser Leu Thr Glu
        355                 360                 365

Glu Ile Ser Lys Arg Gly Ala Gly Met Pro Gly Gln His Gly Gln Ile
    370                 375                 380

Thr Gln Gln Glu Leu Asp Thr Val Val Lys Thr Gln His Glu Ile Leu
385                 390                 395                 400

Arg Gln Val Asn Glu Met Lys Asn Ser Met Ser Glu Thr Val Arg Leu
                405                 410                 415

Val Ser Gly Met Gln His Pro Gly Ser Ala Gly Gly Val Tyr Glu Thr
            420                 425                 430

Thr Gln His Phe Ile Asp Ile Lys Glu His Leu His Ile Val Lys Arg
        435                 440                 445

Asp Ile Asp Asn Leu Val Gln Arg Asn Met Pro Ser Asn Glu Lys Pro
    450                 455                 460

Lys Cys Pro Glu Leu Pro Pro Phe Pro Ser Cys Leu Ser
465                 470                 475

<210> SEQ ID NO 12
<211> LENGTH: 225
<212> TYPE: PRT
<213> ORGANISM: Homo sapiens
```

<400> SEQUENCE: 12

```
Arg Arg Phe Glu Tyr Lys Tyr Ser Phe Lys Gly Pro His Leu Val Gln
1               5                   10                  15
Ser Asp Gly Thr Val Pro Phe Trp Ala His Ala Gly Asn Ala Ile Pro
            20                  25                  30
Ser Ser Asp Gln Ile Arg Val Ala Pro Ser Leu Lys Ser Gln Arg Gly
        35                  40                  45
Ser Val Trp Thr Lys Thr Lys Ala Ala Phe Glu Asn Trp Glu Val Glu
    50                  55                  60
Val Thr Phe Arg Val Thr Gly Arg Gly Arg Ile Gly Ala Asp Gly Leu
65                  70                  75                  80
Ala Ile Trp Tyr Ala Glu Asn Gln Gly Leu Glu Gly Pro Val Phe Gly
                85                  90                  95
Ser Ala Asp Leu Trp Asn Gly Val Gly Ile Phe Asp Ser Phe Asp
            100                 105                 110
Asn Asp Gly Lys Lys Asn Asn Pro Ala Ile Val Ile Gly Asn Asn
        115                 120                 125
Gly Gln Ile His Tyr Asp His Gln Asn Asp Gly Ala Ser Gln Ala Leu
    130                 135                 140
Ala Ser Cys Gln Arg Asp Phe Arg Asn Lys Pro Tyr Pro Val Arg Ala
145                 150                 155                 160
Lys Ile Thr Tyr Tyr Gln Asn Thr Leu Thr Val Met Ile Asn Asn Gly
                165                 170                 175
Phe Thr Pro Asp Lys Asn Asp Tyr Glu Phe Cys Ala Lys Val Glu Asn
            180                 185                 190
Met Ile Ile Pro Ala Gln Gly His Phe Gly Ile Ser Ala Ala Thr Gly
        195                 200                 205
Gly Leu Ala Asp Asp His Asp Val Leu Ser Phe Leu Thr Phe Gln Leu
    210                 215                 220
Thr
225
```

<210> SEQ ID NO 13
<211> LENGTH: 14
<212> TYPE: PRT
<213> ORGANISM: Homo sapiens

<400> SEQUENCE: 13

```
Glu Tyr Lys Tyr Ser Phe Lys Gly Pro His Leu Val Gln Ser
1               5                   10
```

<210> SEQ ID NO 14
<211> LENGTH: 36
<212> TYPE: PRT
<213> ORGANISM: Homo sapiens

<400> SEQUENCE: 14

```
Arg Arg Phe Glu Tyr Lys Tyr Ser Phe Lys Gly Pro His Leu Val Gln
1               5                   10                  15
Ser Asp Gly Thr Val Pro Phe Trp Ala His Ala Gly Asn Ala Ile Pro
            20                  25                  30
Ser Ser Asp Gln
        35
```

<210> SEQ ID NO 15
<211> LENGTH: 49

```
<212> TYPE: PRT
<213> ORGANISM: Homo sapiens

<400> SEQUENCE: 15

Glu Tyr Lys Tyr Ser Phe Lys Gly Pro His Leu Val Gln Ser Asp Gly
1               5                   10                  15

Thr Val Pro Phe Trp Ala His Ala Gly Asn Ala Ile Pro Ser Ser Asp
            20                  25                  30

Gln Ile Arg Val Ala Pro Ser Leu Lys Ser Gln Arg Gly Ser Val Trp
        35                  40                  45

Thr

<210> SEQ ID NO 16
<211> LENGTH: 123
<212> TYPE: PRT
<213> ORGANISM: Homo sapiens

<400> SEQUENCE: 16

Pro Ala Val Ala Leu Pro His Arg Arg Phe Glu Tyr Lys Tyr Ser Phe
1               5                   10                  15

Lys Gly Pro His Leu Val Gln Ser Asp Gly Thr Val Pro Phe Trp Ala
            20                  25                  30

His Ala Gly Asn Ala Ile Pro Ser Ser Asp Gln Ile Arg Val Ala Pro
        35                  40                  45

Ser Leu Lys Ser Gln Arg Gly Ser Val Trp Thr Lys Thr Lys Ala Ala
    50                  55                  60

Phe Glu Asn Trp Glu Val Glu Val Thr Phe Arg Val Thr Gly Arg Gly
65              70                  75                  80

Arg Ile Gly Ala Asp Gly Leu Ala Ile Trp Tyr Ala Glu Asn Gln Gly
            85                  90                  95

Leu Glu Gly Pro Val Phe Gly Ser Ala Asp Leu Trp Asn Gly Val Gly
            100                 105                 110

Ile Phe Phe Asp Ser Phe Asp Asn Asp Gly Lys
            115                 120
```

METHODS AND COMPOSITIONS FOR REDUCING INFECTIVITY OF VIRUS PARTICLES COMPRISING AN ERGIC-53 POLYPEPTIDE

RELATED APPLICATIONS

This application is a National Stage Filing under U.S.C. § 371 of PCT International Application PCT/US2017/027435, filed Apr. 13, 2017, which was published under PCT Article 21(2) in English, which claims benefit under 35 U.S.C. § 119(e) of U.S. Provisional application having Ser. No. 62/321,928, filed Apr. 13, 2016, the content of each of which is incorporated by reference herein in its entirety.

GOVERNMENT INTEREST

This invention was made with government support under R21 AI088059, AI065359, T32 AI055402 and P20RR021905 each awarded by the National Institutes of Health. The government has certain rights in the invention.

FIELD OF THE INVENTION

The invention relates, in part, to compounds, compositions, and methods to reduce infectivity of virus particles and to treat viral infections in subjects.

BACKGROUND OF THE INVENTION

There are a number of viruses able to cause a severe and sometimes fatal disease in humans and other animals. Viruses are able to interact with and alter their environment in a host during replication and propagation, which suggests an extensive interplay between the viral and host proteomes. In addition, new viruses continue to emerge resulting in disease outbreaks in the absence of effective treatments. Despite the morbidity and mortality caused by these pathogens, there remains a lack of understanding of mechanisms of viral replication and disease.

SUMMARY OF THE INVENTION

According to one aspect of the invention, methods of reducing infectivity of a virus particle are provided. The methods include contacting a virus particle with at least one of: (1) an MCFD2 compound comprising a MCFD2 polypeptide or functional variant thereof; (2) an MCFD2 compound comprising a polynucleotide encoding a MCFD2 polypeptide or functional fragment thereof, and (3) a mimetic of a MCFD2 polypeptide or functional fragment thereof, in an amount effective to reduce the infectivity of the virus particle. In some embodiments, the virus particle is external to a cell not infected with the virus of the virus particle. In some embodiments, virus particle is in a subject. In some embodiments, the subject is suspected of being or known to be infected with the virus of the virus particle. In certain embodiments, reducing the infectivity of the virus particle treats the viral infection in the subject. In some embodiments, the virus is an arenavirus (Mammarenavirus or Reptarenavirus), a coronavirus, a hantavirus, a filovirus, an orthomyxovirus, a herpes virus, a gamma herpes virus, or HIV. In some embodiments, reducing infectivity of the virus particle comprises one or more of reducing propagation of the virus particle; reducing entry of the virus particle into a cell; and reducing release of the virus particle from a cell. In certain embodiments, the functional variant of the polynucleotide has at least 85%, 90%, 95%, 97%, 98%, 99%, or 100% nucleic acid sequence identity to the polynucleotide sequence of which it is a variant. In some embodiments, the functional variant of the polynucleotide sequence comprises a functional fragment of the polynucleotide sequence. In some embodiments, the functional variant of the polynucleotide comprises a fragment of the nucleic acid sequence of the polynucleotide and the fragment has at least 85%, 90%, 95%, 97%, 98%, 99%, or 100% sequence identity to the region of the nucleic acid sequence of the polynucleotide with which it aligns. In certain embodiments, the functional variant of the polypeptide has at least 85%, 90%, 95%, 97%, 98%, 99%, or 100% sequence identity to the amino acid sequence of the polypeptide of which it is a variant. In some embodiments, the functional variant of the polypeptide comprises a fragment of the amino acid sequence of the polypeptide. In some embodiments, the functional variant of the polypeptide comprises a fragment of the amino acid sequence of the polypeptide and the fragment has at least 85%, 90%, 95%, 97%, 98%, 99%, or 100% amino acid sequence identity to the region of the polypeptide's amino acid sequence with which it aligns. In certain embodiments, the functional fragment of the MCFD2 polypeptide comprises MCFD2 EF-hand residues D89 and D129. In some embodiments, the MCFD2 compound allosterically modulates a lectin activity of an ERGIC-53 polypeptide of the virus particle. In some embodiments, contacting the virus particle with the MCFD2 compound comprises administering to the subject MCFD2 polypeptide, or functional variant thereof, or a polynucleotide that encodes the MCFD2 polynucleotide or functional variant thereof. In certain embodiments, contacting the virus particle comprises administering the agent to the subject in an amount effective to reduce the infectivity of the virus particle in the subject. In some embodiments, the MCFD2 polypeptide comprises the sequence set forth as SEQ ID NO: 1, and the encoding polynucleotide comprises the sequence set forth as: SEQ ID NO: 2. In some embodiments, the functional variant comprises an O-glycosylated MCFD2 polypeptide. In certain embodiments, the subject is a human. In some embodiments, the subject is one or more of a mammal, vertebrate, or reptile. In certain embodiments, the functional variant of the MCFD2 polypeptide comprises a fragment of the sequence set forth as SEQ ID NO: 1. In some embodiments, the MCFD2 compound or the mimetic is a modified MCFD2 compound or the mimetic, respectively. In certain embodiments, the modification is a modification to increase the stability of the MCFD2 compound or mimetic. In some embodiments, the modification comprises one or more of: an addition of, an attachment to, and an inclusion of an agent or a component that increases stability, efficacy, half-life, etc. of the MCFD2 compound or mimetic. In certain embodiments, contacting the virus particle comprises administering a composition comprising the MCFD2 compound or mimetic to a subject. In some embodiments, the composition further comprises one or more of a carrier, a delivery agent, and a detectable label. In certain embodiments the composition is a pharmaceutical composition.

According to another aspect of the invention, methods of reducing infectivity of a virus particle are provided. The methods include contacting a virus particle that comprises an ERGIC-53 polypeptide with an inhibitory agent (compound) that specifically reduces one or more of: a level and a function of an ERGIC-53/MCFD2/glycoprotein complex of the virus particle, thereby reducing infectivity of the virus particle. In some embodiments, a function of the ERGIC-53/MCFD2/glycoprotein complex comprises one or more of: propagating the virus particle, releasing the virus particle from a cell, and delivering the virus particle into a cell. In some embodiments, the virus particle is in a subject. In certain embodiments, the subject is suspected of being or known to be infected with the virus of the virus particle. In some embodiments, reducing the infectivity of the virus particle treats the viral infection in the subject. In some embodiments, reducing infectivity of the virus particle comprises one or more of reducing propagation of the virus particle; reducing entry of the virus particle into a cell; and reducing release of the virus particle from a cell. In certain embodiments, the ERGIC-53 polypeptide comprises the sequence set forth as SEQ ID NO: 3, or a functional variant thereof. In some embodiments, the inhibitory compound binds and/or sterically blocks a region of the ERGIC-53 polypeptide that comprises the amino acid sequence corresponding to amino acids 47-60 of the sequence set forth as SEQ ID NO: 3. In certain embodiments, the virus is an arenavirus (Mammarenavirus or Reptarenavirus), a coronavirus, a hantavirus, a filovirus, an orthomyxovirus, a herpes virus, a gamma herpes virus, or HIV. In some embodiments, the inhibitory compound inhibits a function of a carbohydrate recognition domain (CRD) of the ERGIC-53 polypeptide. In some embodiments, the inhibitory compound inhibits a function of one or more of: (1) a GPC binding domain of the CRD, (2) a mannose binding domain of the CRD, and (3) a MCFD2 polypeptide binding motif of the CRD. In certain embodiments, the inhibitory compound binds to at least one of the GPC binding domain, the mannose binding domain, and the MCFD2 polypeptide binding motif and directly inhibits a function of the ERGIC-53 polypeptide. In certain embodiments, the inhibitory compound indirectly reduces one or more of a level and a function of the ERGIC-53 polypeptide. In some embodiments, the inhibitory compound allosterically reduces one or more of a level and a function of the ERGIC-53 polypeptide. In some embodiments, the MCFD2 polypeptide comprises the sequence set forth as SEQ ID NO: 1 or a functional variant thereof, and the encoding polynucleotide comprises the sequence set forth as: SEQ ID NO:2 or a functional variant thereof. In some embodiments, the functional variant of the ERGIC-53 polypeptide and the functional variant of the MCFD2 polypeptide each have at least 85%, 90%, 95%, 97%, 98%, 99%, or 100% sequence identity to the amino acid sequence of the polypeptide of which it is a variant. In certain embodiments, the functional variant of the ERGIC-53 polypeptide comprises a fragment of the amino acid sequence of the ERGIC-53 polypeptide and the functional variant of the MCFD2 polypeptide comprises a fragment of the amino acid sequence of the MCFD2 polypeptide. In some embodiments, the functional variant of the ERGIC-53 polypeptide and MCFD2 polypeptide each comprises a fragment of the amino acid sequence of the ERGIC-53 and MCFD2 polypeptide, respectively, and the fragment has at least 85%, 90%, 95%, 97%, 98%, 99%, or 100% amino acid sequence identity to the region of the polypeptide's amino acid sequence with which it aligns. In some embodiments, contacting the virus particle comprises administering the inhibitory compound to the subject in an amount effective to reduce the infectivity of the virus particle in the subject. In certain embodiments, the subject is a human. In certain embodiments, the subject is a mammal or a reptile. In some embodiments, the inhibitory compound comprises an antibody or functional fragment thereof, a small molecule, or an inhibitory polynucleotide. In some embodiments, the inhibitory compound comprises an antibody or functional fragment thereof that selectively binds at least one of: an ERGIC-53 polypeptide; a MCFD2 polypeptide; an ERGIC-53/MCFD2 polypeptide complex; and a glycoprotein that comprises the ERGIC-53/MCFD2/glycoprotein complex. In some embodiments, the inhibitory compound is an antibody or functional fragment thereof that selectively binds an MCFD2-binding site on the ERGIC-53 polypeptide. In some embodiments, the inhibitory compound is an antibody raised against a combination polypeptide, or a functional fragment thereof. In some embodiments, a combination polypeptide is used raise antibodies may ide comprises all or a fragment the amino acid sequence of ERGIC-53 (SEQ ID NO: 3) and all or a fragment of the amino acid sequence of MCFD2 (SEQ ID NO: 1). In some embodiments, the combination polypeptide is an antigenic polypeptide. In some embodiments, the inhibitory compound a modified compound. In some embodiments, the compound modification is a modification to increase the stability of the inhibitory compound. In some embodiments, the modification comprises one or more of: an addition of, an attachment to, and an inclusion of an agent or a component that increases stability, efficacy, half-life, etc. of the inhibitory compound. In some embodiments, contacting the virus particle comprises administering a composition comprising the inhibitory compound to a subject. In some embodiments, the composition further comprises one or more of a carrier, a delivery agent, and a detectable label. In some embodiments, the composition is a pharmaceutical composition.

According to another aspect of the invention, compositions that include an inhibitory agent (also referred to herein as an inhibitory compound) that reduces infectivity of a virus are provided. In certain embodiments, the composition also includes a pharmaceutically acceptable carrier. In some embodiments, the inhibitory agent is an antibody raised against a combination polypeptide, or a functional fragment thereof. In some embodiments, the inhibitory agent is an antibody that selectively binds one or more of: an ERGIC-53 polypeptide, an MCFD2 polypeptide, an ERGIC-53/MCFD2 polypeptide complex; and a glycoprotein that comprises an ERGIC-53/MCFD2/glycoprotein complex and inhibits infectivity of the virus. In certain embodiments, the virus is an arenavirus (Mammarenavirus or Reptarenavirus), a coronavirus, a hantavirus, a filovirus, an orthomyxovirus, a herpes virus, a gamma herpes virus, or HIV. In some embodiments, the inhibitory compound is an antibody raised against a combination polypeptide, or a functional fragment of the antibody. In some embodiments, the combination polypeptide comprises all or a fragment the amino acid sequence of ERGIC-53 (SEQ ID NO: 3) and all or a fragment of the amino acid sequence of MCFD2 (SEQ ID NO: 1). In some embodiments, the combination polypeptide is an antigenic polypeptide. In some embodiments, the inhibitory compound comprises a modification to increase the stability of the inhibitory compound. In some embodiments, the modification comprises one or more of: an addition of, an attachment to, and an inclusion of an agent or a component that increases stability, efficacy, half-life, etc. of the inhibitory compound. In some embodiments, the composition also includes one or more of a carrier, a delivery agent, and a detectable label, and a stabilizing agent.

Brief Description of the Sequences

SEQ ID NO: 1 is amino acid sequence of Homo sapiens MCFD2 polypeptide having GenBank Accession No. AAP23162.1:

MTMRSLLRTPFLCGLLWAFCAPGARAEEPAASFSQPGSMGLDKNTVHDQEHIMEHL

EGVINKPEAEMSPQELQLHYFKMHDYDGNNLLDGLELSTAITHVHKEEGSEQAPLM

SEDELINIIDGVLRDDDKNNDGYIDYAEFAKSLQ.

SEQ ID NO: 2 is mRNA sequence of Homo sapiens MCFD2 having GenBank Accession No.:. AF537214:

gaagccgaggaagagcgttttggggacggggggctggtgaggctcacgttggagggcttcgcgtctgcttcggagaccgtaaggata ttgatgaccatgagatccctgctcagaaccccttcctgtgtggcctgctctgggccttttgtgccccaggcgccagggctgaggagcc tgcagccagcttctcccaacccggcagcatgggcctggataagaacacagtgcacgaccaagagcatatcatggagcatctagaag gtgtcatcaacaaaccagaggcggagatgtcgccacaagaattgcagctccattacttcaaaatgcatgattatgatggcaataatttgc ttgatggcttagaactctccacagccatcactcatgtccataaggaggaagggagtgaacaggcaccactaatgagtgaagatgaact gattaacataatagatggtgttttgagagatgatgacaagaacaatgatggatacattgactatgctgaatttgcaaaatcactgcagtag atgttatttggccatctcctggttatatacaaatgtgacccgtgataatgtgattgaacactttagtaatgcaaaataactcatttccaactact gctgcagcattttggtaaaaacctgtagcgattcgttacactgggtgagaagagataagagaaatgaaagagaagagaaatgggac atctaatagtccctaagtgctattaaatacctatggacaagggcttgcttcaagcatctgtattagtctgtattaatgctgctgataaagac gtacccgagactgggaagaaaaagaggtttacttggacttacagttccacatggctggggaggcctcagaatcatggcgggaggtga aaggcacttcttacatggcagcaagagaaatgaggaagaagcaaaagtggaaaccctgataagccatcagatcttgtgaaacttat tcactatcacaagaatagcatgggaaagactggcccccatgattcaattacctccccttgggtctctcccacaacacgtgggaattctgg tagatacaatttcaagttgagatttgggtggggacatagccaaaccatatcattctaccctggccctccaaatctcatgtcctcactatt caaaaccaatcatgccttcctaacagtcccccaaagtcttaactcttttcagcattaacgcaaaaatccacagtccaaagtctcatctgag acaaggcaagtcccttccacctatgagcctgtaaaatcaaaagcaagctagttacttcctagataccaacaggggtacaggtattgatta aagacggctgttccaaatgggagaaattggccaaaataaaggggttacagggcccatgcaagtccgaaatccagcagggctgtcaa attttaaagttccagaataatctcctttgactccaggtctcacatccaggtcatactgatgcaagaagtgggttcccatggtcttgggcagc tctgcccctgtggctttgtagggtacagcctccctcctggctgcttcacggctgttgttcagtgcctgcggcttttccaggtgcacggtgc aagctgttggtggatctaccattctggggtctggaggacggtggccctcttctcacagctccactaggcagtgccccagtagggactct gtgtggggctcccacaccacatttcccttctgcactgccctagcagaggttctctcccctgccgctgagagggcctctcccctgcagc aaacgtttgcctgggcattgaggcatttccatacatcttctgaaaactaggcggaggtttccaaatctcaattcttgacttctgtgcacctgc aggcttaacagcacatagaagctgccaaggcttgggcttccactctgaagccacagcccgagctgtatgttggccccttcagccat ggctggagtggctgggacacaagacaccaagtccctaggctgcacacacatgtcaggggctgccctgacatggcctggagacatttt ccccatggtgttggggattaacattaggctccttgctacttatgeaaatttctgcagctggcttgaatttctccccagccaatgggttttctttt tctattgcatagtcaggctgcaaatttccaaacttttatgctttgcttcccttatttataagggaatgcctttaaaagcacccaagtcacctgtt gaacactttgctgcttagaaatttcttccgctagttaacctaaatcatctctctcaagttcaaagttccacaaatccctatggaaggggcaaa atgctgccagtctctttgctaaaacataacaagagtcaccttactccagttcccaacaagttcctcatcttcatctgaggccacctcagcc tggactttgttgtccatattgctatcagcatttggggcaaagccattcaacaagtctgtaggaagttccaaactttcccacatttttcctgttttc ttctgagccctccaaactgttccagcctctgcctgttacccagttccaaagtcacttccacattttgggtatttcttcagcaggtcccaatcta ctggtaccaatttactgtattagtccgttttcacgctgctgataaagacataccgagactgggaagaaaaagtggtttaattggacttaaa gttccacatggctggggaggcctcagaatcatggtgggaggcaaaagacacttcttacattgtggcaagaaaaatgaggaagagc aaaagcagaaaccctgataaactgatcagatctcatgagacttattcactgtcacgagaatagcacgggaaagactggccccatga ttcaattacctcccctgggtctgtcccacaacacgtgggaattctgggagatacaattcaagttgagatttgtgggggacacaaccaa accatatcagcatcctttcaagaatattagataattggagctgagtactcaggaacttgactgtagtagaatactgctagtttcttaattttaat tcacatcacctgaaaagtaaaacaacaggctttgccaagtggatgcttttcagtaacagtgaagtggagtgaataccaaatgtttgccct ggtggttcctatctcttcaggcaaacatggtcagtattctgtaaagttccctggcctaaatgattacttgctctgggcaagtggatatttatt aggctatttcaaagccacagcataagaatgtcagcctagccacagagtctgagattctgagttcagcctagccacagagtctaagattct gtatcctctgacattttggaaatgatacactactggcttaagtgatgactctttcagattttcagtattttatacaactactgccacatccttata ctttattgcttttctgtcttcttcaacctgggagagaccctgaatttgagtgtgttctctaatcaatagtggtttagctttatttctatttca ctcgtttctagggttttttatttgcagtttaggaactattaggaatgtcaggactttatcagcaggggtaaaactaccacctggcctagcctaag taggaagtgaaaagataattcaccaaacaatgattaatcagatagaagttctagtcaagagggatattgttgaagttacctcttttagcctagat acatggattatttcaaatcaggaaagattagaaaaggaacccaaaaaacccttaacagtgtgaatctttatagtatttgaaaatgagaag aagcagcagattgtaatttggtttattggatgtgatggacgttctgtaatagaaaacctgaaacgatgattgaatgggaaaaagagactac aaaatttgtcgtaggatgtatacagacttattttctttattacagtattataagaaaacatatgtatttgtaaaaatggtttcctgtgtcaagt atttgtgcagtcagagctgacttgtaaactattcttgtaatagctcattattttgaaagatttatatatgatgaattctggatatatgaccaat aaaactgatgaagc.

SEQ ID NO: 3 is amino acid sequence of ERGIC-53 protein having GenBank Accession No. NP_005561.1

MAGSRQRGLRARVRPLFCALLLSLGRFVRGDGVGGDPAVALPHRRFEYKYSFKGPH

LVQSDGTVPFWAHAGNAIPSSDQIRVAPSLKSQRGSVWTKTKAAFENWEVEVTFRV

TGRGRIGADGLAIWYAENQGLEGPVFGSADLWNGVGIFFDSFDNDGKKNNPAIVIIG

NNGQIHYDHQNDGASQALASCQRDFRNKPYPVRAKITYYQNTLTVMINNGFTPDKN

DYEFCAKVENMIIPAQGHFGISAATGGLADDHDVLSFLTFQLTEPGKEPPTPDKEISEK

EKEKYQEEFEHFQQELDKKKEEFQKGHPDLQGQPAEEIFESVGDRELRQVFEGQNRI

HLEIKQLNRQLDMILDEQRRYVSSLTEEISKRGAGMPGQHGQITQQELDTVVKTQHEI

LRQVNEMKNSMSETVRLVSGMQHPGSAGGVYETTQHFIDIKEHLHIVKRDIDNLVQ

RNMPSNEKPKCPELPPFPSCLSTVHFIIFVVVQTVLFIGYIMYRSQQEAAAKKFF.

SEQ ID NO: 4 is mRNA sequence of Homo sapiens ERGIC-53 (aka LMAN-1) having GenBank Accession No.: NM_005570 ctcccgccctcctccgcgttccagaatccaagatggcgggatccaggcaaaggggtctccgggccagagttcggccgctgttctgcg ccttgctgctgtcactcggtcgcttcgtccggggcgacggcgtgggaggagaccccgcggtcgcgttgccacatcgccgtttcgagt acaaatacagcttcaaggggccgcacctggtgcagagcgacgggaccgtgcccttctgggcccacgcggggaatgctattccaagt tcagatcaaattcgagtagcaccatctttaaaaagccaaagaggctcagtgtggacaaagacaaaagcggcctttgagaactgggaa gttgaggtgacatttcgagtgactggaagaggtcgaattggagctgatggcctagcaatttggtatgcagaaaatcaaggcttggagg gccctgtgtttggatcagctgatctgtggaatggtgttggaatattttttgattcttttgacaatgatggaaagaaaaataatcctgctatagt aattataggcaacaatggacaaatccattatgaccatcaaaatgacgggctagtcaagctttggcaagttgccagagggacttccgca acaaaccctatcctgtccgagcaaagattacctattaccagaacacactgacagtaatgatcaataatggctttacaccagataaaaatg attatgaattttgtgccaaagtggaaaatatgattatccctgcacaagggcattttggaatatctgctgcaactggaggtcttgcagatgac catgatgtcattatttctgactttccagttgactgaacctggaaaagagccgcccacaccagataaagaaatttcggaaaaggaaaaa gaaaagtatcaggaggaatttgagcacttttcaacaagaattggataaaaaaaaagaggaattccagaagggccaccccgacctccaa gggcagcctgcggaggaaatatttgagagtgtaggagatcgagagctaagacaagtctttgaaggacagaatcgtattcatcttgaaat caagcagctgaaccggcagttagatatgattcttgatgaacagagaagatatgtctcttccttaacagaggaaatctctaaaagaggag caggaatgcctgggcagcatgggcagattactcaacaagaacttgatactgttgtgaaaactcagcatgagattctgagacaagtaaa tgaaatgaaaaattccatgagtgaaaccgtcagactggtcagtggaatgcagcaccctggctctgctggaggcgtctatgagacaaca

```
cagcacttcattgacatcaaagagcacctgcacatagtaaagagggacatagataacttagtgcagcgaaatatgccatcaaatgaaa
agccgaaatgcccagaactaccaccatttccatcatgtttgtctacggtccacttcattatatttgttgtggtgcaaactgtattattcattggt
tatatcatgtataggtctcagcaagaagcagctgccaaaaaattcttttgactaccattttcctgtgtacttcatctatttgtgtacaaaatgat
gtcgttttgagggaatttaagtatttaaattgcttcatagtctaaattattaattttcttaataaaataactgtttaaacattgatttgcagt
taagaataaaccttaaagcaaagacaaccacattttaatttgttcacagtatgtaaatctgtctaaattcagtgaatttctggtcagtatgat
gcagcctctgagcagaatattgaccagtaagagggtaaataaagtgggggcaacccctggatatgaatgttacccctaagtctccaatattgc
aggtttcctgtataacgtaaacacacttgccctcatgcctcccagaatatgaggtctaattaagaagtcccatcaggtttattttgtaacca
aagtattttagaggtcagacttcctaatcaaaggcctgggcctgcagtcctttcatcttaatgcaacttcctttgaaatcaaagaatattttg
tctgagagctttaaggatctggtaatagacttcaaaatgttaagtgaatttttttttcctctatttatcaatgatatatttcacttttaaagg
aaattttagaggaaaattaatagctgcttttgcctaaaaaaccttgtgggtggaaacattcctctgagaatggcttttataggtattttgcc
tggtaatgtattcattcatgattgcccatattcttgaatgtcttcattccaatggggtcaggtcaatattatgaaaataatttttatatttatatt
tgtaacttaaggaatttatttctccctttactacagcatgtaaattcagctcaaattgcatgatctgaggatttaaattcacaaaacctgccact
acattctggtttacattagttacttcatgctggctggggttagtgaccatttgcatactcttaaatcaaggcggctgtagtagcagcagttttaa
gattcttgaaggcaaaatttgaaaaacagtgaatacttctaattgtttcatttagtgccagaactaaggacattgtgaagcacttgttagtaaact
taaccttgaaatgtcagactggaaggagtttttatagtctttgtgcatacttctaggtattacagaaacagtctgtaaatgacattttaagatgc
aaatttaattctgttcacagctgatttatactgattttgctgccttcaaaatactcttttacttttagctaaaatggttgtctttcatttgcc
atagaattccaaacaatactatcttataaaatagtactgttgaattattccaagcctccctaggtttgctctcaaatgtcatttacagattgggc
taacgacctaaaatctatatataaagactttctgaagaactctgtattatagcaataccaaacgagtgctgtgtgtgcaaacagtctggcgttgc
ttttatgttgatatttatcctagaacactgaaagagaatatgccagtgataactcactttacttcagtcatttcaacacagaaaatgcttctct
agcatttttcttttgtagtgttaacattttgaaattcatgtttcagaggcttcatcatcacagaatttactcttgctccatgaaaaaaaattaa
ataccttcagaggaatatttaagttgtaaactatgaaacttgagaaatcctcttgagataaaaggctgccaaatccagtattataaagtccatgg
tcatatgtgcctgtgcattaaaggaataccagatctatgcagtatacattttcaggctgaaattcaaggggaatcattctgattattcttact
acaaatggagatggctattatgaaacagcatgagcatgagccttttatctttatacttagtgatatactttgcttgaaaatcactcagcaaa
gtagttcacatgatgtgtatcatatttgaagtgtggttttctcaaaatcattgactttaaggagctcatttctgaacaaaaggtttgctctgtg
gaaaaatcaatcactgccaggattattcatttctgtactattttgtataattgaatttgttcacttctctcacaccagcaagtgttttacaggtg
ccttggattaaaacaaaattgattttaaaattttatgtaagtcattgtgtctatgatgccacttttaaaggaaaatgcaattgcgtaatggctt
atatccttatttaatgtacctatttgtgttctaataattgtttgaatgttttattcagcttaaaactttaccatgaagtcataaacagtaaacaa
tgttttgttatgtattaaggggatatcagtgtttctcaaagtatgatccatggaccatctgggtcatggcgcctggtttcagacaacctgaatcaa
atcttaggggtggggctttgggatgtcattgttcaataggcacctcaggagattctgagcacaccaatgtttgagaaccactaaaatgag
gagtgggaaaaaaaaataggtgttttgttaatttagagctgagctgagaagataatatattttattgtcaatgacattaacagatatgcac
tgattatttatacctacaatttacttaatgttcatttattaaaacgcgtggttcatgagcaactacagactgaatccagattattacctgttgct
ttcagtattttcgtgatggcttttaatcttatgaaatcatcttgagatcattcatggtcaagccatgaaaactcccatcttcaagcctgcctgct
aaagcttctttgccttcctgattgtgattatggtaacaatttatatcagacagttgtacttttgataacttagggaaaacagaaatgacttgaa
caagggattgcctgcctcactgcattgcagagatacaattttgtaaagaacacaaatagcagttgtgaatattaaggtgtgattatattcc
ctgtccatgtgcttattgaaagaagatagtgaacaaatgattatattgaggattttttaatttataagatctaatgtgaaatccacacttggaa
cttttagatctgtctgttgcttgtttaatatatttctttatgacattacttaaagtttaaaagggttttctatccactgtcaatttcaattgga
taacattttgtcaagtttttttttttcctgattatttgatgctagctggaattcaagaaatggcattgaccttattcaaataaagaaatattta
gtaaaaaaaaaaaaaaa.
```

SEQ ID NO: 5 is amino acid sequence of a MCFD2 polypeptide that is a fragment of SEQ ID NO: 1:

MTMRSLLRTPFLCGLLWAFCAPGARAEEPAASFSQPGSMGLDKNTVHDQEHIMEHL

EGVINKPEAEMSPQELQLHYFKMHDYDGNNLLDGLELSTAITHVHKEEGSEQAPLM

SEDELINIIDGVLRDDDKNNDGYIDYAEFAK.

SEQ ID NO: 6 is amino acid sequence of an MCFD2 polypeptide that is a fragment of SEQ ID NO: 1:

PAASFSQPGSMGLDKNTVHDQEHIMEHLEGVINKPEAEMSPQELQLHYFKMHDYDG

NNLLDGLELSTAITHVHKEEGSEQAPLMSEDELINIIDGVLRDDDKNNDGYIDYAEFA

KSLQ.

SEQ ID NO: 7 is amino acid sequence of an MCFD2 polypeptide that is a fragment of SEQ ID NO: 1:

KMHDYDGNNLLDGLELSTAITHVHKEEGSEQAPLMSEDELINIIDGVLRDDDKNNDG

YIDYAEFAKSLQ.

SEQ ID NO: 8 is amino acid sequence of an MCFD2 polypeptide that is a fragment of SEQ ID NO: 1:

NNLLDGLELSTAITHVHKEEGSEQAPLMSEDELINIIDGVLRDDDKNNDGY.

SEQ ID NO:9 is a cytoplasmic portion of a ERGIC-53 polypeptide set forth as SEQ ID NO: 3:

QQEAAAKKFF.

SEQ ID NO: 10 is transmembrane and cytoplasmic/cystolic portion of an ERGIC-53 polypeptide set forth as SEQ ID NO: 3:

TVHFIIFVVVQTVLFIGYIMYRSQQEAAAKKFF.

SEQ ID NO: 11 is a portion of SEQ ID NO: 3 from residue 1 through 477:

MAGSRQRGLRARVRPLFCALLLSLGRFVRGDGVGGDPAVALPHRRFEYKYSFKGPH

LVQSDGTVPFWAHAGNAIPSSDQIRVAPSLKSQRGSVWTKTKAAFENWEVEVTFRV

TGRGRIGADGLAIWYAENQGLEGPVFGSADLWNGVGIFFDSFDNDGKKNNPAIVIIG

NNGQIHYDHQNDGASQALASCQRDFRNKPYPVRAKITYYQNTLTVMINNGFTPDKN

DYEFCAKVENMIIPAQGHFGISAATGGLADDHDVLSFLTFQLTEPGKEPPTPDKEISEK

EKEKYQEEFEHFQQELDKKKEEFQKGHPDLQGQPAEEIFESVGDRELRQVFEGQNRI

HLEIKQLNRQLDMILDEQRRYVSSLTEEISKRGAGMPGQHGQITQQELDTVVKTQHEI

LRQVNEMKNSMSETVRLVSGMQHPGSAGGVYETTQHFIDIKEHLHIVKRDIDNLVQ

RNMPSNEKPKCPELPPFPSCLS.

SEQ ID NO: 12 is a fragment of SEQ ID NO: 3 that includes amino acids 44 to 268 of SEQ ID NO: 3:

RRFEYKYSFKGPHLVQSDGTVPFWAHAGNAIPSSDQIRVAPSLKSQRGSVWTKTKA

AFENWEVEVTFRVTGRGRIGADGLAIWYAENQGLEGPVFGSADLWNGVGIFFDSFD

NDGKKNNPAIVIIGNNGQIHYDHQNDGASQALASCQRDFRNKPYPVRAKITYYQNTL

TVMINNGFTPDKNDYEFCAKVENMIIPAQGHFGISAATGGLADDHDVLSFLTFQLT.

SEQ ID NO: 13 is a fragment of SEQ ID NO: 3 that includes amino acids 47-60 of SEQ ID NO: 3: EYKYSFKGPHLVQS.

SEQ ID NO: 14 is a fragment of SEQ ID NO: 3:
RRFEYKYSFKGPHLVQSDGTVPFWAHAGNAIPSSDQ.

-continued

SEQ ID NO: 15 is a fragment of SEQ ID NO: 3:
EYKYSFKGPHLVQSDGTVPFWAHAGNAIPSSDQIRVAPSLKSQRGSVWTK.

SEQ ID NO: 16 is a fragment of SEQ ID NO: 3:

PAVALPHRRFEYKYSFKGPHLVQSDGTVPFWAHAGNAIPSSDQIRVAPSLKSQRGSV

WTKTKAAFENWEVEVTFRVTGRGRIGADGLAIWYAENQGLEGPVFGSADLWNGVG

IFFDSFDNDGK.

SEQ ID NO: 17 is a fragment of SEQ ID NO: 3:
GTVPFWAHAGNAIPSSDQIRVAPSLKSQRGS.

SEQ ID NO: 18 is a fragment of SEQ ID NO: 3:

VTGRGRIGADGLAIWYAENQGLEGPVFGSADLWNGVGIFFDSFDNDGKKNNPAIVII

GNNGQIHYDHQNDGASQALASCQRDFRNKPYPVRAKITYYQNTLTVMINNGFTPDK

NDYEFCAKVENMIIPAQGHFGISAATGGLADDHDVLSFLTFQLT.

SEQ ID NO: 19 is a fragment of SEQ ID NO: 3:

FDNDGKKNNPAIVIIGNNGQIHYDHQNDGASQALASCQRDFRNKPYPVRAKITYYQN

TLTVMINNGFTPDKNDYEFCAKVENMIIPAQGHFGISAATGGLADDHDVLSFLTFQL

T.

SEQ ID NO: 20 is a fragment of SEQ ID NO: 3:

SCQRDFRNKPYPVRAKITYYQNTLTVMINNGFTPDKNDYEFCAKVENMIIPAQGHFG

ISAATGGLADDHDVLSFLTFQLT.

BRIEF DESCRIPTION OF THE DRAWINGS

FIG. 1A-C illustrates that overexpression of WT MCFD2 leads to impairment in production of infectious JUNV C #1 and DANV. HEK293T cells were transfected with a plasmid encoding MCFD2 or an empty plasmid. 24 hr. following transfection, cells were infected with JUNV C #1 at an MOI of 0.1, or DANV at an MOI of 0.001, and after 48 hours (FIGS. 1A and 1C) or 72 hours (FIG. 1B) post-infection (hpi) supernatants were screened for number of plaque forming units (PFU) by a standard plaque assay on Vero E6 cells. Data are from replicate experiments (n=6, 48 hpi C #1 and n=3 DANV, n=6 72 hpi C #1) and are presented as mean PFU±SEM relative to the cells receiving the empty vector. FIG. 1D is a graph showing that production of infectious JUNV C #1 was enhanced in MCFD2 null cells. EBV transformed lymphoblastoid cells from a healthy $MCFD2^{+/+}$ donor (2829D) and $MCFD2^{-/-}$ individuals with F5F8D (CRC-80 and 1258) were challenged with JUNV C #1 at an MOI of 1.0 and 72 hpi supernatants were screened for PFU via plaque assay. Data are presented as mean PFU±SEM relative to the $MCFD2^{+/+}$ cells. Data are representative of two independent experiments (n=6 per condition per experiment). FIG. 1E provides photographic images of MCFD2 expression and trafficking during infection with an arenavirus. HEK293T infected cells infected with JUNV C #1 were fixed 72 hpi and stained internally for JUNV GP (green) and MCFD2 (red) and visualized by confocal microscopy. The image is representative of a minimum of 10 fields of view. Background signal was subtracted via gain reduction based on values obtained from secondary antibody alone (MCFD2) or mock infected cells (GP). FIG. 1F provides images of blots showing results that demonstrating that MCFD2 forms an ERGIC-53 dependent tripartite complex with JUNV C #1 GP that requires MCFD2 EF-hand residues 89 and 129. HEK293T cells were co-transfected with a modified PCAGGS vector (pCC384) encoding JUNV C #1 GP with a carboxy-terminal biotin acceptor peptide (BAP), for efficient streptavidin based purification, and an HA epitope used for detection of GPC and GP2 by Western blot; a bacterial biotin ligase, BirA, to ensure in-situ biotinylation, and plasmids encoding the indicated versions of ERGIC-53 and MCFD2. Biotinylated proteins were isolated using streptavidin coated beads, and purified complexes were eluted and analyzed by SDS PAGE and Western blot detection of GPC/GP2 (bait), FLAG-ERGIC-53 (prey), MYC-MCFD2 (prey), and CRT as a control. FIG. 2A-B provides blots and a graph of results demonstrating that MCFD2 antiviral action is conserved across multiple pathogenic RNA viruses and is specific to the viral GP. FIG. 2A shows results indicating that MCFD2 forms a tripartite complex with arenavirus, coronavirus, filovirus, hantavirus, and orthomyxovirus envelope glycoproteins. HEK293T cells were co-transfected with modified PCAGSS vectors (pCC384) with carboxy terminal BAP and HA features for purification and detection procedures encoding the respective viral GPs: LASV GP, JUNV XJ GP, ANDV GP, EBOV GP, MARV GP, SARS S, VN HA (H5), WSN HA (H1), and VSV G, along with WT ERGIC-53 and MCFD2, as well as BirA to ensure in-situ biotinylation. Streptavidin precipitated GP-cellular protein complexes were analyzed via SDS PAGE and Western blot for GP (bait) content, ERGIC-53, and MCFD2 (prey) content along with CRT as a control. FIG. 2B is a graph showing that MCFD2 has a highly conserved antiviral function that can be restricted to the viral glycoprotein. HEK293T cells were first transfected with either an empty plasmid, or one encoding WT MCFD2. The following day cells were transfected with each of the respective viral glycoproteins: VSV G, JUNV XJ GP, SARS S, MARV GP, EBOV GP, and ANDV GP. 24 hr following the final transfection, monolayers were infected with VSVΔG-GFP pseudo-particles decorated with VSV G. Supernatants were harvested 24 hpi to assay for focus forming units (FFU) on fresh Vero monolayers. Data are presented as mean FFU±SEM relative to the cells receiving an empty vector. Data are representative of two independent experiments (n=3 per condition per experiment).

FIG. 3A-B provides graphs of results demonstrating that MCFD2 regulates ERGIC-53's lectin activity to inhibit arenavirus replication. FIG. 3A is a graph illustrating that ERGIC-53's CRD is critical for production of infectious JUNV C #1. HEK 293T cells were transfected with either an empty plasmid, or one containing WT ERGIC-53, ERGIC-53 ΔCRD, or WT MCFD2. Monolayers were infected 24 hpi with JUNV C #1 at an MOI or 0.1, virus containing supernatants were harvested at 48 hpi and assayed for PFU content via standard plaque assay. Data are represented as mean PFU±SEM relative to the cells receiving an empty vector. FIG. 3B is a graph illustrating that interactions of ERGIC-53's CRD regulate arenavirus production. HEK 293T cells were co-transfected with either an empty plasmid, or one containing WT MCFD2 in tandem with WT and functional mutants of ERGIC-53 to test for their relative contributions to the ERGIC-53 dependent phenotype; ΔCRD (unable to bind GP, MCFD2, or sugar), Δβ1 (unable to bind MCFD2), Δβ4 (unable to bind MCFD2 or sugar), N156A (unable to bind sugar). Monolayers were infected 24 hpi with JUNV C #1 at an MOI or 0.1, virus containing supernatants were harvested at 72 hpi and assayed for PFU content via standard plaque assay. Data are represented as PFU±SEM relative to the cells receiving equal μg amounts of the empty vector.

FIG. 4A is a blot showing that purified MCFD2 interacts with ERGIC-53 secreted from infected and mock infected cells. MCFD2 purified from HEK293T cells (see Example 1 for details on purification) was added to clarified supernatant from JUNV C #1 and mock infected cultures. Recombinant MCFD2 in complex with ERGIC-53 was immunoprecipitated using an anti myc antibody that recognizes the recombinant MCFD2 molecule. Precipitated fractions were separated via SDS PAGE and analyzed by Western blot for the presence of myc-MCFD2 (bait) and endogenous ERGIC-53 (prey). FIG. 4B shows graphs of results indicating that purified MCFD2 is able to inhibit the entry of Old and New World arenaviruses. Purified MCFD2 or vehicle was added to supernatant containing 200 PFU of JUNV C #1 or DANV derived from Vero E6 cells. The supernatant was incubated with purified protein for 2 hr at 4° before being overlaid onto monolayers of HEK293T cells. Following a 2 hr adsorption at 37° the cells were washed extensively and fresh medium was added. At 48 (DANV) and (72) hpi, supernatants were harvested and assayed for PFU content by standard plaque assay. Data are represented as mean PFU±SEM relative to the supernatant treated with vehicle. FIG. 4C-D are photomicroscopy images of results illustrating that 2D and 3D 3dSTORM imaging reveals organization of sMCFD2 and ERGIC-53 on arenavirus particles. JUNV C #1 containing particles generated in Vero E6 cells were fixed onto poly-L-Lysine treated MatTek dishes. Following fixation with PFA, adsorbed virions were permeablized and incubated with purified sMCFD2 from HEK293T cells prior to staining for myc-MCFD2, JUNV NP, and endogenous ERGIC-53. Images are representative from a minimum of 10 acquisitions of 15,000 to 30,000 frames. Scale bars are indicated for each image. Signal versus noise values were assessed by imaging single fluorophores in their respective channels, as well as in all 3 channels to ensure localizations from each respective fluorophore were distinct. The two rows in FIG. 4C are of a 1,000 nm view of a series of JUNV C #1 particles, and then a single particle magnified. The image in FIG. 4D is a 3D rendering of an individual JUNV C #1 virion identified via NP staining (leftmost image) containing a ring of ERGIC-53 (second from left image) and MCFD2 (third from left image). The image furthest to the right is a merged image of the other three images.

FIG. 6A shows results of SDS-PAGE/Western Blot analysis of recombinant MCFD2 (pre-His/Ni purification). FIG. 6B shows results of SDS-PAGE/Western Blot analysis of recombinant MCFD2 (post-His/Ni purification).

FIG. 7 is a schematic diagram of an ERGIC-53 polypeptide complex showing the lumen and illustrating the GPC, Mannose, and MCFD3 binding-zone regions.

DETAILED DESCRIPTION

Figure 1A:
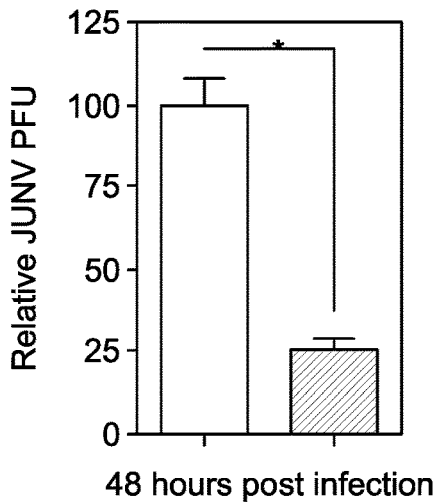
FIG. 1A-F provides graphs, photomicroscopy images, and gel images demonstrating that MCFD2 is an arenavirus restriction factor that forms a tripartite complex with ERGIC-53 and JUNV GP.

The invention, in part, pertains to methods and compounds that can be used to reduce infectivity of a viral particle. Reducing infectivity of a virus particle may include one or more of: reducing propagation of the virus particle; reducing entry of the virus particle into a cell; and reducing release of the virus particle from a cell. Embodiments of methods and compounds of the invention can be used to treat viral infection in cells and subjects. It has been identified that surprisingly, increasing the level of MCFD2 protein contacting a viral particle can reduce the infectivity of the viral particle. Thus, some aspects of the invention include methods of increasing contact of a viral particle with a MCFD2 compound that includes an MCFD2 molecule, or functional variant thereof. In certain embodiments of the invention, an MCFD2 molecule is a polynucleotide molecule that encodes an MCFD2 protein or functional variant thereof. In certain embodiments of the invention a MCFD2 molecule is a MCFD2 protein. Thus MCFD2 compounds and methods of the invention to increase the level of a MCFD2 protein can inhibit infectivity of a virus particle and are useful to treat an infection of a cell and/or subject by that virus.

It has also now been identified that contacting a virus particle with one or more inhibitory compounds comprising an inhibitory agent that reduces a function and/or level of an ERGIC-53 complex. In some aspects of the invention an ERGIC-53 complex comprises an ERGIC-53 protein and an MCFD2 protein. In certain aspects of the invention, an ERGIC-53 complex comprises an ERGIC-53 protein, an MCFD2 protein, and one or more glycoproteins. Thus, the invention, in part, includes inhibitory agents and inhibitory compounds that when contacted with a viral particle, reduce activity of an ERGIC-53 complex of the viral particle thereby reducing infectivity of the virus particle. Such inhibitory agents and compounds of the invention can be used to treat an infection of a cell and/or a subject by the virus.

As used herein, an inhibitory agent or MCFD2 molecule that is contacted with a viral particle is an exogenous inhibitory agent or MCFD2 molecule. As used herein, the term "exogenous" when used in reference to an inhibitory agent or a MCFD2 molecule means a molecule that is administered to a viral particle and does not include the inhibitory agent or MCFD2 molecule that may naturally contact the virus particle. For example, an inhibitory agent or MCFD2 molecule administered to a cell and/or subject is an exogenous inhibitory agent or MCFD2 molecule, respectively, even if the same inhibitory agent or MCFD2 molecule may be naturally present in a cell and/or subject. As used herein, an inhibitory agent of the invention or a MCFD2 molecule that is present in a cell and/or subject due to natural expression in the cell and/or subject and is referred to as "endogenous".

In certain aspects of the invention an inhibitory compound or MCFD2 compound of the invention optionally includes one or more targeting agents that can be used to deliver the inhibitory agent compound or MCFD2 compound to a cell and/or tissue that includes one or more viral particles. In certain embodiments of the invention treatment of a virus particle, cell, and/or subject with an inhibitory compound or MCFD2 compound may comprise contacting one or more viral particles with one or more inhibitory compounds and MCFD2 compounds, in an amount effective to reduce the infectivity of the contacted viral particle.

In certain aspects of the invention, contacting a virus particle with an MCFD2 molecule or an inhibitory agent of the invention and/or administering an MCFD2 molecule or an inhibitory agent of the invention to a virus particle, mean that the virus particle is contacted with an exogenous MCFD2 molecule or inhibitory agent of the invention. The terms "contacted with" and "administered to" are used interchangeably herein in reference to a viral particle or a cell. For example, administering a MCFD2 molecule or inhibitory agent to a virus particle may be referred to as contacting the virus particle with the MCFD2 molecule or inhibitory agent, respectively.

An MCFD2 molecule, non-limiting examples of which are set forth herein as SEQ ID NO: 1 and SEQ ID NO: 2, or functional variants thereof may in some aspects of the invention be administered to a virus particle as a portion of or the entirety of an MCFD2 compound of the invention. An MCFD2 compound of the invention includes an MCFD2 molecule and optionally one or more additional elements. An inhibitory agent of the invention may, in some aspects of the invention be administered to a virus particle as a portion of or the entirety of an inhibitory compound of the invention. An inhibitory compound of the invention includes an inhibitory agent of the invention and optionally one or more additional elements. Non-limiting examples of additional elements that may be included in an inhibitory compound or MCFD2 compound of the invention include: targeting agents, detectable labels, additional anti-viral agents, vectors, etc.

Molecules, agents, compounds, compositions, and methods of the invention may be used to treat a subject having, or at risk of having a virus infection. Contacting a virus particle in a cell, on a cell, and/or in a subject with one or more of an inhibitory compound and MCFD2 compound of the invention in an amount effective to inhibit infectivity of the virus particle, treats an infection by the virus of the cell and/or subject. Certain aspects of the invention include methods and compounds useful to a treat viral infection in cells and in subjects. A virus particle whose infectivity may be inhibited by one or more inhibitory compounds and MCFD2 compounds of the invention, may be an RNA virus particle. One or more virus particles in a cell, on a cell, and/or in a subject indicate infection of the cell and/or subject, respectively, with that virus. Viral infections that may be treated using an inhibitory compound or MCFD2 compound in methods of the invention to inhibit virus particle infectivity include but are not limited to RNA viruses. Examples of virus particles and viruses that may be inhibited and treated, respectively, using compounds and methods of the invention include, but are not limited to: arenaviruses (Mammarenaviruses or Reptarenaviruses), a coronavirus, a hantavirus, a filovirus, an orthomyxovirus, a herpes virus, a gamma herpes virus, or HIV. Virus particles that may be inhibited and the viruses treated using methods and compounds of the invention may include Old World viruses, New World viruses, emerging RNA viruses in which MCFD2 and ERGIC-53 have a role in infectivity of the virus, and DNA viruses in which MCFD2 and ERGIC-53 have a role in infectivity of the virus. Non-limiting examples of additional viruses that may be inhibited and treated using compounds and methods of the invention viruses are herpes viruses and Human Immunodeficiency Virus (HIV).

A virus particle whose infectivity is inhibited using a method, compound, or composition of the invention may be present in or on a cell that is an in vitro or in vivo cell. An in vivo cell may be in a subject. The presence of one or more of a viral particle in or on one or more cells, and/or in a subject means the virus is present in the cell and/or subject. As used herein a cell that comprises a viral particle means a cell that has the viral particle in the cell interior and/or or associated with the exterior of the cell. In some aspects of the invention a cell may be in culture or may be in a subject.

A treatment according to some aspects of the invention may be applied to a cell or subject that comprises one or more of a virus particle, and generally a cell or subject comprising a plurality of the virus particle. As used herein the term "one or more" when used in reference to a virus particle means a single virus particle or a plurality of virus particles. A plurality of virus particles may include 2, 3, 4, 5, 6, 7, 8, 9, 10, 20, 50, 100, 500, 1,000, 5,000, 10,000, or more virus particles, including all integers in between. A plurality of virus particles may be a homogeneous or heterogeneous set of virus particles. As used herein, a homogeneous plurality of virus particles means virus particles of a single virus and a heterogeneous plurality of virus particles means a plurality of virus particles that includes virus particles from two or more different viruses. It will be understood that in certain instances a cell or subject may comprise more than one virus, or may be suspected of comprising more than one virus that may be treated with an embodiment of a compound and treatment method of the invention.

As used herein, a subject shall mean a vertebrate animal including but not limited to a human, non-human primate, mouse, rat, guinea pig, rabbit, cow, dog, cat, horse, goat, bird, reptile, or fish. In certain aspects of the invention, a subject is a mammal. In certain aspects of the invention a subject is a reptile. In certain aspects of the invention, a subject may be a domesticated animal, a wild animal, or an agricultural animal. Thus, the invention can be used to inhibit virus particle infectivity and to treat viral infections in human and non-human subjects. For instance, methods and compositions of the invention can be used in veterinary applications (for examples in zoos, reserves, farms, in the wild, etc.) as well as in human treatment regimens. In some embodiments of the invention, the subject is a human. In some embodiments of the invention, a subject is at risk of having, or has a viral infection. In some aspects of the invention, a cell is a cell that contains a virus particle. In certain aspects of the invention a cell is a cell that is in contact with a virus particle on its external surface. In some aspects of the invention, a method of treating a virus reduces infectivity of a virus particle that is external to a cell that is not infected with the virus of the virus particle. Some embodiments of methods of the invention can be used to inhibit infectivity of a virus particle such that it does not enter a cell, does not leave a cell it is in, and/or does not propagate.

Cells that may be in contact with and treated using a method or compound of the invention include, but are not limited to: a lung cell, a circulatory cell, an epithelial cell, an endothelial cell, a neuronal cell, a glandular cell, a renal cell, a hematopoietic cell, a lymphoid cell, a cardiac cell, a hepatic cell or other cell that can be infected with a virus that can be treated using methods and compounds of the invention.

Non-limiting examples of subjects and cells to which methods and compounds of the present invention can be applied are subjects and cells that are diagnosed with, suspected of having, or believed to be at risk of having one or more viral infections. Methods of the invention may be applied to a subject who, at the time of treatment using a method and/or compound of the invention, has been diagnosed with a viral infection. Methods of the invention to treat a viral infection can be administered before, during, and/or after application of other treatments for a viral infection including, but not limited to administering additional anti-viral agents, pain medications, or other therapeutic support agents; surgical procedures; and supportive treatments including, but not limited to: hydration, rest, isolation, respiratory support, etc.

In some aspects of the invention, a subject is at risk of having or developing a viral infection that may be treated using methods and compounds of the invention. A subject at risk of developing a viral infection has an increased probability of developing the viral infection compared to a control risk of developing the viral infection. In some embodiments of the invention, a level of risk may be statistically significant compared to a control level of risk. A subject at risk may include, for instance, a subject who is suspected to or known to have been exposed to a virus reservoir (a non-limiting example of which is rodent that harbors hantavirus); a subject who is suspected to or known to have been exposed to one or more humans or animals believed or known to be infected with the virus; a subject known to have had a previous diagnosis of the virus, who may be at risk for a relapse.

In some aspect of the invention, increasing a level of one or more of an inhibitory compound and MCFD2 compound of the invention in a cell, tissue, or subject may treat a viral infection. In some embodiments of the invention, contacting a virus particle with an exogenous inhibitory compound and/or MCFD2 compound increases the level of the inhibitory agent and/or MCFD2 molecule in the cell and inhibits infectivity of the virus particle, as compared to a substantially similar virus particle not contacted with the exogenous inhibitory compound and/or MCFD2 compound. Decreasing infectivity of a virus particle means that a cell and/or subject comprising the virus particle is treated for the viral infection, as compared to a substantially similar cell and/or subject in which the virus particle was not contacted with the inhibitory compound and/or MCFD2 compound of the invention. Some aspects of the invention include methods of administering an exogenous inhibitory agent and/or a MCFD2 molecule to a cell, tissue, and/or subject in an amount effective to inhibit infectivity of a viral particle in the cell, tissue, and/or subject as a treatment for the viral infection.

Levels of virus infectivity and infection after treatment with an inhibitory agent or MCFD2 molecule of the invention can be determined and compared to control values of the virus' infectivity and infection by the virus. Levels of activity and function of an ERGIC-53 complex can be determined and compared to a control level of activity of the ERGIC-53 complex. A control value may be a predetermined value, which can take a variety of forms. It can be a single cut-off value, such as a median or mean. It can be established based upon comparative groups, such as in groups of virus particles having normal amounts of infectivity and groups of virus particles having abnormal (for example reduced) amounts of infectivity. As another non-limiting example, it can be established based upon comparative groups, such as in groups of cells or individuals having exposure to virus particles with and without administration of an inhibitory agent or MCFD2 molecule of the invention. Another example of comparative groups may be groups of cells or subjects having one or more symptoms of, or a diagnosis of, a viral infection and groups of cells or subjects without one or more symptoms of, or a diagnosis of, the viral infection. The predetermined value, of course, will depend upon the particular population selected. For example, an apparently healthy population of cells may have a different "normal" range than a population of cells or subjects exposed to a virus. Accordingly, the predetermined value selected may take into account the category in which a virus particle, subject, or cell falls. Appropriate ranges and categories can be selected with no more than routine experimentation by those of ordinary skill in the art. As used herein, "abnormal" means significantly different as compared to a normal control.

It will be understood that controls according to the invention may be, in addition to predetermined values, samples of materials tested in parallel with the experimental materials. Examples include samples from control populations or control samples generated through manufacture to be tested in parallel with the experimental samples; and also a control may be a sample from a subject prior to, during, or after a viral infection, including but not limited to a subject treated using methods and compounds of the invention.

In certain aspects of the invention, one or more inhibitory agents and MCFD2 molecules are administered to one or more virus particles and reduce infectivity of the virus particles. A reduction may be, in some aspects of the invention, from a level of the virus particles that were not contacted with the inhibitory agent or MCFD2 molecule. In certain aspects of the invention, a level of infectivity may be reduced by at least 1%, 5%, 10%, 20%, 30%, 40%, 50%, 60%, 70%, 80%, 90%, or 100% from the level of infectivity determined in virus particles not contacted with the inhibitory agent and/or MCFD2 molecule of the invention. Similarly, in certain aspects of the invention, one or more inhibitory agents and MCFD2 molecules are administered to a cell and/or subject and reduce the likelihood of infection of the cell and/or subject by a virus. A reduction may be, in some aspects of the invention, from a likelihood of the virus infection in a substantially similar cell or subject not contacted with the inhibitory agent or MCFD2 molecule. In certain aspects of the invention, a likelihood of a virus infection in a cell or subject may be reduced by least 1%, 5%, 10%, 20%, 30%, 40%, 50%, 60%, 70%, 80%, 90%, or 100% from the likelihood of viral infection of the cell and/or subject not contacted with the inhibitory agent and/or MCFD2 molecule of the invention.

Compounds, Molecules, and Methods

The invention in some aspects relates to methods for increasing the level of an inhibitory agent or MCFD2 molecule of the invention in a cell, tissue, and/or subject. In certain aspects of the invention, increasing the level of an inhibitory agent or MCFD2 molecule in a cell increases an activity of the inhibitory agent or MCFD2 molecule in the cell, thereby decreasing infectivity of a virus particle in or on the cell. In some embodiments of the invention, a level of an MCFD2 polypeptide can be increased by increasing expression of the MCFD2 polypeptide. Thus, some embodiments of the invention methods may include increasing the level of an MCFD2 polypeptide-encoding polynucleotide in a cell, tissue, or subject, which results in an increase of one or more of a level and activity of the MCFD2 polypeptide in the cell, tissue, or subject. In certain embodiments of the invention, methods include increasing the level of an MCFD2 polypeptide in a cell, tissue, or subject, by delivering the MCFD2 polypeptide into the cell, tissue or subject, to treat a viral infection in the cell, tissue, or subject. In some embodiments of the invention, the MCFD2 molecule (including: an MCFD2 protein, polypeptide, and/or peptide fragment) is soluble MCFD2, also referred to herein as sMCFD2.

As used herein, the terms "treat", "treated", or "treating" when used with respect to a viral infection may refer to a prophylactic treatment that decreases the likelihood of a subject developing the viral infection, and also may refer to a treatment after the subject has developed the viral infection in order to eliminate or ameliorate the viral infection, prevent the viral infection from becoming more advanced, reduce a level of contagiousness of the viral infection, and/or slow the progression of the viral infection compared to in the absence of the therapy.

In certain embodiments of the invention, contacting a virus particle in or on a cell and/or in a subject with an inhibitor agent and/or MCFD2 molecule of the invention reduces the infectivity of the virus particle in or on the cell and/or in the subject. Examples of inhibitory agents include, but are not limited to an antibody, or functional fragment thereof, a small molecule inhibitor, and an inhibitory polynucleotide. The terms "inhibitory agent", "inhibitory compound", and "inhibitory agent compound" are used interchangeably herein.

In some aspects of the invention, an inhibitory compound of the invention reduces infectivity of a virus particle by binding to a region of an ERGIC-53 polypeptide that comprises the amino acid sequence corresponding to amino acids 47-60 of the sequence set forth as SEQ ID NO: 3.

In certain embodiments of the invention, an inhibitory compound of the invention may reduce infectivity of a virus particle by acting on an ERGIC-53 complex and inhibiting a function of a carbohydrate recognition domain (CRD) of the ERGIC-53 polypeptide of the complex, by inhibiting a function of one or more of: (1) a GPC binding domain of the CRD; (2) a mannose binding domain of the CRD; and (3) an MCFD2 polypeptide binding motif of the CRD.

In some aspects of the invention, an inhibitory compound of the invention may reduce infectivity of a virus particle by inhibiting formation of an MCFD2-ERGIC-53 complex at least in part, by interacting with amino acid residues at the C-terminal end of an MCFD2 polypeptide.

In certain aspects of the invention an inhibitory compound of the invention may reduce infectivity of a virus particle by inhibiting formation of an MCFD2-ERGIC-53 complex by interfering with and reducing an interaction between MCFD2 and ERGIC-53 at one or more of interacting sites: α2, α3 and loops α1-β1, and α3-α4 of MCFD2 and β1a, β1b, (β2, β5, β15, 310-1 and loop β1-β2 of ERGIC-53-CRD. Interactions occur through intermolecular hydrogen bonds formed by residues Asp83, Asp89, Glu114, Asp122, Asn132, and Asp133 of MCFD2, and Arg45, Phe46, Tyr48, Lys53, Gln59, Phe66, and Lys96 of ERGIC-53-CRD. Each of the interacting sites is remote from the sugar-binding site of the CRD. (see structure described in Nishio, M. et al., 2010 Proc Natl Acad Sci March 2; 107(9):4034-9, the content of which is incorporated herein by reference).

In certain aspects of the invention, an inhibitory compound of the invention may reduce infectivity of a virus particle by inhibiting formation of an MDFD2-ERGIC-53 complex by interfering with and reducing an interaction between MCFD2 and ERGIC-53 at one or more of interacting sites: α1, α2, α3 and α4 of MCFD2; and 310-1, loop β10-β12 and loop β12-β13 of ERGIC-53-CRD. Interference occurs through reduction of MCFD2 binding, which is mediated by both hydrogen bonds and van der Waals contacts. Residues involved in the intermolecular formation of hydrogen bonds are Gln73, Thr98, Glu116, Asp128, Phe141, and Lys143 of MCFD2, and Phe198, Tyr199, Phe220, Asp223, and Lys224 of ERGIC-53-CRD. Each of the interacting sites is remote from the sugar-binding site of the CRD. (see structure described in Nishio, M. et al., 2010 Proc Natl Acad Sci March 2; 107(9):4034-9, the content of which is incorporated herein by reference).

In certain aspects of the invention, the inhibitory compound directly binds to at least one of the GPC binding domain, the mannose binding domain, and the MCFD2 polypeptide binding motif and thereby directly inhibits a function of the ERGIC-53 polypeptide. Alternatively, in certain aspects of the invention, the inhibitory agent acts indirectly to inhibit an activity of an ERGIC-53 complex, an example of which, though not intended to be limiting, is an inhibiting compound of the invention allosterically reducing one or more of a level and a function of the ERGIC-53 polypeptide. Non-limiting examples of an inhibitory agent of the invention is an antibody or functional fragment thereof that selectively binds at least one of: an ERGIC-53 polypeptide and a MCFD2 polypeptide; and a glycoprotein that comprise a ERGIC-53/MCFD2/glycoprotein complex; and an antibody or functional fragment thereof that selectively binds at least one of: an ERGIC-53 polypeptide and a MCFD2 polypeptide that comprise a ERGIC-53 complex. In certain aspects of the invention, an inhibitory agent is an antibody or functional fragment thereof that selectively binds an MCFD2-binding site on the ERGIC-53 polypeptide.

Antibodies that may be used in methods of the invention to selectively bind ERGIC-53 polypeptide and inhibit virus infectivity may be prepared using standard methods of antibody production. An isolated ERGIC-53 polypeptide can be used as an immunogen to generate antibodies that selectively bind ERGIC-53 using standard techniques for polyclonal and/or monoclonal antibody preparation. In certain aspects of the invention an ERGIC-53 polypeptide can be used as an antigen to prepare an antibody, or functional fragment thereof that selectively binds ERGIC-53 and inhibits virus infectivity. ERGIC-53 polypeptides that may be useful as antigens to prepare antibodies for use in inhibitory compounds and methods of the invention, may include at least a portion of the amino acid sequence of an ERGIC-53 polypeptide sequence set forth herein as SEQ ID NO: 3. An antigenic peptide of ERGIC-53 may comprise at least 4, 5, 6, 7, or 8 amino acid residues of the amino acid sequence set forth herein as SEQ ID NO: 3 and encompasses an epitope of a ERGIC-53 polypeptide.

In certain aspects of inhibitory agents and methods of the invention, an inhibitory agent comprises an antibody raised against at least a portion of the luminal domain the ERGIC-53. The luminal domain of ERGIC-53 is the region of the ERGIC-53 polypeptide inside secretory pathway organelles. In certain aspects of the invention, an antibody included in a compound and/or method to inhibit virus infectivity is not an antibody that is raised only against an epitope in the cytoplasmic domain (also referred to as the cytosolic domain) of ERGIC-53. For example, in certain aspects of the invention an inhibitory agent of the invention is not an antibody raised only against the amino acid sequence set forth as QQEAAAKKFF (SEQ ID NO: 9), or TVH-FIIFVVVQTVLFIGYIMYRSQQEAAAKKFF (SEQ ID NO: 10), or comprising the KKFF motif, each of which are in the cytoplasmic/cytosolic domain or the transmembrane domain of the ERGIC-53 polypeptide set forth herein as SEQ ID NO: 3. Thus, ERGIC-53 polypeptides useful as antigens to prepare antibodies to for use in certain compounds and methods of the invention to inhibit virus infectivity, may include at least a portion of the amino acid sequence from the N-terminus of an ERGIC-53 polypeptide up to the transmembrane region of the ERGIC-53 sequence, which begins at amino acid residue 478 in the sequence set forth herein as SEQ ID NO: 3. It will be understood that in certain embodiments the invention provides antigenic peptides that include all or fragments of the sequence of amino acid residues 1-477 of SEQ ID NO: 3 for use as immunogens to prepare antibodies. Non-limiting examples of fragments of SEQ ID NO: 11, which includes amino acids 1-477 of SEQ ID NO:3, are set forth herein as SEQ ID NOs: 12-20. It will be understood that other fragments of SEQ ID NOs: 11 and/or 3 may be used to prepare antibodies and that the fragments can be smaller or larger than those set forth as SEQ ID NOs: 12-20. An antigenic peptide of ERGIC-53 may comprise at least 6, 7, or 8 amino acid residues of the amino acid sequence set forth herein as SEQ ID NO: 11 (amino acids 1-477 of SEQ ID NO: 3) and encompasses an epitope of a ERGIC-53 polypeptide. It will be understood that in certain aspects of the invention an antibody that inhibits virus infectivity may be raised against a polypeptide having an amino acid sequence comprising a portion of the cytoplasmic region of ERGIC-53.

In certain aspects of inhibitory agents and methods of the invention, an inhibitory agent that reduces viral infectivity comprises an antibody raised against combination polypeptides that comprise amino acid sequences of both ERGIC-53 and MCFD2, generated from synthetic nucleotides encoding the individual or sequential peptide regions, as one, two, three, or more polypeptides. In certain aspects of the invention, an amino acid linker sequence is present between two or more of the polypeptides in a combination antigen. In some embodiments of the invention, a combination polypeptide that is used to raise antibodies comprises all of, or a fragment, of the amino acid sequence of ERGIC-53 (SEQ ID NO: 3) and all of, or a fragment of, the amino acid sequence of MCFD2 (SEQ ID NO: 1). In some embodiments, the combination polypeptide is an antigenic polypeptide. Non-limiting examples of fragments of SEQ ID NO: 1 and SEQ ID NO: 3 are provided herein. Combination polypeptides that may be used as immunogens to prepare antibodies of the invention ay include, but are not limited to: polypeptides with amino acid sequences that correspond, at least in part, to interacting regions between ERGIC-53's CRD and MCFD2. In some embodiments of the invention, an antibody useful to inhibit infectivity of a virus is a combination antibody raised against a polypeptide comprising an amino acid sequence corresponding at least a portion of one or more of the luminal domain and the cystolic domain of ERGIC-53

In certain aspects of the invention, a combination immunogen may be used to generate antibodies that recognize, bind, and stabilize the complex of ERGIC-53 with MCFD2. Methods of the invention that include antibody stabilization may be used to lock ERGIC-53/MCFD2 in an antiviral state thereby reducing infectivity of the virus. In some aspects of the invention, genetically fusing the two regions assures a 1:1 stable complex. For example, in some aspects of the invention, a single polypeptide that contains amino acid sequences of regions of both ERGIC-53 and MCFD2, separated by a short flexible linker, may contain the information needed to 1) adopt the shape of the individual motifs and then (2) fold into the 3-dimensional complex arrangement seen following ligation of ERGIC-53 with MCFD2, and (3) retain a high local concentration of the complex.

In certain aspects, the invention includes methods of increasing one or more of a level and an activity of an MCFD2 molecule, or functional variant thereof. The level of an MCFD2 molecule or functional variant may be increased by administering an MCFD2 polypeptide or functional variant thereof or by administering an MCFD2-encoding polynucleotide molecule, or a variant thereof to a virus particle. An increase in the actual MCFD2 polypeptide inhibits virus particle infectivity. In some embodiments of the invention, a method may also include administration of a mimetic of an MCFD2 molecule to a virus particle to reduce infectivity of the virus particle. A non-limiting example of a mimetic that may be used in aspects of the invention to increase an activity or function that is performed by an MCFD2 polypeptide is a peptidomimetic, which may be a small protein-like chain that mimics the activity or function of the MCFD2 polypeptide. Thus increasing one or more of the level of an MCFD2 polypeptide or functional fragment thereof, and a mimetic of an MCFD2 polypeptide, may be used in methods of the invention to inhibit virus infectivity and to treat a viral infection in a cell and/or subject.

In some embodiments, methods and compounds of the invention to inhibit infectivity of a virus particle comprise administering a functional fragment of a MCFD2 molecule. A non-limiting example of a functional fragment is a fragment of an MCFD2 polypeptide that comprises MCFD2 EF-hand residues D89 and D129. Such a fragment is a functional fragment in that it retains the activity of the MCFE2 polypeptide to inhibit virus infectivity.

An MCFD2 polypeptide, functional variant thereof, or a mimetic thereof may be administered to a virus particle and reduce infectivity of the virus particle by directly or indirectly modulating lectin activity of an ERGIC-53 polypeptide of a virus particle. The modulation may be allosteric modulation. A non-limiting example of a MCFD2 polypeptide that may be administered to a virus particle is an MCFD2 polypeptide, which comprises a full-length polypeptide set forth herein as SEQ ID NO: 1 or a functional variant or fragment thereof. In certain aspects of the invention, a functional variant of an MCFD2 polypeptide or variant thereof that may be used in methods of the invention comprises an MCFD2 polypeptide or variant thereof that is O-glycosylated. An MCFD2 polypeptide or variant thereof administered to a virus particle may be a soluble MCFD2 polypeptide or variant thereof. Some aspects of the invention include administration of a polynucleotide that encodes an MCFD2 polypeptide or variant thereof. Expression of the MCFD2 polypeptide or variant thereof from its encoding polynucleotide can be used in certain aspects of the invention to increase the level of the MCFD2 polypeptide or variant thereof, and inhibit virus infectivity.

MCFD2 molecules of the invention include MCFD2 polypeptides or polynucleotides that encode MCFD2 polypeptides. A non-limiting example of a MCFD2 polypeptide of the invention is SEQ ID NO: 1. One of ordinary skill in the art will understand how to prepare additional MCFD2 polypeptides that are fragments of SEQ ID NO:1 for use in methods of the invention. Non-limiting examples of an MCFD2 polypeptide fragment are set forth as SEQ ID NOs: 5, 6, 7, 8, and 9, each of which is a MCFD2 polypeptide that is a fragment of SEQ ID NO:1. It will be understood that in some embodiments of the invention, a fragment of a full-length MCFD2 polypeptide may have an amino acid sequence that corresponds to the amino acid sequence set forth as SEQ ID NO:1 or a variant thereof, but without 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more amino acids corresponding to the full-length MCFD2 polypeptide sequence set forth as SEQ ID NO:1. Such polypeptides are readily envisioned by one of ordinary skill in the art. In addition, in certain aspects of the invention a MCFD2 polypeptide may comprise a sequence set forth as SEQ ID NO:1 or a fragment thereof, and include additional amino acids, for example through not intended to be limiting, one or more additional amino acids at their C terminus and/or N terminus that are not present in SEQ ID NO: 1 or a fragment thereof. MCFD2 polypeptides that are fragments of a full-length MCFD2 (for example a fragment of SEQ ID NO:1) can be used in embodiments of treatment methods of the invention.

In certain aspects of the invention, an MCFD2 compound and an inhibitory compound of the invention includes one or more of: an MCFD2 polypeptide, MCFD2-encoding polynucleotide, an MCFD2 mimetic, and an inhibitory agent and may also include one or more targeting and delivery agents. Non-limiting examples of targeting and delivery agents are: a small molecule, a polynucleotide, a liposome, a PEGylated liposome, a biodegradable polymer, a nanoparticle, an oligonucleotide, and a polypeptide. In certain embodiments of the invention a targeting agent assists in one or more of: directing an MCFD2 compound, mimetic compound, or inhibitory compound of the invention to a specific cell or tissues, internalization of the MCFD2 molecule, mimetic, or inhibitory agent into a cell, etc. A skilled artisan can prepare and utilize variant targeting agents using standard methods.

A variant polypeptide (also referred to herein as a "modified" polypeptide) may include deletions, point mutations, truncations, amino acid substitutions and/or additions of amino acids or non-amino acid moieties. Modifications of a polypeptide of the invention may be made by modification of the nucleic acid sequence that encodes the polypeptide or alternatively, modifications may be made directly to the polypeptide, such as by cleavage, addition of a linker molecule, addition of a detectable moiety, such as a fluorescent label, and the like. Modifications also embrace fusion proteins comprising all or part of the polypeptide's amino acid sequence. In certain embodiments of the invention, a modification of a polypeptide may be O-glycosylation of the polypeptide. In a non-limiting example, an MCFD2 polypeptide variant may be an MCFD2 polypeptide or variant thereof that is O-glycosylated. An O-glycosylated polypeptide is a polypeptide to which a sugar molecule is attached to an oxygen atom of an amino acid residue of the polypeptide. An O-glycosylated polypeptide may be sugar molecules attached to oxygen atoms of 1, 2, 3, 4, 5, 6, or more amino acids of the polypeptide.

It will be understood that contacting a virus particle with a polypeptide, mimetic, antibody or functional fragment thereof, inhibitory agent, etc. in a method of the invention can comprise administration of the polypeptide, mimetic, antibody or functional fragment thereof, inhibitory agent, etc., and its delivery into the bloodstream of a subject, where the polypeptide, mimetic, antibody or functional fragment thereof, inhibitory agent, etc. interacts with the virus particle. In some aspects of the invention, a polypeptide, mimetic, antibody or functional fragment thereof, inhibitory agent, etc. is modified to increase its stability, half-life, efficacy etc. in a subject. Modifications can include one or more of: addition of, attachment to, and inclusion of an agent or a component that increases stability, efficacy, half-life, etc. of the polypeptide, antibody or functional fragment thereof, inhibitory agent, etc. that is administered to a subject. Methods to stabilize polypeptides, mimetics, antibodies or functional fragments thereof, inhibitory agents, etc., for use in treatment methods and therapies are known and used in the art and can be used in certain in embodiments of the invention. Such modifications can be included to increase stability of, and/or reduce clearance of, a polypeptide, mimetic, antibody or functional fragment thereof, inhibitory agent from the bloodstream or other tissue of a subject.

In some embodiments, a polypeptide, mimetic, antibody or functional fragment thereof, inhibitory agent used in a treatment method of the invention is included in a compound or composition. A compound or composition comprising a polypeptide, mimetic, antibody or functional fragment thereof, inhibitory agent for administration or delivery to a subject may comprises an agent for one or more of: increasing stability, increasing half-life, increasing efficacy, and decreasing clearance of the polypeptide, mimetic, antibody or functional fragment thereof, inhibitory agent etc. Non-limiting examples of such agents that can be included in certain embodiments of compounds or compositions of the invention are known in the art and include, carbohydrates, lipids, microspheres, nanoparticles, polyethylene glycol, polymers, biodegradable particles, etc. In addition, it is known in the art that the inclusion of non-natural amino acids in a polypeptide can stabilize a polypeptide and increase its resistance to protease activity. The inclusion of non-natural amino acids in therapeutic polypeptides and proteins can be used in some embodiments of methods of the invention comprising administering a polypeptide or protein to a subject. Methods to stabilize peptides and therapeutic agents to increase efficacy, half-life, stability, etc. following administration to a subject are well known, see for example: Pisal, D., et al., J. Pharm Sci: 2010 June 99(6):2557-2575, the content of which is incorporated herein by reference in its entirety.

In certain aspects of the invention contacting a virus particle with a polypeptide, mimetic, antibody or functional fragment thereof, inhibitory agent, etc. comprises delivery of the polypeptide mimetic, antibody or functional fragment thereof, inhibitory agent etc. into a cell of a subject. It will be understood that methods for delivery into a cell may comprise use of delivery agents, such as cell-penetrating peptides, carriers, nanoparticles, targeting molecules, etc. Methods of using such agents in the therapeutic arts are well known and can be used in embodiments of methods of the invention.

In certain embodiments of the invention, a polypeptide variant may be a polypeptide that is modified specifically to alter a feature of the polypeptide unrelated to its physiological activity. For example, though not intended to be limiting, one or more amino acid residues may be added at the N or C-terminus of a MCFD2 polypeptide to increase stability and/or increase delivery efficiency. Polypeptides suitable for use in methods of the invention can be synthesized with modifications and/or modifications can be made in a polypeptide by selecting and introducing an amino acid substitution, deletion, or addition. Modified polypeptides then can be tested for one or more activities (e.g., increased delivery, increased stability, inhibition of a virus particle infectivity, etc.) to determine which modification provides a modified polypeptide with the desired properties.

The skilled artisan will also realize that conservative amino acid substitutions may be made in a polypeptide to provide functionally equivalent polypeptides, i.e., a modified MCFD2 polypeptide, MCFD2 mimetic, ERGIC-53 polypeptide, or inhibitory agent that retains a functional capability of the un-modified polypeptide, mimetic, or agent, respectively. As used herein, a "conservative amino acid substitution" refers to an amino acid substitution that does not alter the relative charge or size characteristics of the polypeptide in which the amino acid substitution is made. Conservative substitutions of amino acids may, in some embodiments of the invention, include substitutions made amongst amino acids within the following groups: (a) M, I, L, V; (b) F, Y, W; (c) K, R, H; (d) A, G; (e) S, T; (f) Q, N; and (g) E, D. Polypeptide variants can be prepared according to methods for altering polypeptide sequence and known to one of ordinary skill in the art such. Non-limiting examples of functionally equivalent polypeptide variants are MCFD2 polypeptides, MCFD2 mimetics, ERGIC-53 polypeptides, and inhibitory agents with conservative amino acid substitutions of the MCFD2 polypeptide, MCFD2 mimetic, ERGIC-53 polypeptide, and inhibitory agent, respectively. As used herein, the term "variant" when used in relation to a MCFD2 polypeptide, MCFD2 mimetic, ERGIC-53 polypeptide, and inhibitory agent may mean a fragment of the MCFD2 polypeptide, MCFD2 mimetic, ERGIC-53 polypeptide, and inhibitory agent. In certain embodiments of the invention, an MCFD2 polypeptide variant comprises a fragment of the amino acid sequence of an MCFD2 polypeptide and the fragment has at least 75%, 80%, 85%, 90%, 95%, 97%, 98%, 99%, or 100% sequence identity to the region of the amino acid sequence of the MCFD2 polypeptide with which it aligns. Similarly, in some aspects of the invention, a variant of a MCFD2 polypeptide mimetic, an ERGIC-53 polypeptide, and a peptide inhibitory agent comprises a fragment of the amino acid sequence of the MCFD2 polypeptide mimetic, the ERGIC-53 polypeptide, and the peptide inhibitory agent, respectively and the fragment has at least 75%, 80%, 85%, 90%, 95%, 97%, 98%, 99%, or 100% sequence identity to the region of the amino acid sequence of the MCFD2 polypeptide mimetic, the ERGIC-53 polypeptide, and the peptide inhibitory agent with which it aligns. MCFD2 polypeptides and ERGIC-53 polypeptides of the invention may be shorter or longer than MCFD2 polypeptide sequences and ERGIC-53 polypeptide sequences, respectively, set forth herein. In addition, nucleic acids of the invention may be used to obtain additional coding regions, and thus additional polypeptide sequences, using techniques known in the art.

As used herein the term "modified" or "modification" may be used to describe a sequence difference between a polypeptide or polynucleotide sequence and that of that sequence. In some aspects of the invention, a modification of a polynucleotide or polypeptide may be a change of one, two, three, four, five, six, or more nucleic acids or amino acids, respectively, in the sequence as compared to the corresponding unmodified sequence. For example, though not intended to be limiting, the amino acid sequence of a modified MCFD2 polypeptide, MCFD2 polypeptide mimetic, ERGIC-53 polypeptide, or peptide inhibitory agent may be identical to that of its originating MCFD2 polypeptide, MCFD2 polypeptide mimetic, ERGIC-53 polypeptide, or peptide inhibitory agent except that the modified or variant has one, two, three, four, five, or more amino acid substitutions, deletions, insertions, or combinations thereof, and thus is a variant of the originating sequence.

The invention, in some aspects, includes polypeptides having one or more substitutions or other modifications from those described herein. For example, though not intended to be limiting, a sequence of a MCFD2 polypeptide, MCFD2 polypeptide mimetic, ERGIC-53 polypeptide, or peptide inhibitory agent can be modified with one or more substitutions, deletions, insertions, or other modifications and can be tested using methods described herein for characteristics including, but not limited to: expression; cell localization; binding, efficacy in inhibiting infectivity of a virus particle, increasing treatment of a virus infection in a cell or subject, etc. MCFD2 molecules, MCFD2 mimetic molecules, ERGIC-53 molecules, and peptide inhibitory agent molecules of the present invention include polypeptide and nucleic acid sequences provided herein and variants that have at least about 75%, 80%, 85%, 90%, 95%, 96%, 97%, 98%, or 99% identity to an amino acid or nucleic acid sequence of the MCFD2 molecule, MCFD2 polypeptide mimetic molecule, ERGIC-53 molecule, or peptide inhibitory agent molecule, respectively. It will be understood that a polynucleotide that encodes an MCFD2 polypeptide or ERGIC-53 polypeptide of the invention may comprise a nucleic acid sequence that has least 75%, 80%, 85%, 90%, 95%, 96%, 97%, 98%, or 99% identity to a nucleic acid sequence encoding the polypeptide sequence described herein.

Sequence identity can be determined using standard techniques known in the art. To determine the percent identity (similarity) of two amino acid sequences the sequences are aligned for optimal comparison purposes (e.g., gaps may be introduced in the sequence of one protein for optimal alignment with the other protein). The amino acid residues at corresponding amino acid positions are then compared. When a position in one sequence is occupied by the same amino acid residue as the corresponding position in the other sequence, then the molecules have identity/similarity at that position. The percent identity or percent similarity between the two sequences is a function of the number of identical positions shared by the sequences (i.e., % identity or % similarity=number of identical positions/total number of positions×100). Such an alignment can be performed using any one of a number of well-known computer algorithms designed and used in the art for such a purpose. Similarly, percent identity/similarity of polynucleotide sequences encoding a polypeptide of the invention can be determined using art-known alignment and comparison methods for nucleic acids.

Modified sequences, (which are also referred to herein as variants) may in some embodiments be prepared by site specific mutagenesis of nucleic acids in the DNA encoding a polypeptide of the invention, using cassette or PCR mutagenesis or other techniques known in the art, to produce DNA encoding the polypeptide, and thereafter expressing the DNA in cell culture. Where amino acid substitutions are made to a small fragment of a polypeptide, the substitutions can be made by directly synthesizing the polypeptide. In certain embodiments of the invention, activity of variant or fragment of a polypeptide can be tested by cloning the gene encoding the altered polypeptide into a bacterial or mammalian expression vector, introducing the vector into an appropriate host cell, expressing the altered polypeptide, and testing for a functional capability of the polypeptide as disclosed herein. Additional methods for generating recombinant polypeptides are known in the art may include use of prokaryotic and eukaryotic expression systems including but not limited to bacterial and mammalian expression systems.

Amino acid substitutions are typically of single residues and in certain embodiments of the invention, 1, 2, 3, 4, 5, 6, 7, 8, 9, 10, 11, 12, 13, 14, 15, 16, 17, 18, 19, 20 or more substitutions can be made in the amino acid sequence of an MCFD2 molecule, MCFD2 mimetic molecule, ERGIC-53 molecule, or peptide inhibitory agent of the invention. Amino acid insertions are also envisioned, and in certain aspects of the invention, compounds of the invention may include insertion of 1, 2, 3, 4, 5, 6, 7, 8, 9, 10, 11, 12, 13, 14, 15, 16, 17, 18, 19, or 20 amino acids, although larger insertions may be tolerated. Compounds of the invention may also include MCFD2 molecules, MCFD2 mimetic molecule, ERGIC-53 molecules, and/or peptide inhibitory agents may that include deletions 1, 2, 3, 4, 5, 6, 7, 8, 9, 10, 11, 12, 13, 14, or 15 amino acids, although larger deletions may be tolerated. Substitutions, deletions, insertions or any combination thereof may be used to arrive at a final modified MCFD2 molecule, MCFD2 mimetic molecule, ERGIC-53 molecule, and peptide inhibitory agent. A modified MCFD2 molecule, MCFD2 mimetic molecule, and/or peptide inhibitory agent may be a component of a MCFD2 compound, MCFD2 mimetic compound, and inhibitory compound of the invention. Generally these changes are done on a few amino acids to minimize the alteration of the molecule. However, larger changes may be tolerated in certain circumstances. A modified polypeptide of the invention may, in some embodiments, incorporate unnatural amino acids as well as natural amino acids. An unnatural amino acid can be included in a polypeptide of the invention to enhance a characteristic such as targeting, delivery, function, stability, or to lower toxicity, etc.

A virus particle inhibitory compound of the invention that may be used in a treatment method of the invention may include a MCFD2 molecule or functional variant thereof, a MCFD2 peptide mimetic or functional variant thereof, or a peptide inhibitory agent as described herein, or a functional variant thereof. Also included in some aspects of the invention are ERGIC-53 molecules or functional variants thereof. The term "variant" as used herein, describes a molecule with one or more of the following characteristics: (1) the variant differs in sequence from the molecule of which it is a variant, (2) the variant is a fragment of the molecule of which it is a variant and is identical in sequence to the fragment of which it is a variant, and/or (3) the variant is a fragment and differs in sequence from the fragment of the molecule of which it is a variant.

In certain aspects of the invention, a functional variant of a polynucleotide molecule or agent has at least 85%, 90%, 95%, 97%, 98%, 99%, or 100% nucleic acid sequence identity to the polynucleotide sequence of which it is a variant. As described elsewhere herein a functional variant of the polynucleotide sequence of a MCFD2 molecule, a MCFD2 peptide mimetic, an ERGIC-53 molecule, or a peptide inhibitory agent may be a functional fragment of the polynucleotide sequence, respectively. In some aspects of the invention, a functional variant of a polynucleotide comprises a fragment of the nucleic acid sequence of the polynucleotide and the fragment has at least 85%, 90%, 95%, 97%, 98%, 99%, or 100% sequence identity to the region of the nucleic acid sequence of the polynucleotide with which it aligns. In certain aspects of the invention, a functional variant of a polypeptide has at least 85%, 90%, 95%, 97%, 98%, 99%, or 100% sequence identity to the amino acid sequence of the polypeptide of which it is a variant. In certain instances when a functional variant of the polypeptide comprises a fragment of the amino acid sequence of the polypeptide, the functional variant of the polypeptide may comprise a fragment of the amino acid sequence of the polypeptide and the fragment has at least 85%, 90%, 95%, 97%, 98%, 99%, or 100% amino acid sequence identity to the region of the polypeptide's amino acid sequence with which it aligns.

Treatments and Methods

The term "virus particle inhibitory compounds" as used herein in reference to inhibiting virus particle infectivity, include compounds comprising one or more of: an MCFD2 polypeptide or functional variant thereof; a polynucleotide that encodes an MCFD2 polypeptide or variant thereof, an MCFD2 mimetic molecule, and an inhibitory agent of the invention. A virus particle inhibitory compound of the invention may be administered in an effective amount to virus particle, cell, and/or subject in need of treatment of a virus as described herein. Methods of the invention in some embodiments include administering to a cell and/or subject a virus particle inhibitory compound of the invention that inhibits infectivity of a virus and treats the virus infection in the cell or subject.

As used herein, the terms "protein" and "polypeptide" are used interchangeably and thus the term polypeptide may be used to refer to a full-length protein and may also be used to refer to a fragment of a full-length protein. As used herein, the terms "polynucleotide" and "nucleic acid sequence" may be used interchangeably and may comprise genetic material including, but not limited to: RNA, DNA, mRNA, cDNA, etc., which may include full length sequences and/or fragments thereof. As used herein the terms: "MCFD2 polypeptide" and "ERGIC-53 polypeptide" and their encoding polynucleotides, respectively, will be understood to refer at least to MCFD2 and ERGIC-53 sequences disclosed herein and variants of such sequences.

According to some aspects of the invention, one or more virus particle inhibitory compounds may be administered in methods of the invention. In some embodiments of the invention, a level or function of an MCFD2 and/or an ERGIC-53 polypeptide may be modulated by genetically introducing a virus particle inhibitory compound into a cell and/or subject, and reagents and methods are provided for genetically targeted expression of MCFD2 polypeptides and variants thereof, MCFD2 peptide mimetics, and peptide inhibitory agents. Genetic targeting can be used to deliver one or more MCFD2 polypeptides or variants thereof, MCFD2 peptide mimetics, and peptide inhibitory agents to specific cell types, to specific cell subtypes, to specific spatial regions within an organism, or to specific regions within a cell. Genetic targeting also relates to the control of the amount of an MCFD2 polypeptide or variant thereof, MCFD2 peptide mimetic, and peptide inhibitory agent expressed, and the timing of the expression. Some embodiments of the invention include a reagent for genetically targeted expression of MCFD2 polypeptides and variants thereof, MCFD2 peptide mimetics, and peptide inhibitory agents, wherein the reagent comprises a vector that contains a nucleic acid that encodes an MCFD2 polypeptide or variant thereof, an MCFD2 peptide mimetic, and/or a peptide inhibitory agent.

As used herein, the term "vector" refers to a polynucleotide molecule capable of transporting between different genetic environments another nucleic acid to which it has been operatively linked. The term "vector" also refers to a virus or organism that is capable of transporting the nucleic acid molecule. One type of vector is an episome, i.e., a nucleic acid molecule capable of extra-chromosomal replication. Some useful vectors are those capable of autonomous replication and/or expression of nucleic acids to which they are linked. Vectors capable of directing the expression of genes to which they are operatively linked are referred to herein as "expression vectors". Other useful vectors, include, but are not limited to viruses such as lentiviruses, retroviruses, adenoviruses, and phages. Vectors useful in some methods of the invention can genetically insert one or more of a MCFD2 polypeptide or variant thereof, a MCFD2 peptide mimetic, and a peptide inhibitory agent into dividing and non-dividing cells and can insert one or more MCFD2 polypeptides or variants thereof, MCFD2 peptide mimetics, and peptide inhibitory agents to cells that are in vivo, in vitro, or ex vivo cells.

Vectors useful in methods of the invention may include additional sequences including, but not limited to one or more signal sequences and/or promoter sequences, or a combination thereof. Expression vectors and methods of their use are well known in the art. In certain embodiments of the invention, a vector may be a lentivirus comprising a nucleic acid or gene that encodes a MCFD2 polypeptide or variant thereof, a MCFD2 peptide mimetic, or a peptide inhibitory agent of the invention or a variant thereof. A lentivirus is a non-limiting example of a vector that may be used to create stable cell line. The term "cell line" as used herein is an established cell culture that will continue to proliferate given the appropriate medium.

Promoters that may be used in methods and vectors of the invention include, but are not limited to, cell-specific promoters or general promoters. Methods for selecting and using cell-specific promoters and general promoters are well known in the art. A non-limiting example of a general purpose promoter that allows expression of a MCFD2 polypeptide or variant thereof, a MCFD2 peptide mimetic, or a peptide inhibitory agent in a wide variety of cell types—thus a promoter for a gene that is widely expressed in a variety of cell types, for example a "housekeeping gene" can be used to express a MCFD2 polypeptide or variant thereof, a MCFD2 peptide mimetic, or peptide inhibitory agent in a variety of cell types.

Additional compounds that may be administered in treatment methods of the invention include small molecule or chemical inhibitory agents or MCFD2 mimetics that inhibit viral infectivity. Methods of identifying and testing such small molecules and chemicals may include use of art-known library screening and testing procedures in conjunction with the teaching provided herein.

Administration Strategies

Virus particle inhibitory compounds of the invention may be administered singly or in combination with one or more additional compounds. In some embodiments, a virus particle inhibitory compound of the invention may act in a synergistic manner with one or more additional therapeutic agents or treatments for a viral infection thereby increasing the effectiveness of the one or more therapeutic agents or activities.

It will be understood that additional virus particle inhibitory compounds can be identified and used in methods of the invention. For example, assays and methods presented herein can be used to assess candidate compounds for their ability to inhibit virus particle infectivity and/or their ability to treat a viral infection when administered to a cell and/or subject. Virus particle inhibitory compounds of the invention described herein can be used alone or in conjunction with other molecules such as targeting agents, labeling agents, additional anti-viral therapeutic agents etc. in treatment methods of the invention.

A targeting agent used in methods and as part of a virus particle inhibitory compound of the invention, of choice will depend upon the nature of the virus, its mode of infection, tissue localization etc. Although not intended to be limiting, in some instances it may be desirable to target a virus particle inhibitory compound of the invention to one or more of a lung cell, a circulatory cell, an organ, an epithelial cell, an endothelial cell, a neuronal cell, a glandular cell, a renal cell, a hematopoietic cell, a lymphoid cell, a cardiac cell, a hepatic cell. Those of ordinary skill in the art will be aware of and will be able to select and use suitable targeting agents in embodiments of the invention using routine methods.

Labeling agents may be used in certain embodiments of methods and compounds of the invention to determine the location of a virus particle inhibitory compound in cells and tissues and also, may be used to assess the cell, tissue, or organelle location of treatment compounds that have been administered. Procedures for attaching and utilizing labeling agents such as enzymatic labels, dyes, radiolabels, fluorescent labels, etc. are well known in the art.

Compositions, compounds, and methods of the invention may be enhanced by utilization in combination with other procedures for treating a viral infection. In some instances a treatment procedure may involve administration of another therapeutic agent or treatment such a medicament and/or surgery, radiation therapy, etc. Thus, in some embodiments of the invention, administration of a virus particle inhibitory compound of the invention may be performed at one or more of: prior to, coincident with, or after administration of another therapy for treating a viral infection. Treatment methods of the invention that include administration of a virus particle inhibitory compound can be used at one or more stages of a viral infection such as pre-exposure to a virus, pre-infection, at the initial infection stage, mid-infection stage, late infection stage, and/or at a post-viral-infection stage. Methods of the invention may also be used for subjects who have previously been treated with one or more other anti-viral medicament, supportive therapies, or other methods that were not successful, were minimally successful, and/or are no longer successful at slowing or stopping progression of the viral infection in the subject.

Effective Amounts

Virus particle inhibitory compounds of the invention may be administered to a virus particle, a cell/and or a subject in an effective amount for treating a viral infection. An "effective amount for treating a viral infection" is an amount necessary or sufficient to realize a desired biologic effect. For example, an effective amount of a virus particle inhibitory compound of the invention could be that amount necessary to do one or more of (i) slowing or halting progression of the virus; (ii) preventing infection of a subject or cell with the virus; or (iii) reversing one or more symptoms of infection by the virus. According to some aspects of the invention, an effective amount is that amount of a virus particle inhibitory compound of the invention alone or in combination with another medicament or treatment, which when combined or co-administered or administered alone, results in a desired therapeutic response, either in the prevention or the treatment of the viral infection. In some aspects of the invention, a desired biological effect may be one or more of: the amelioration and or absolute elimination of symptoms resulting from the viral infection; the complete abrogation of the viral infection, as evidenced for example, by a diagnostic test that indicates the subject is free of the viral infection, or that one or more of the presence, level of virus particle infectivity is reduced, and the severity of the viral infection is reduced.

Typically an effective amount of a virus particle inhibitory compound will be determined in clinical trials, establishing an effective dose for a test population versus a control population in a blind study. In some embodiments, an effective amount will be that which results in one or more of a desired response, such as an amount that: inhibits infectivity of a virus particle, decreases viral infection in a cell and/or subject, or prevents or reduces an infection of a cell and/or subject by a virus. Thus, an effective amount to treat a viral infection may be the amount that when administered inhibits infectivity of the virus particle to a level of infectivity that is lower than the level of infectivity that would occur in the subject or cell without the administration of the virus particle inhibitory compound. In the case of treating a viral infection, a desired response to a treatment of the invention may be reducing or eliminating one or more symptoms or physiological characteristics of the viral infection in a cell, tissue, and/or subject. The reduction or elimination may be temporary or may be permanent. The status of the viral infection can be monitored using art-known methods. In some aspects of the invention, a desired response to treatment of a viral infection may comprise delaying or preventing onset of the viral infection, slowing, delaying, or stopping viral infection's progression, reducing the severity of a viral infection, etc.

An effective amount of a virus particle inhibitory compound of the invention may also be determined by assessing physiological effects of administration of the virus particle inhibitory compound on a cell or subject, such as a decrease in occurrence of a viral infection, a decrease in infectivity of a virus particle, a reduction in contagiousness of a subject with respect to the virus, etc. following administration. As herein the term "administrating" when used in reference to treating one or more virus particles and/or cells with a virus particle inhibitory compound of the invention, includes contacting the virus particle and/or cell with the virus particle inhibitory compound. Similarly, in some embodiments of treatment methods of the invention, administrating a virus particle inhibitory compound to a subject comprises contacting one or more cells of the subject with the administered virus particle inhibitory compound. In certain embodiments of the invention, a virus particle inhibitory compound of the invention is part of a pharmaceutical composition. A virus particle inhibitory compound of the invention may be administered as part of a pharmaceutical composition, wherein the manner of administration is suitable to contact one or more cells with the virus particle inhibitory compound. A pharmaceutical composition of the invention that includes a virus particle inhibitory compound of the invention may also include a pharmaceutically acceptable carrier.

Assays suitable to determine efficacy of a virus particle inhibitory compound of the invention will be known to those skilled in the art and can be employed for measuring the level of the response to a treatment and an amount of a virus particle inhibitory compound administered to a subject can be modified based, at least in part, on such measurements. Non-limiting examples of measurements of response to a virus treatment of the invention include virus diagnostic testing, etc. The amount of a virus particle inhibitory compound administered may be varied for example by one or more of: increasing or decreasing the amount of a pharmaceutical composition administered, changing the pharmaceutical composition administered, changing the route of administration, changing the dosage timing, changing administration of another therapeutic agent, and so on. An effective amount may vary with the particular virus being treated, the age and physical condition of the subject being treated; the stage and severity of the virus, the duration of the treatment, the nature of a prior, concurrent, or impending therapy (if any), the specific route of administration, and additional factors within the knowledge and expertise of the health practitioner.

An effective amount of one or more of a virus particle inhibitory compound of the invention for treatment of a virus may vary depending upon the specific compound or molecule, the mode of delivery of the compound or molecule, and whether it is used alone or in combination with another therapeutic agent or compound. The effective amount for any particular application can also vary depending on such factors as the virus being treated, the particular compound being administered, the size of the subject, or the severity of virus. A skilled artisan can empirically determine the effective amount of a particular compound of the invention without necessitating undue experimentation. Combined with the teachings provided herein, by choosing among the various active virus particle inhibitory compounds and weighing factors such as potency, relative bioavailability, patient body weight, severity of adverse side-effects and preferred mode of administration, an effective prophylactic or therapeutic treatment regimen can be planned that does not cause substantial toxicity and yet is entirely effective to treat a virus in a particular subject.

A pharmaceutical composition dosage and/or dosage of a virus particle inhibitory compound may be adjusted by an individual health care provider or veterinarian, particularly in the event of any complication. A therapeutically effective amount typically varies from 0.01 mg/kg to about 1000 mg/kg, from about 0.1 mg/kg to about 200 mg/kg, or from about 0.2 mg/kg to about 20 mg/kg, in one or more dose administrations daily, for one or more days. The absolute amount will depend upon a variety of factors including a concurrent treatment, the number of doses and the individual subject parameters including age, physical condition, size and weight. These are factors well known to those of ordinary skill in the art and can be addressed with no more than routine experimentation. In some embodiments, a maximum dose can be used, that is, the highest safe dose according to sound medical judgment.

Multiple doses of compounds of the invention are also contemplated. In some instances, a virus particle inhibitory compound of the invention can be administered at least daily, every other day, weekly, every other week, monthly, etc. Doses may be administered once per day or more than once per day, for example, 2, 3, 4, 5, or more times in one 24 hour period.

Pharmaceutical compositions of the invention may be administered alone, in combination with each other, and/or in combination with other drug therapies, or other treatment regimens that are administered to subjects with a virus infection or suspected having a virus infection, or at risk of having a viral infection. Pharmaceutical compositions used in the embodiments of the invention preferably are sterile and contain an effective amount of a virus particle inhibitory compound to do one or more of (1) decrease infectivity of a virus particle, (2) reduce the likelihood of infection of a cell and/or subject with a virus, (3) reduce or eliminate a viral infection in a cell and/or subject, and (4) produce the desired therapeutic response in a unit of weight or volume suitable for administration to a subject.

The doses of a pharmaceutical composition and/or a virus particle inhibitory compound of the invention to treat a virus that is administered to a subject can be chosen in accordance with different parameters, in particular in accordance with the mode of administration used and the state of the subject. Other factors may include the desired period of treatment. In the event that a response in a subject is insufficient at the initial doses applied, higher doses (or effectively higher doses by a different, more localized delivery route) may be employed to the extent that patient tolerance permits.

Administration Methods

A variety of administration routes for a virus particle inhibitory compound of the invention are available. The particular delivery mode selected will depend upon the particular condition being treated and the dosage required for therapeutic efficacy. Methods of this invention, generally speaking, may be practiced using any mode of administration that is medically acceptable, meaning any mode that produces effective levels of treatment without causing clinically unacceptable adverse effects. In some embodiments of the invention, a virus particle inhibitory compound of the invention may be administered via an oral, enteral, mucosal, percutaneous, and/or parenteral route. The term "parenteral" includes subcutaneous, intravenous, intramuscular, intraperitoneal, and intrasternal injection, or infusion techniques. Other routes include but are not limited to nasal (e.g., via inhalation or a gastro-nasal tube), dermal, vaginal, rectal, and sublingual. Delivery routes of the invention may include intrathecal, intraventricular, or intracranial. In some embodiments of the invention, a virus particle inhibitory compound of the invention may be placed within a slow release matrix and administered by placement of the matrix in the subject. In some aspects of the invention, a virus particle inhibitory compound may be administered to a cell and/or subject using nanoparticles coated with a delivery agent.

A virus particle inhibitory compound of the invention may be administered in formulations, which may be administered in pharmaceutically acceptable solutions, which may routinely contain pharmaceutically acceptable concentrations of salt, buffering agents, preservatives, compatible carriers, adjuvants, and optionally other therapeutic ingredients. According to methods of the invention, the compound may be administered in a pharmaceutical composition. In general, a pharmaceutical composition comprises the compound of the invention and a pharmaceutically-acceptable carrier. Pharmaceutically acceptable carriers are well known to the skilled artisan and may be selected and utilized using routine methods. As used herein, a pharmaceutically-acceptable carrier means a nontoxic material that does not interfere with the effectiveness of the biological activity of the active ingredients, e.g., the ability of the virus particle inhibitory compound of the invention to decrease infectivity of a virus particle and to treat the virus infection in a cell and/or subject.

Pharmaceutically acceptable carriers may include diluents, fillers, salts, buffers, stabilizers, solubilizers and other materials that are well-known in the art. Exemplary pharmaceutically acceptable carriers are described in U.S. Pat. No. 5,211,657 and others are known by those skilled in the art. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

In some embodiments of the invention, a virus particle inhibitory compound of the invention may be administered directly to a tissue. In some embodiments, the tissue to which the compound is administered is a tissue in which virus particles are present and/or are likely to be present or to arise. For example, though not intended to be limiting, direct administration to lung or other tissue may be utilized by direct injection, inhalation, or other suitable art-known means. A virus particle inhibitory compound of the invention may be administered once, or alternatively may be administered in a plurality of administrations. If administered multiple times, a virus particle inhibitory compound may be administered via different routes. For example, the first (or the first few) administrations may be made directly into the affected tissue while later administrations may be systemic.

A virus particle inhibitory compound of the invention, when it is desirable to have it administered systemically, may be formulated for parenteral administration by injection, e.g., by bolus injection or continuous infusion. Formulations for injection may be presented in unit dosage form, e.g., in ampoules or in multi-dose containers, with or without an added preservative. The pharmaceutical compositions may take such forms as suspensions, solutions or emulsions in oily or aqueous vehicles, and may contain formulatory agents such as suspending, stabilizing and/or dispersing agents.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day may be used as needed to achieve appropriate systemic or local levels of one or more virus particle inhibitory compounds.

In yet other embodiments, a delivery vehicle is a biocompatible microparticle or implant that is suitable for implantation into the mammalian recipient. Exemplary bioerodible implants that are useful in accordance with this method are described in PCT Publication No. WO 95/24929 (incorporated by reference herein), which describes a biocompatible, biodegradable polymeric matrix for containing a biological macromolecule. Such delivery means are well known in the art and can be used to achieve sustained release of a compound of the invention in a subject, and may be selected not to degrade, but rather, to release by diffusion over an extended period of time.

Both non-biodegradable and biodegradable polymeric matrices can be used to deliver one or more virus particle inhibitory compounds of the invention to a cell and/or subject. In some embodiments, a matrix may be biodegradable. Matrix polymers may be natural or synthetic polymers. A polymer can be selected based on the period of time over which release is desired, generally in the order of a few hours to a year or longer. Typically, release over a period ranging from between a few hours and three to twelve months can be used. The polymer optionally is in the form of a hydrogel that can absorb up to about 90% of its weight in water and further, optionally is cross-linked with multivalent ions or other polymers.

In certain embodiments of the invention, a virus particle inhibitory compound of the invention may be delivered using the bioerodible implant by way of diffusion, or by degradation of the polymeric matrix. Exemplary synthetic polymers for such use are well known in the art. Biodegradable polymers and non-biodegradable polymers can be used for delivery of one or more virus particle inhibitory compounds of the invention using art-known methods. Bioadhesive polymers such as bioerodible hydrogels (see H. S. Sawhney, C. P. Pathak and J. A. Hubell in Macromolecules, 1993, 26, 581-587, the teachings of which are incorporated herein) may also be used to deliver one or more virus particle inhibitory compounds of the invention for treatment. Additional suitable delivery systems can include time-release, delayed release or sustained-release delivery systems. Such systems can avoid repeated administrations of a virus particle inhibitory compound, increasing convenience to the subject and the physician. Many types of release delivery systems are available and known to those of ordinary skill in the art. (See for example: U.S. Pat. Nos. 5,075,109; 4,452,775; 4,675,189; 5,736,152; 3,854,480; 5,133,974; and 5,407,686 (the teaching of each of which is incorporated herein by reference). In addition, pump-based hardware delivery systems can be used, some of which are adapted for implantation.

Use of a long-term sustained release implant may be particularly suitable for prophylactic treatment of subjects and for subjects at risk of developing a virus. Long-term release, as used herein, means that the implant is constructed and arranged to deliver therapeutic levels of the active ingredient for at least 30 days, 60 days, 90 days or longer. Long-term sustained release implants are well-known to those of ordinary skill in the art and include some of the release systems described above.

Therapeutic formulations of one or more virus particle inhibitory compounds of the invention may be prepared for storage by mixing the virus particle inhibitory compound having the desired degree of purity with optional pharmaceutically acceptable carriers, excipients or stabilizers [Remington's Pharmaceutical Sciences 21$^{st}$ edition, (2006)], in the form of lyophilized formulations or aqueous solutions. Acceptable carriers, excipients, or stabilizers are nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN®, PLURONICS® or polyethylene glycol (PEG).

Efficacy Determination and Assays

Certain aspects of the invention include methods to assess the efficacy of a virus particle inhibitory compound in treatment of a virus infection. Such methods may include comparing the effect on a cell or subject exposed to a virus (test cell and/or subject) and contacted with a virus particle inhibitory compound to the status of a substantially similar control cell or subject that is exposed to the virus but is not contacted with the virus particle inhibitory compound. A change in one or more of desirable effects such as, but not limited to: decreased virus particle infectivity, decreased viral infection, etc. in or of the contacted test cell or subject compared to the control cell or subject, respectively, indicates effectiveness of the virus particle inhibitory compound for treatment of the viral infection. In some embodiments of the invention, assay methods may include obtaining a biological sample from a subject or cell known to have been exposed to and/or infected by a virus, contacting the sample with a virus particle inhibitory compound and assessing the cell's response (e.g., level of virus particle infectivity, etc.). The test cell's response may be compared to a control cell. As used herein a biological sample may be an in vitro biological sample, or may a sample that is detected (e.g., obtained) in vivo. As used herein, a biological sample may be a cell sample, tissue sample, blood sample, bodily fluid sample, subcellular sample, etc. A biological sample may include cells, tissues, or organelles and may include cell types such as those described elsewhere herein.

Assays to assess a method of the invention to treat virus in a cell and/or subject may include but are not limited to (1) characterizing the efficacy of a virus particle inhibitory compound in treating a virus in a subject; (2) evaluating a combination treatment comprising administering one or more virus particle inhibitory compounds and administering one or more other anti-viral therapeutic treatments, (3) selecting a treatment for a virus based at least in part on the determined efficacy of the virus particle inhibitory compound alone or in combination; and (4) administering a virus particle inhibitory compound as at least a portion of a treatment of a virus in a subject. Thus, subjects can be characterized, treatment regimens can be monitored, treatments can be selected and diseases status can be better understood using embodiments of methods of the present invention.

The invention, in some aspects, includes various assays to determine the efficacy of a virus particle inhibitory compound administered to a cell and/or subject. Methods of the invention that are useful to determine virus particle inhibitory compound efficacy in cells, tissues, subjects, and samples (e.g., from subjects, in culture, etc.), include, but are not limited to: diagnostic assays to determine the presence of viral particles, the infectivity of viral particles, etc. Assessments of efficacy of a virus particle inhibitory compound to treat a viral infection can be done in vitro, for example in cell culture, cell samples, cell suspensions, etc. or can be done in vivo, for example in a living subject using art-known virus diagnostic assessments and tracking methods. Assessment of efficacy of candidate virus particle inhibitory compounds to treat a viral infection may also be done using assays of the invention in cells from culture—e.g., as screening assays to assess candidate virus particle inhibitory compounds ability to do one or more of: inhibiting virus particle infectivity, reducing an amount of a virus particle, reducing and/or preventing a viral infection, etc.

As will be appreciated by those of ordinary skill in the art, the evaluation of a treatment also may be based upon an evaluation of the symptoms or clinical end-points of a viral infection and such evaluations can be used in conjunction with methods of the invention to assess the status of a viral infection and/or the efficacy of a treatment of the invention for a viral infection.

Kits

Also within the scope of the invention are kits that comprise compounds, molecules, agents and/or pharmaceutical compositions of the invention and instructions for use. Kits of the invention may include one or more of a virus particle inhibitory compound, which may be used to treat a viral infection. Kits containing one or more virus particle inhibitory compounds or molecules or agents can be prepared for treatment methods of the invention. Components of kits of the invention may be packaged either in aqueous medium or in lyophilized form. A kit of the invention may comprise a carrier being compartmentalized to receive in close confinement therein one or more container means or series of container means such as test tubes, vials, flasks, bottles, syringes, or the like. A first container means or series of container means may contain one or more components such as one or more virus particle inhibitory compounds, one or more MCFD2 molecules, one or more MCFD2 mimetics, one or more ERGIC-53 molecules, one or more inhibitory agents of the invention, and may also include one or more labeling agents, and/or targeting agents, etc.

A kit of the invention may also include instructions. Instructions typically will be in written form and will provide guidance for carrying out the preparation of a virus particle inhibitory compound of the invention, and/or use of a virus particle inhibitory compound of the invention in a virus treatment or assay.

The following examples are provided to illustrate specific instances of the practice of the present invention and are not intended to limit the scope of the invention. As will be apparent to one of ordinary skill in the art, the present invention will find application in a variety of compositions and methods.

EXAMPLES

Example 1

Materials/Methods
Antibodies, Cells, Viruses and Plasmids

A number of antibodies were used in studies set forth herein. HA.11 Clone 16B12 mouse anti-HA (MMS-101P, Covance Emeryville, Calif.) (1:4,000) was used to detect recombinant viral glycoproteins in Western Blot assays. Mouse anti MCFD2 and rabbit anti ERGIC-53, used in microscopic examination of endogenous MCFD2 and ERGIC-53 by confocal and STORM applications respectively, as described in Klaus, J. P., et al, 2013 Cell Host & Microbe 14:522-534; Zhang, B. et al., 2003 Nature Genetics 34:220-225. 9B11 mouse anti-Myc (2276, Cell Signaling, Danvers, Mass.) (1:3000) was used to detect myc-MCFD2 in Western Blot assays. Calreticulin was used as a calcium-sensitive lectin prey-control in Western blots and was detected using rabbit anti (CRT) SPA-600 (Stressgen, Ann Arbor, Mich.) at 1:4,000. Mouse monoclonal anti JUNV GP-1 QC03-BF11 and NP NA05-AG12 (NR-2566 and NR-2582, BEI resources) were used to detect intracellular GP (confocal analysis) and C #1 particles (NP dSTORM analysis). Recombinant ERGIC-53 was detected in Western blots using clone M2 mouse anti-FLAG (1:3,000) (F1804, Sigma-Aldrich), and rabbit anti-ERGIC-53 antibody (sc-66880, Santa Cruz, Dallas, Tex.) (1:4,000) was used to detect endogenous ERGIC-53 in Western blot assays. For a thorough description of each viral GP used: JUNV XJ GP, JUNV C #1 GP, LASV GP, SARS S, ANDV GP, EBOV GP, MARV GP, FLUAV WSN33A HA, and VN HA, see the extended supplemental section of Klaus, J. P., et al, 2013 Cell Host & Microbe 14:522-534.

JUNV C #1, DANV, and recombinant VSVΔG have been previously described (Klaus, J. P., et al, 2013 Cell Host & Microbe 14:522-534). JUNV C #1 was provided by R. Tesh (The University of Texas Medical Branch at Galveston) and M. J. Buchmeier (University of California, Irvine) and DANV by W. I. Lipkin (Columbia University). VSVΔG engineered to express a Green Fluorescent Protein (GFP) in lieu of its own native G protein was provided by M. Whitt (The University of Tennessee Health Science Center, Memphis Tenn.).

All transfections were carried out using low-passage HEK293T/17 cells (CRL-11268, American Type Culture Collection, Manassas, Va.). HEK293T cells were maintained in Dulbecco's Modified Eagle Medium (DMEM) supplemented with 10% fetal bovine serum, 1% Penicillin-Streptomycin, 1% MEM Non-Essential Amino Acids solution, 1% GlutaMax, and buffered with 1% Hepes. All cell culture reagents were purchased from Invitrogen (Carlsbad, Calif.).

Vero cells were provided by J. Lindsay Whitton (The Scripps Research Institute, La Jolla, Calif.) were cultivated in DMEM supplemented with 10% FBS, 1% Penicillin-Streptomycin, and 1% Hepes. B-cells from either a healthy donor (MCFD2$^{+/+}$) (2829D) or from F5F8D patients with MCFD2 mutations CRC80 (c.149+5G>A (family A32)) and 1258 (c.103delC (family A21)) have been previously described (Zhang, B., et al., 2003 Nature genetics 34:220-225) and were cultured in RPMI 1640 containing 10% FBS, 1% Penicillin-Streptomycin, and 1% Hepes.

Transfections

All transfections were carried out with Polyethylenimine (PEI) (23966, Polysciences, Inc., Warrington, Pa.) using a ratio of 5 μL PEI (1 mg/mL stock brought up in PBS) to 1 μg plasmid DNA.

Affinity Purifications

To determine the molecular basis for arenavirus glycoproteins binding to ERGIC-53 and MCFD2 procedures were carried out to transfect into sub-confluent HEK293T/17 cells a pCAGGS expression plasmid previously described by Cornillez-Ty, C. et al. 2009 J. of Virology 83:10314-10318, into which JUNV C #1 GP [synthesized via Bio Basic Inc (Markhamm, ON)] was subcloned along with a plasmid encoding the bacterial biotin ligase BirA to ensure biotinylation of target GP molecules within cells. ERGIC-53 WT, ΔCRD, Δβ1, ΔHelix were as described previously (Zheng, C. et al., 2010 Blood 116: 5698-5706; Zheng, C. et al., 2010 Blood 115:1081-1087; and Klaus, J. P., et al, 2013 Cell Host & Microbe 14:522-534); FLAG-ERGIC-53 WT, ΔCRD, Δβ1, Δβ4, myc-MCFD2 WT, D89A, and D129E and have been previously described (Zhang, B. et al., 2008 Blood 111:5592-5600) and (Klaus J. P., et al., 2013 Cell host & microbe 14:522-534), and were co-transfected into cells with equal μg quantities. Following transfection, cultures were incubated for 48 hours at which point the cells were harvested as previously described (Klaus, J. P., et al, 2013 Cell Host & Microbe 14:522-534). Clarified lysates were incubated with streptavidin-coated magnetic beads (Dynabeads MyOne Streptavidin T1, 65602, Invitrogen) at 4° C. on a rotating platform for 2.5 hr to allow binding of biotinylated bait-prey protein complexes. The bead fractions were extensively washed with cold lysis buffer to remove unbound proteins, and proteins were eluted via boiling in Laemmli buffer supplemented with fresh β-mercaptoethanol to 5%. Captured proteins were then analyzed by SDS PAGE on Novex Tris-Glycine 4-20% precast gels (Invitrogen) and Western blot by probing for the different bait-prey combinations.

Co-immunoprecipitations in which exogenously added sMCFD2 was used as bait to examine its potential for binding ERGIC-53 released from cells, were carried out by first collecting supernatant from JUNV C #1- or mock-infected HEK cells cultured in Pro293 (protein free) medium (Lonza), and clarifying the supernatant of cellular debris by two centrifugation steps each 15 minutes at 1500 rpm in a refrigerated centrifuge. Following clarification, samples were pre-cleared of immunoglobulin binding proteins by incubation with Protein G beads (Dynabeads Protein G beads, 1004D, Invitrogen). Purified sMCFD2 (10 μg) was added to each condition in a buffer containing PBS supplemented with 0.05% BSA, 2.5 mM calcium chloride, and a Complete Mini EDTA-Free Protease Inhibitor Cocktail tablet (04693159001 Roche Applied Science), buffered with 1% Hepes pH 7.2. The supernatants were incubated for 2.5 hr on a rotating platform in the cold. To immunoprecipitate sMCFD2-ERGIC-53 protein complexes, mouse anti-myc mAb was added to each sample, and incubated for an additional 2 hr. Following the antibody incubation, Protein G magnetic beads were added to each condition and incubated for an additional 2 hr. Following extensive washing with cold wash buffer to remove non-specific bound proteins, the sMCFD2 captured complexes were concentrated on a magnetic column and then eluted by boiling in Laemmeli buffer with 5% β-Me. Samples were then analyzed by SDS PAGE and Western blot for myc-MCFD2 (bait) and ERGIC-53 (prey).

SDS PAGE and Immunoblotting

SDS PAGE and Immunoblot analysis was performed as described by Klaus, J. P., et al, 2013 Cell Host & Microbe 14:522-534.

Production of sMCFD2

Purification of secreted human MCFD2 was accomplished by transfecting into a T-75 flask of sub-confluent HEKs, a modified pCAGGS plasmid encoding human MCFD2 containing a 6× His tag and MYC tag (sub-cloned from pcDNA3.1 MCFD2 as in Zhang et al., 2008 Blood 111:5592-5600). Cells were allowed to recover for 2 days and were then trypsinized and re-seeded into 2 T-150 flasks. After 1 day of recovery the medium was removed, cells were washed once with PBS, and then replenished with Pro293 medium (Lonza) and incubated for 2 days prior to harvesting. Following 2 centrifugation steps, to remove any cellular debris (6000 g for 15 min), 5× Qiagen start buffer was added to the collected production medium, containing the secreted MCFD2, to yield a final concentration of 1× Qiagen start buffer (50 mM Tris-HCl, pH 7.5, 300 mM NaCl, 20 mM imidazole, 10% glycerol and 0.05% sodium azide). The His tagged sMCFD2 was then captured by passage over a Qiagen Ni-NTA column (8 mL of resin, 2 mL/min). The column was attached to a BioCad Sprint system (Applied Biosystems) allowing for continuous monitoring of the absorbance at 280 nm, the conductivity, and the pH. Following sample loading, the column was washed with start buffer until the baseline returned to the background level (<0.1 $A_{280}$ units). The sMCFD2 was eluted with start buffer containing 250 mM imidazole and 3 mL fractions were collected. The absorbance of each fraction at 280 nm was determined on a Cary 100 spectrophotometer. Fractions were screened via Western blot to identify samples containing myc-MCFD2 which were subsequently pooled. Pooled fractions were then concentrated using 10 kDa MWCO Ultracel microconcentrators to a concentration of 1 mg/mL, stored in Hepes-buffered PBS supplemented with 1 mM calcium chloride, and stored at 4° until use.

Protein concentrations were determined using the measured values for absorbance of protein at 280 nm wavelength and the extinction coefficient for the protein calculated via Epasy tools//web.expasy.org/protparam/. The molar extinction coefficient for MCFD2 was calculated by importing the amino acid sequence into the Expasy tool at: //web.expasy-.org/protparam/. The molar extinction coefficient was divided by the molecular weight to calculate absorbance coefficient. The protein absorbance reading at 280 nm was then divided by the absorbance coefficient (molar ext co./protein MW) to determine mg/mL of purified protein.

Microscopy 2-color confocal microscopy analysis was completed as described in Klaus, J. P., et al, 2013 Cell Host & Microbe 14:522-534. Briefly, for analysis of intracellular JUNV C #1 GP and MCFD2, HEK293T cells were seeded onto 12 mm glass coverslips (Thermo Scientific), and infected the following day with JUNV C #1 at a multiplicity of infection of 0.1. At 72 hours post-infection, cells were washed with PBS, and fixed using 4% paraformaldehyde (PFA) for 30 minutes at room temperature followed by extensive washing with PBS to remove excess PFA. Cells were permeabilized in a buffer containing 0.1% Triton-X 100 and 0.1% bovine serum albumin (BSA). A blocking step was carried out for 30 minutes at room temperature in a buffer containing 1% BSA and 10% normal goat serum (NGS). Mouse anti MCFD2 mAb was used at a dilution of 1:2000, incubated overnight at 4°, and then counter stained with Alexa Fluor 647-conjugated goat anti-mouse IgG (H+L) (A-21236, Invitrogen) at a dilution of 1:800. JUNV GP was stained using mouse monoclonal anti JUNV GP-1 QC03-BF11 directly conjugated to Alexa Fluor 488 (Invitrogen) at a dilution of 1:50. Nuclei were visualized via 4', 6-diamidino-2-phenylindole hydrochloride (DAPI) (D9542, Sigma Aldrich) staining, and slides were mounted using ProLong Gold Antifade Reagent (P36934, Invitrogen). Cells were imaged using a Zeiss LSM 510 Laser Scanning Confocal Microscope housed in the UVM microscopy imaging center. Images were acquired using a 63× lens with a numerical aperature of 1.4 with the optical zoom set to 1.5×. Using the AIM software suite images were captured at 1 airy unit, with gain settings for 488 and 647 signals balanced based on either mock infected controls (GP-488) or secondary only controls (MCFD2-647).

For visualizing JUNV C #1 virions containing three fluorophores using 2-dimensional (2D) and 3-dimensional (3D) direct stochastic optical reconstruction microscopy (2D and 3D 3dSTORM), clarified supernatant from JUNV C #1 (containing $1.0\times10^7$ PFU/mL virus), or mock infected cells was incubated for 2 hr at 37° in 35 mm glass bottom culture dishes (P356-1.5-10-C, MatTek Corporation, Ashland, Mass.) pretreated with 0.01% Poly-L-Lysine (3438-100-01, Trevigen, Gaithersburg, Md.). Following adsorption, the dishes were fixed using 4% PFA for 30 minutes at room temperature and then washed extensively to remove excess PFA. The virions were then permeabilized in a buffer containing 0.1% Triton-X100 with 0.1% BSA for 10 minutes at room temperature and washed 3× in buffer containing PBS with 0.1% BSA. A blocking step was carried out with PBS containing 1% BSA and 10% NGS for 30 minutes at room temperature.

Staining of virions was accomplished by first bathing the dishes with sMCFD2 (20 ng/μL) in buffer AB, containing PBS supplemented with 0.1% BSA and 1 mM $CaCl_2$, for 4 hours at 4° C. Dishes were then washed with buffer AB 3-times, before incubation with a mouse anti myc mAb, recognizing sMCFD2, at 1:50, and a rabbit polyclonal antibody recognizing ERGIC-53, at 1:50 for 2 hours at 4° C. The dishes were then washed 3-times in buffer AB, and counterstained with Alexa Fluor 647-conjugated goat anti-rabbit IgG (H+L) (Invitrogen) to reveal ERGIC-53 staining, and Alexa Fluor 568-conjugated goat anti-mouse IgG (H+L) (Invitrogen) to reveal sMCFD2, at 1:100, respectively for 2 hr 4° C. Following 3 additional washes in Buffer AB, JUNV NP staining was accomplished by incubating dishes with a biotin-conjugated mAb NA05-AG12 recognizing JUNV NP at a dilution of 1:50 for 2 hours at 4 degrees. Dishes were washed 3 additional times in buffer AB before NP was counter-stained with Alexa Fluor 488 conjugated streptavidin (Invitrogen) at a dilution of 1:100 in buffer AB for 2 hr at 4° C. Plates were then washed 3-times with PBS and stored at 4° C. prior to imaging.

A method was developed for the visualization of three fluorophores all using direct STORM (dSTORM) methodology. The Nikon n-STORM super-resolution microscope system consists of a Nikon Eclipse Ti-E TIRF inverted microscope base with laser modules delivering excitation at 405 nm, 488 nm, 561 nm, and 647 nm, and a high sensitivity Andor iXON3 DU897 EMCCD camera. Theoretically, this instrument provides resolution in the fluorescence mode of 20 nm lateral dimension and 50 nm axial dimension. For the triple dSTORM protocol, the following parameters were chosen: 100×, 1.45 NA objective lens; 64×64 pixel frame size; EM gain 10 MHz at 14 bit, EM gain multiplier 300, and 1× conversion gain; auto exposure 1 frame, and no binning. TIRF setting of illumination was determined to be 4100 using 647 nm laser excitation. Images were acquired using N-STORM "normal mode" setting with 0 activation cycles and 2 reporter cycles. A STORM quad cube (Nikon part #260319) was inserted into the microscope turret to separate the three fluorescence signals. Sequential order of activation was 488 nm (62 mWatts), followed by 647 nm (33 mWatts), and finally 561 nm (59 mWatts). Following acquisition of 15,000-30,000 frames, the data were rendered into a super-resolution image using a Gaussian distribution function. For three-dimensional image acquisition, an astigmatic lens was inserted into the microscope beam path. Image processing and display were accomplished with NIS Elements software.

All images were acquired in an oxygen scavenging buffer system containing glucose oxidase (G2133, Sigma) and catalase (C30, Sigma) in 50 mM Tris-HCl, with 10% glucose, and 0.1M cysteamine (30070, Sigma) that was prepared fresh prior to each imaging session.

Viral Challenge Assays

Viral challenge assays to assess the role of MCFD2 were conducted as described in Klaus, J. P., et al, 2013 Cell Host & Microbe 14:522-534. Briefly, to assess the consequences of plasmid over expression of MCFD2 (FIG. 1), HEK293T cells were seeded in 24 well plates (Fisher) and allowed to adhere for 24 hr at which time they were transfected with a plasmid encoding WT MCFD2, or with an empty plasmid, and incubated overnight. The following day monolayers were infected with JUNV C #1 at a multiplicity of infection of 0.1, or with DANV at a multiplicity of infection of 0.001, and the viruses were allowed to adsorb for 1 hour at 37° C. Following viral adsorption, monolayers were washed extensively with maintenance medium and returned to the incubator. At 48 and 72 hours post-infection, the supernatant was harvested, clarified by centrifugation for 5 minutes at 1500 rpm, transferred to a fresh Eppendorf tube, and stored for determination of PFU by standard plaque assay on Vero E6 cells. Results were tested for statistical significance using the Student's unpaired t-test where p values$<0.05$ were considered significant.

Viral challenge assays to determine the respective contributions of ERGIC-53's CRD features were carried out as described above herein with minor modifications. Combinations of plasmids that were transfected were balanced with an equal concentration of an empty vector where indicated (FIG. 3).

Viral challenge assays to assess the ability of EBV-transformed B cells from a healthy donor (2829D) or 2 MCFD2 null F5F8D patients (CRC-79 and 1258) to produce infectious arenavirus were conducted by infecting equal numbers of cells with JUNV C #1 in a low volume at a multiplicity of infection of 1. Viral adsorption was carried out at 37° C. for 2 hours at which time the cells were gently pelleted and inoculums were removed. The cells were then washed 3-times with PBS with each wash being followed by a low speed centrifugation step (1200 rpm for 5 minutes). Infected cells were then plated in a 24 well culture dish in complete RPMI medium, and returned to the incubator. After 72 hours the post infection supernatants were harvested via centrifugation (1200 rpm for minutes), and the clarified supernatants stored at −80° C. until determination of PFU content by standard plaque assay on Vero E6 cells.
Results
MCFD2 is a Negative Regulator of Arenavirus Propagation Studies were performed to examine the role of the macromolecular cargo receptor complex formed between ERGIC-53 and MCFD2. Experiments were designed to examine whether by increasing MCFD2 expression levels, an enhancement in viral propagation, similar to one observed following ERGIC-53 overexpression, would occur. WT MCFD2 was transiently overexpressed in HEK293T cells, and the impact of its expression was tested on a representative New and Old world arenavirus [Junin virus Candid1 (C #1) and Dandenong virus (DANV)]. In striking contrast to the effect of overexpressed ERGIC-53, increased expression of MCFD2 led to a potent decrease in the generation of infectious C #1 at 48 and 72 hours post infection (75.22% p=0.001 and 48.7% reduction p=0.0116, respectively) as well as DANV at 48 hpi (83.7% reduction p=0.0001). The results indicate a conserved and restrictive effect in both Old and New World arenavirus propagation (FIG. 1C-D). Results indicated that MCFD2 and ERGIC-53 have a divergent contribution to arenavirus propagation.
JUNV C #1 Propagation is Enhanced in Cells from F5F8D Patients who are MCFD2 Null Given the divergent influence of MCFD2 overexpression in arenavirus propagation compared to ERGIC-53's, experiments were performed to examine the effect on arenavirus replication in B cells derived from two unrelated F5F8D patients who had WT ERGIC-53, but were null for MCFD2 (1258 and CRC80—family A21 and A32 (Zhang, B., et al., 2003 Nature genetics 34:220-225). A healthy MCFD2 WT (2829D) donor served as a necessary control. Cells from each donor were challenged with C #1 to determine whether loss of MCFD2 would affect the production of infectious virus. Surprisingly, loss of MFD2 in these cells resulted in an increase in the release of infectious virus at 72 hpi (141.2% and 988.3% increase CRC80 and 1258 p<0.0001 and p=0.049, respectively) (FIG. 1D), thereby adding support to the antiviral role of the molecule.
MCFD2 Forms a Tripartite Complex with ERGIC-53 and Viral Glycoproteins Using a biotin-streptavidin affinity purification technique (Cornillez-Ty, C. T., et al. 2009 Journal of Virology 83:10314-10318), experiments were performed to test whether MCFD2 would associate with an arenavirus glycoprotein, or if the viral GP by interacting with ERGIC-53, precluded its binding to MCFD2. For the study, HEK 293T cells were co-transfected with plasmids encoding the JUNV C #1 GP and the bacterial biotin ligase BirA to ensure in-situ biotinylation of the GP, along with either WT ERGIC-53, WT MCFD2, or CRD mutants of ERGIC-53 [ΔCRD (non GP binding) or Δβ1(non-MCFD2 binding)] and as an internal control ERGIC-53 ΔHelix, and/or mutants of MCFD2 (D89A and D129E) unable to bind ERGIC-53 (Zheng, C., et al. 2010 Blood 116:5698-5706) because of changes in tertiary structure (Nishio, M. et al., 2010 PNAS USA 107:4034-4039), which are sufficient to cause F5F8D (Zhang, B., et al., 2003 Nature genetics 34:220-225). Biotinylated C #1 GP efficiently precipitated WT MCFD2 in the presence of WT ERGIC-53, but not ERGIC-53 Δβ1, which lacks the ability to bind MCFD2 (Zheng, C., et al. 2010 Blood 116:5698-5706) (FIG. 1F), suggesting that ERGIC-53 links MCFD2 to JUNV C #1 GP indirectly.

Figure 1B:
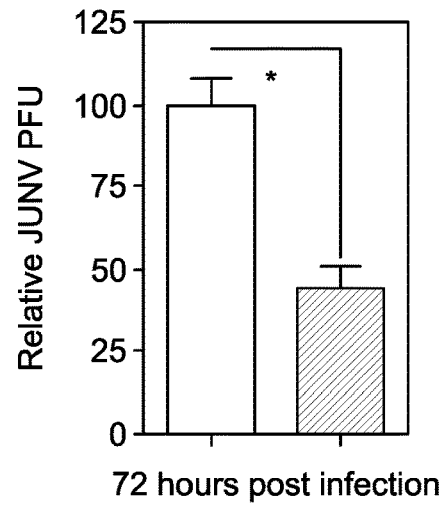
Figure 1C:
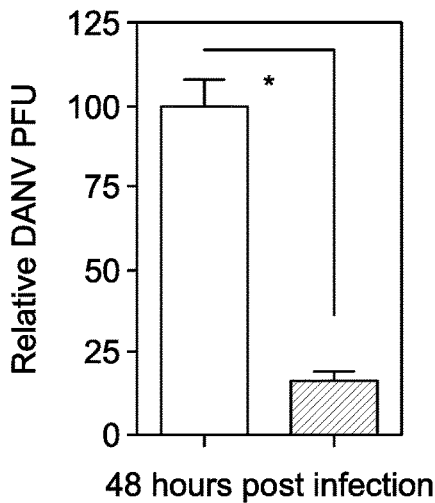
Figure 1D:
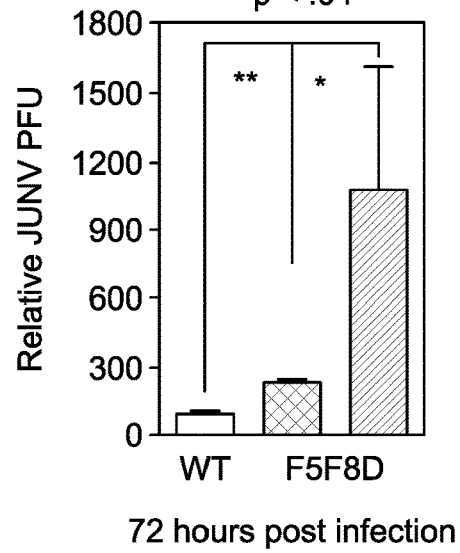
Figure 1E:
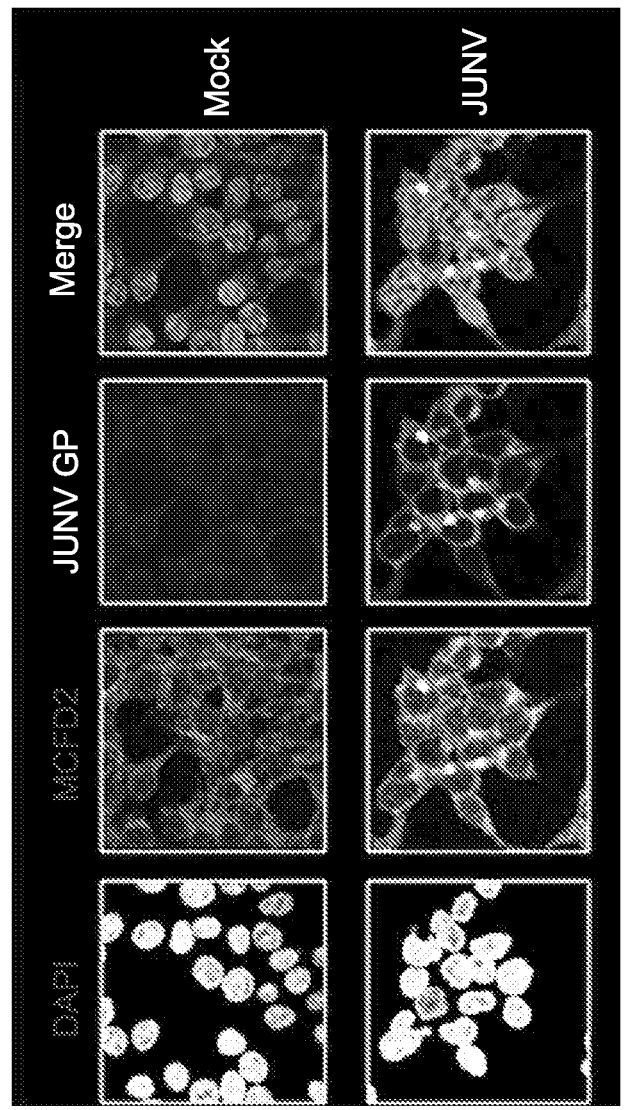
Figure 1F:
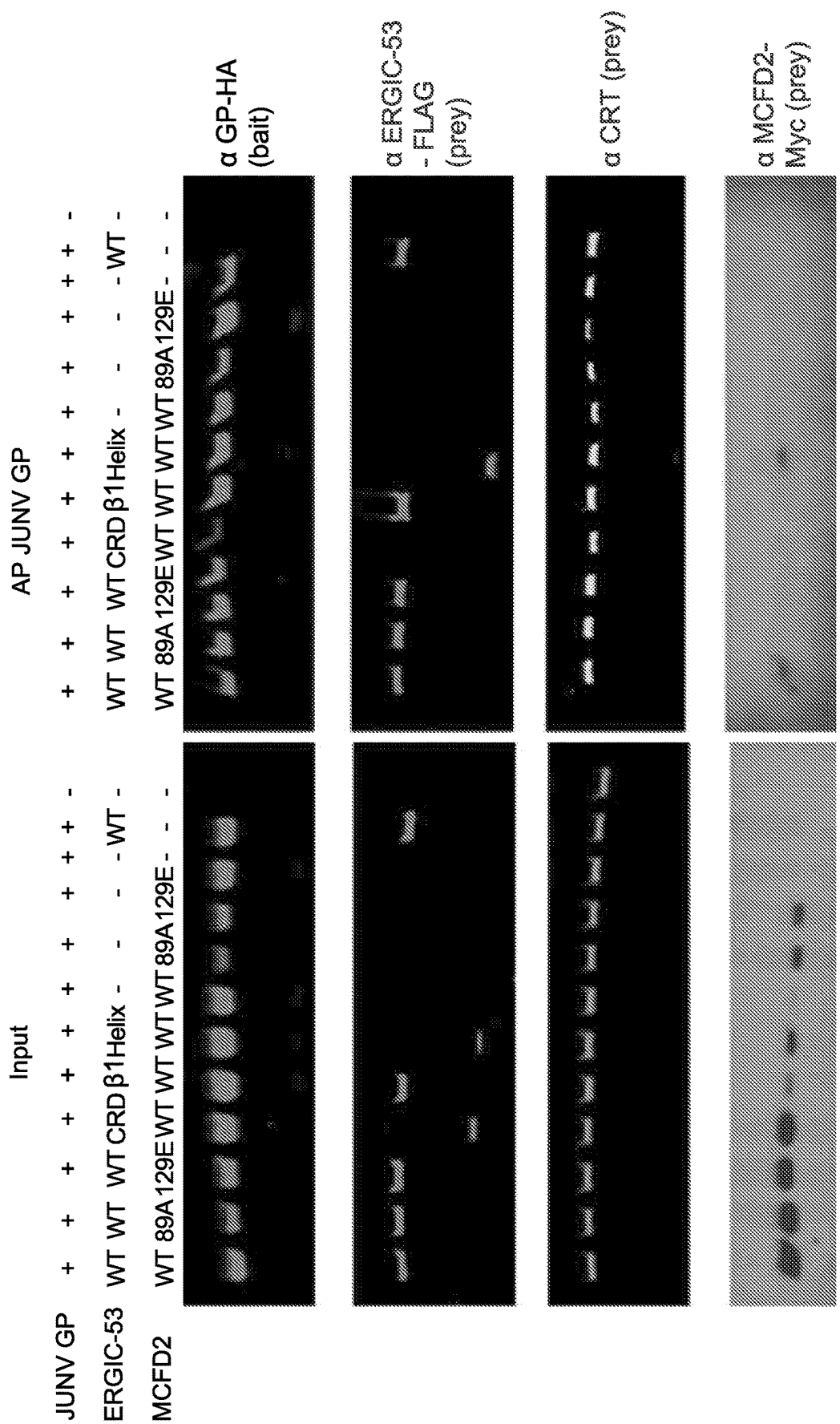
Figure 2A:
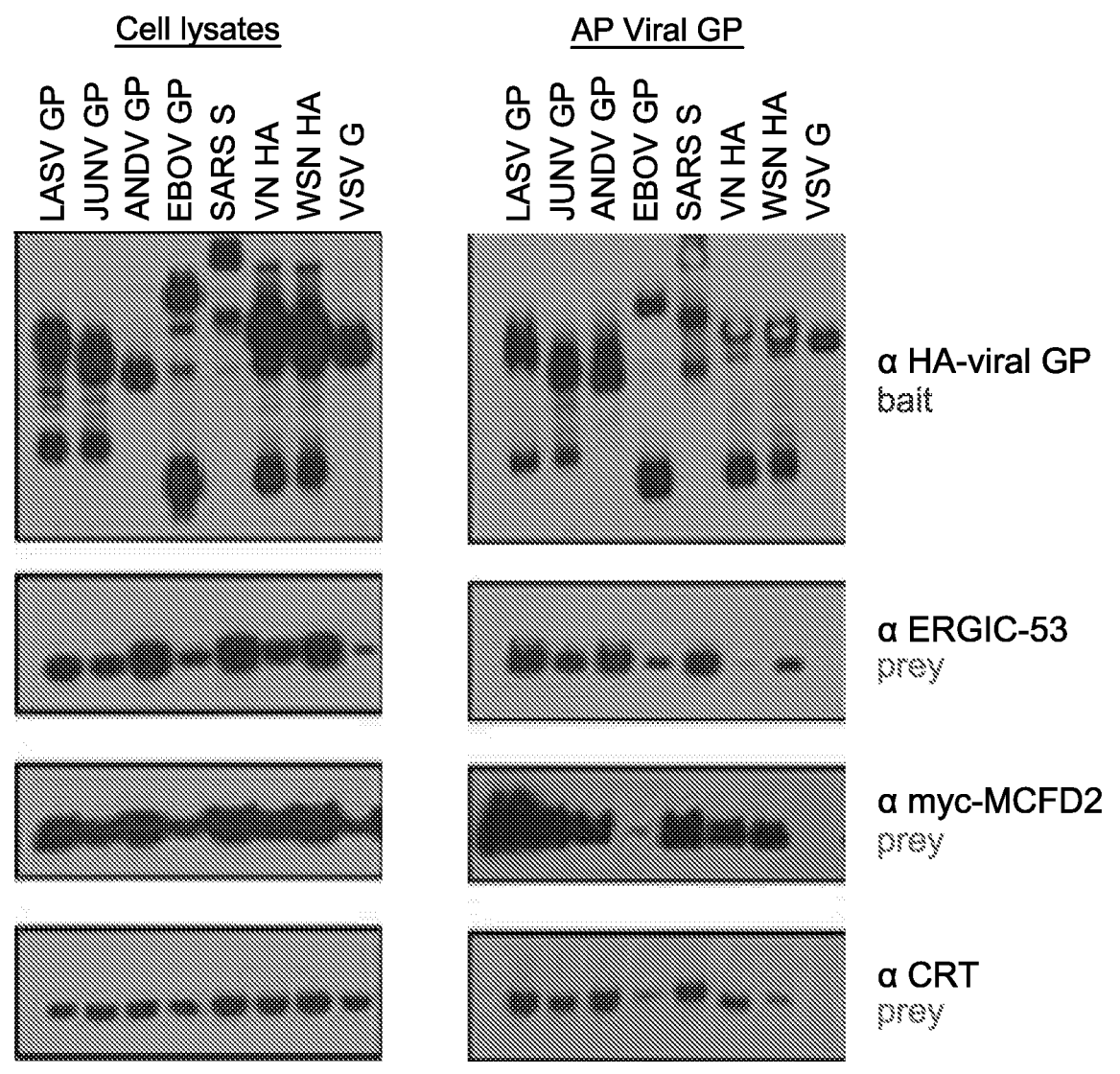
Figure 2B:
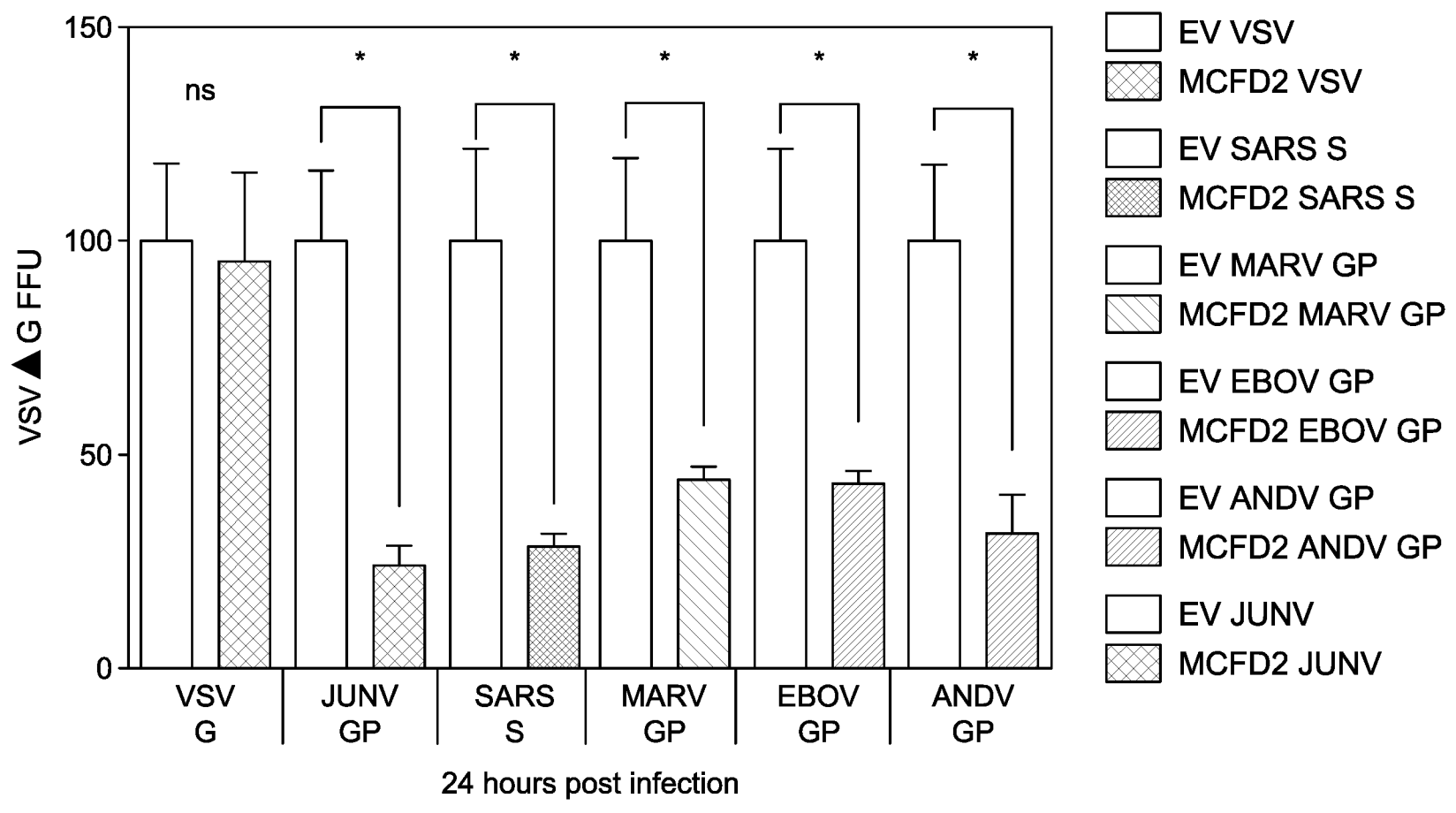

In validation of the requirement of ERGIC-53 to form the three-part complex, when ERGIC-53 ΔCRD (which is unable to interact with JUNV GP) was co-expressed in cells, WT MCFD2 did not precipitate with JUNV C #1 GP (FIG. 1F). MCFD2 binding was then restored following expression of ERGIC-53 ΔHelix, confirming the minimal requirement of an intact ERGIC CRD (aa 47-60) for the formation of the complex. Conversely, when JUNV GP precipitated WT ERGIC-53 in cells also expressing either of the two inactivating MCFD2 mutants (D89A and D129E), no MCFD2 was detected in the complex. This data indicates that MCFD2 forms an ERGIC-53 dependent complex with JUNV C #1 GP that minimally requires MCFD2 EF-hand residues D89 and D129 as well as ERGIC-53 CRD residues 47-60.
MCFD2 Trafficking During Infection with an Arenavirus To confirm the biochemical data suggesting a multi-protein complex between JUNV C #1 GP and MCFD2, and to visualize the intracellular distribution of these proteins, 2-color confocal microscopy analysis was performed on cells infected, or not, with JUNV C #1 72 hr post-infection (hpi). At 72 hpi, infected cells demonstrated a profound shift in the intracellular concentration and localization of MCFD2 compared to uninfected cells (FIG. 1F). The intracellular pool of MCFD2 was found to concentrate with JUNV GP, within the structure we have putatively identified as the ERGIC (FIG. 1F). Compared to the mock-infected control cells, a marked increase in MCFD2 was observed primarily within the ERGIC and punctate transport vesicles. This data demonstrates a virus-specific upregulation of MCFD2 expression and coordinated trafficking of MCFD2 to sites of GP concentration.
ERGIC-53/MCFD2 Receptor Complex has a Conserved Interaction with Viral GPs Given the broad extent of ERGIC-53's association with viral envelope glycoproteins, studies were performed to examine whether MCFD2 could also form a complex with additional envelope glycoproteins from arenaviruses [JUNV XJ and Lassa Virus (LASV) GP], hantaviruses (ANDV GP), as well as severe acute respiratory syndrome coronavirus (SARS CoV S), orthomyxoviruses [HA proteins from FLUAV WSN and VN (H1 & H5)], filoviruses (Ebola virus and Marburg virus (EBOV & MARV)), and finally a rhabdovirus envelope from vesicular stomatitis virus (VSV G) (FIG. 2A). All envelope glycoproteins tested, with the exception of VSV G, were found to complex with both ERGIC-53 and MCFD2 clearly showing that the ERGIC-53: MCFD2 molecular complex has a highly conserved but specific biochemical affinity for viral glycoproteins (FIG. 2A).
MCFD2's Antiviral Action is Highly Conserved and Restricted by the GP To assess the conservation of MCFD2's regulation of viral propagation, and to determine whether the molecular activity of MCFD2 can be restricted to the envelope glycoprotein: ERGIC-53 complex, experiments were performed that employed a vesicular stomatitis virus (VSV) pseudotyping approach whereby cells overexpressing MCFD2, or not, were transfected with plasmids encoding GPs representing a subset of those able to form a complex with ERGIC-53 and MCFD2 (FIG. 2A). Specifically, GPs from JUNV, SARS, ANDV, MARV, EBOV, and as a control VSV. Cells were infected a day later with pre-made VSV pseudoparticles (pp) of VSVΔG GFP+VSV G (Lawson, N. D., et al., 1995 PNAS 92:4477-4481). The resulting pseudotyped particles (VSVΔG+JUNV GP, SARS S, MARV GP, EBOV GP, or ANDV GP) generated from cells overexpressing MCFD2 (75.68% p=0.005; 71.01% p=0.0152; 55.26% p=0.0238; 56.61% p=0.0277; 68.18% p=0.0142 reduction, respectively), but not the empty control plasmid, were similarly restricted as with bona fide New and Old World arenavirus particles, whereas VSVΔG+VSV G was unaffected by MCFD2 (FIG. 2B). The pseudo-particle experiments indicate a highly conserved antiviral mechanism of action of MCFD2 across arenavirus, coronavirus, filovirus, and hantavirus particles that can be restricted to the presence of their respective envelope glycoproteins.

MCFD2 Controls ERGIC-53 Function in Arenavirus Propagation

Because MCFD2 associates with arenavirus GPs in an ERGIC-53 dependent fashion (FIG. 1F), and ERGIC-53 interacts with the arenavirus GP via its carbohydrate recognition domain a series of challenge experiments were designed to tease apart the relative contributions of the molecular complex. Experiments were performed to assess the role of ERGIC-53's entire CRD, which contains 3 non-overlapping regions: the GP binding region (FIG. 1F), the MCFD2 binding site (Zheng, C., et al. 2010 Blood 116:5698-5706), and the sugar binding cleft (Zheng, C., et al., 2013. Journal of Biological Chemistry 288:20499-20509), in arenavirus propagation. Cells were transfected with either: (i) a plasmid in which the CRD has been entirely deleted (ΔCRD), or as a control, plasmids encoding either (ii) WT ERGIC-53 (known to enhance C #1 replication), (iii) WT MCFD2, (iv) or an empty plasmid. These cells were infected a day later with JUNV C #1. At 48 hpi, in cells making an ERGIC-53 which can no longer bind to GP, sugar, or MCFD2 (ΔCRD), there was a reduction in the amount of infectious virus produced (61.95% reduction p=0.0002) (FIG. 3A). Likewise, when MCFD2 was in excess, there was a net reduction in the release of infectious virus (FIGS. 1A-C, and FIG. 3A).

Experiments were also performed to test the individual contributions of ERGIC-53's binding partners (e.g. MCFD2 and carbohydrate) to the ERGIC-53 mechanism of action on arenavirus replication. Given the CRD requirement for binding to GP, MCFD2, and carbohydrates, an experiment was designed in which HEK293T cells that had been co-transfected with either an empty plasmid, or plasmids making WT ERGIC-53, ERGIC-53 Δβ1 (non-MCFD2 binding), ERGIC-53 Δβ4 (non-MCFD2 and non-sugar binding), or N156A (non-sugar binding), were infected in tandem with WT MCFD2 (to ensure the opportunity for the cargo receptor complex to form). Results demonstrated that expression of ERGIC-53 ΔCRD, which cannot bind to carbohydrate or MCFD2, diminished the replication of JUNV C #1 (FIG. 3A). ERGIC-53 lacking the ability to bind MCFD2 (Δβ1) was unable inhibit viral propagation (28.26% reduction, p=0.09 (ns)), or MCFD2 and carbohydrate binding capabilities (Δβ4) was less efficient at inhibiting viral propagation (61.96% reduction, p=0.0067), respectively. The results indicated that an MCFD2-dependent allosteric regulation of ERGIC-53's lectin activity could be contributing to diminished viral propagation. Finally, ERGIC-53 N156A, unable to bind carbohydrate, but able to bind MCFD2, was also able to diminish viral propagation (84.89% reduction, p=0.0012). Collectively these data suggested a potent negative regulatory role for MCFD2 in the propagation of arenaviruses that is exerting its effect via an association with ERGIC-53 (potentially by altering its lectin activities).

Secretory MCFD2 Can Interact with ERGIC-53 in the Extracellular Space

Figure 4A:
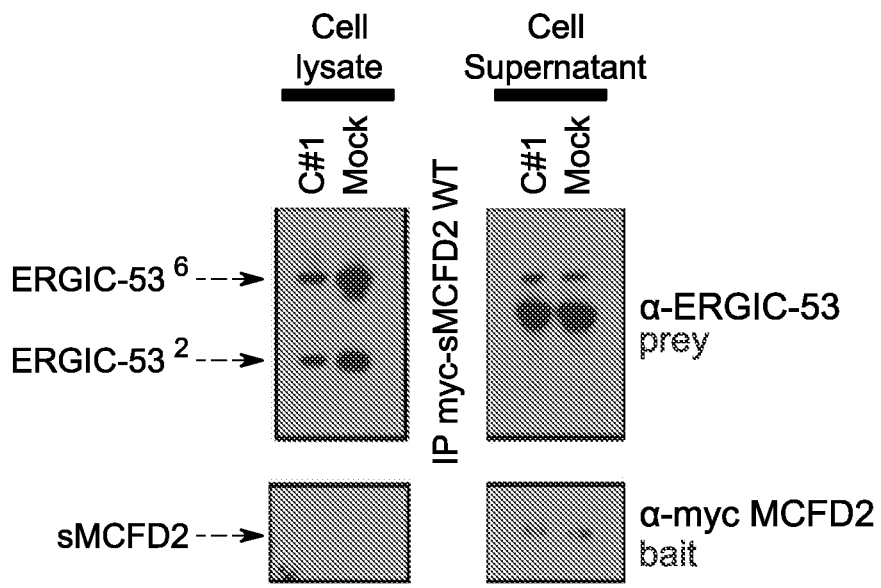
FIG. 4A-D provides blots, graphs, and photomicroscopy images of results demonstrating that sMCFD2 interacts with extracellular ERGIC-53 and arenaviruses to inhibit infectivity.

Experiments were performed to determine whether the binding of MCFD2 to secreted ERGIC-53 could be utilized to alter the entry of an arenavirus. These studies were designed to more precisely establish the properties of an ERGIC-53-dependent antiviral mechanism of action by MCFD2 in arenavirus propagation. Specifically, experiments were performed to test if a purified recombinant MCFD2 secreted from HEK cells (FIG. 5A-B) would interact with ERGIC-53 in the extracellular space. The secreted form of MCFD2 (sMCFD2), in mammalian cells, is heavily O-glycosylated (Nyfeler, B., et al., 2006 Traffic 7:1473-1481). The purified protein identified in the current studies migrated at approximately 28 kDa, which was consistent with the multiple additions of O-linked glycans in accordance with previous reports. To test whether sMCFD2 was capable of directly binding to ERGIC-53 a co-immunoprecipitation (Co-IP) technique was utilized whereby sMCFD2 was used to co-purify ERGIC-53 secreted from JUNV C #1 infected or mock infected cells (virus and exosome or exosome only). Culture fluid from infected and mock infected cultures was sequentially incubated with soluble recombinant MCFD2 (sMCFD2), followed by an antibody recognizing the C-terminal Myc tag of recombinant protein, and Protein-G coated magnetic beads. Recombinant sMCFD2 was able to co-purify ERGIC-53 from the supernatant under both conditions, indicating that the complex was stable outside of the secretory pathway, and that the post-translational modification of MCFD2 (O-linked glycosylation) did not prevent the formation of the cargo receptor complex (FIG. 4A).

MCFD2 Neutralizes Arenavirus Particles

Having demonstrated that sMCFD2 could interact with ERGIC-53 released from cells, and knowing that ERGIC-53 affects the attachment and entry of arenaviruses, studies were performed to determine if sMCFD2 could exert an effect on arenavirus entry via its association with ERGIC-53. To test this, JUNV C #1 and/or DANV were pre-incubated with purified sMCFD2, or a vehicle control, to allow for the formation of protein complexes. Following addition of pre-complexed sMCFD2—virions to cells, experiments were performed to test for an impact on virus production at 72 (C #1) and 48 (DANV) hpi. In both cases there was a potent inhibitory effect on the production of infectious virus; JUNV C #1 (90.32% reduction, p=0.0223) and DANV (94.88% reduction, p=0.0038) (FIG. 4C-D).

To confirm whether sMCFD2 was capable of directly binding to an arenavirus a 2D and 3D, triple color, direct stochastic optical reconstruction microscopy (2D and 3D 3dSTORM) approach was utilized to visualize, at a sub-diffraction level, the spatial arrangement of purified sMCFD2 pre-complexed with arenavirus virions (C #1) adhered to Poly-L-Lysine-treated matTek dishes. The virions, visualized via nucleoprotein (NP) staining, revealed sMCFD2 arranged in clusters of 200-500 nm rings, along with ERGIC-53, that were surrounding the densely packed arenavirus NP core (FIG. 4C-D).

As shown in FIG. 1A-C, overexpression of WT MCFD2 resulted in impaired production of infectious JUNV C #1 and DANV. FIG. 1D illustrates that production of infectious JUNV C #1 was enhanced in MCFD2 null cells. FIG. 1E provides photographic images of MCFD2 expression and trafficking during infection with an arenavirus. FIG. 1F demonstrates that MCFD2 formed an ERGIC-53-dependent tripartite complex with JUNV C #1 GP that required MCFD2 EF-hand residues 89 and 129.

FIG. 2A-B illustrates that MCFD2 antiviral action is conserved across multiple pathogenic RNA viruses and is specific to the viral GP. FIG. 2A demonstrates that MCFD2 forms a tripartite complex with arenavirus, coronavirus, filovirus, hantavirus, and orthomyxovirus envelope glycoproteins. FIG. 2B provides results that showed that MCFD2 has a highly conserved antiviral function that can be restricted to the viral glycoprotein.

Figure 3B:
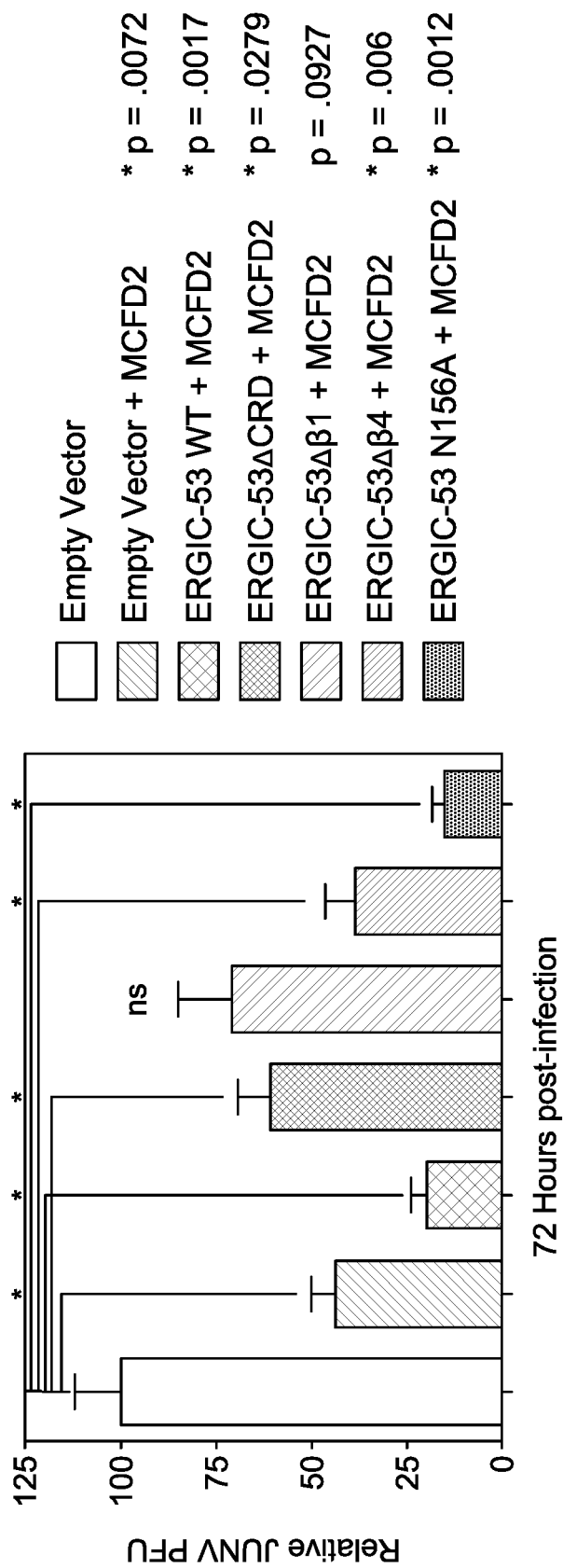

FIG. 3A-B illustrates that MCFD2 regulates ERGIC-53's lectin activity to inhibit arenavirus replication. FIG. 3A shows that ERGIC-53's CRD is critical for production of infectious JUNV C #1. FIG. 3B shows that interactions of ERGIC-53's CRD regulate arenavirus production.

Figure 4B:
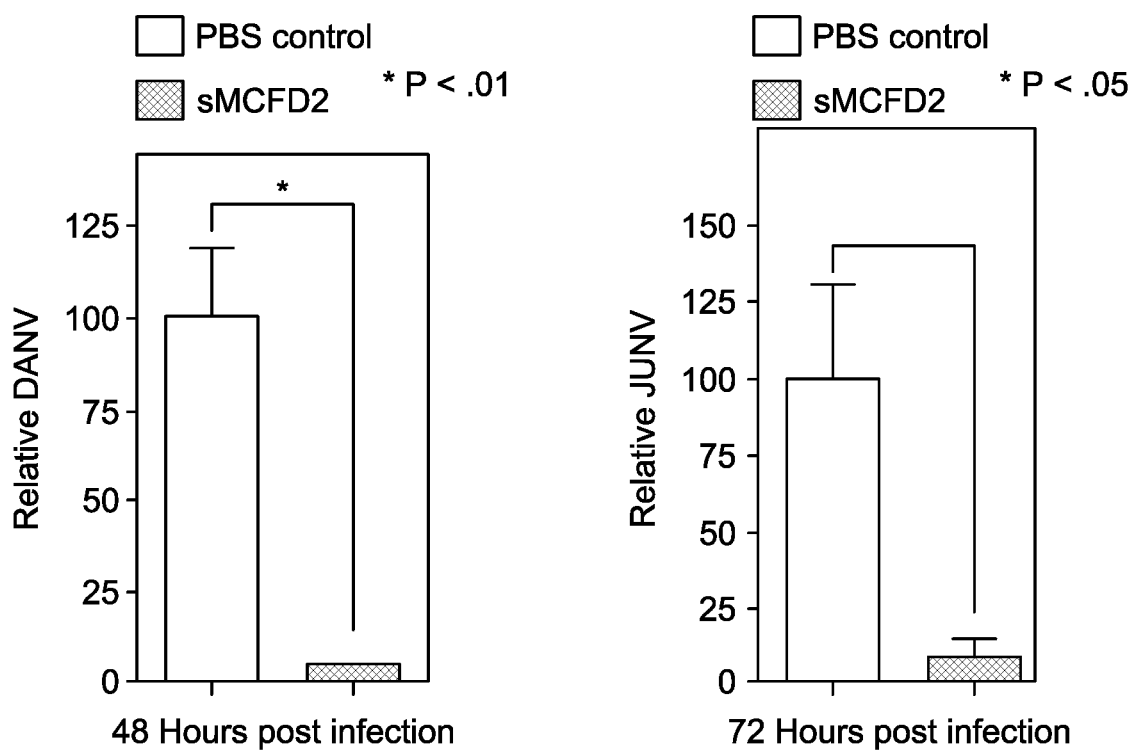
Figure 4C:
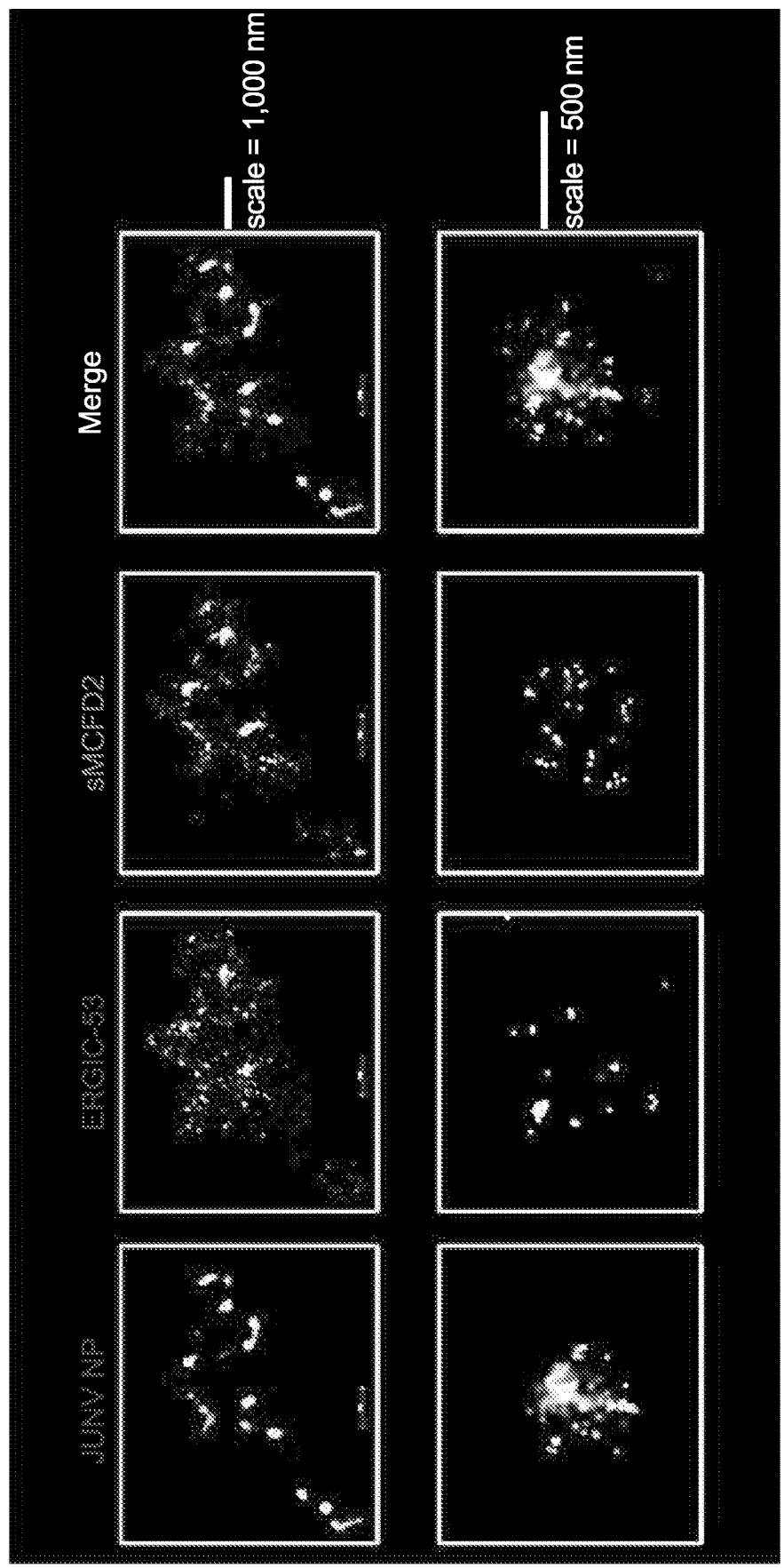
Figure 4D:
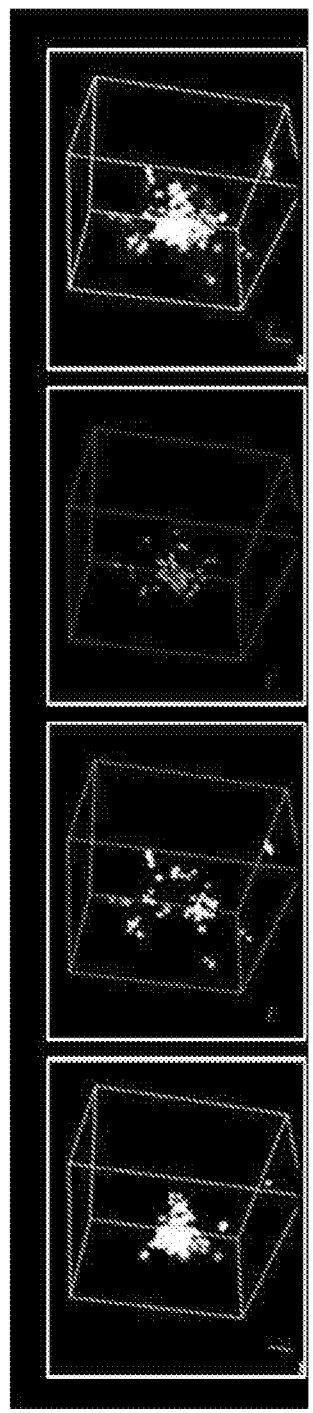

FIG. 4A-D shows that sMCFD2 interacts with extracellular ERGIC-53 and arenaviruses to inhibit infectivity. FIG. 4A shows that purified MCFD2 interacts with ERGIC-53 secreted from infected and mock infected cells. FIG. 4B illustrates that purified MCFD2 was able to inhibit the infectivity of Old and New World arenaviruses. FIG. 4C-D illustrates results from 2D and 3D 3dSTORM imaging, which revealed organization of sMCFD2 and ERGIC-53 on arenavirus particles. The two rows in FIG. 4C provide a 1,000 nm view of a series of JUNV C #1 particles, and then a single particle magnified. The image in FIG. 4D provides a 3D rendering of an individual JUNV C #1 virion identified via NP staining (green) containing a ring of ERGIC-53 (red) and MCFD2 (blue).

Figure 5:
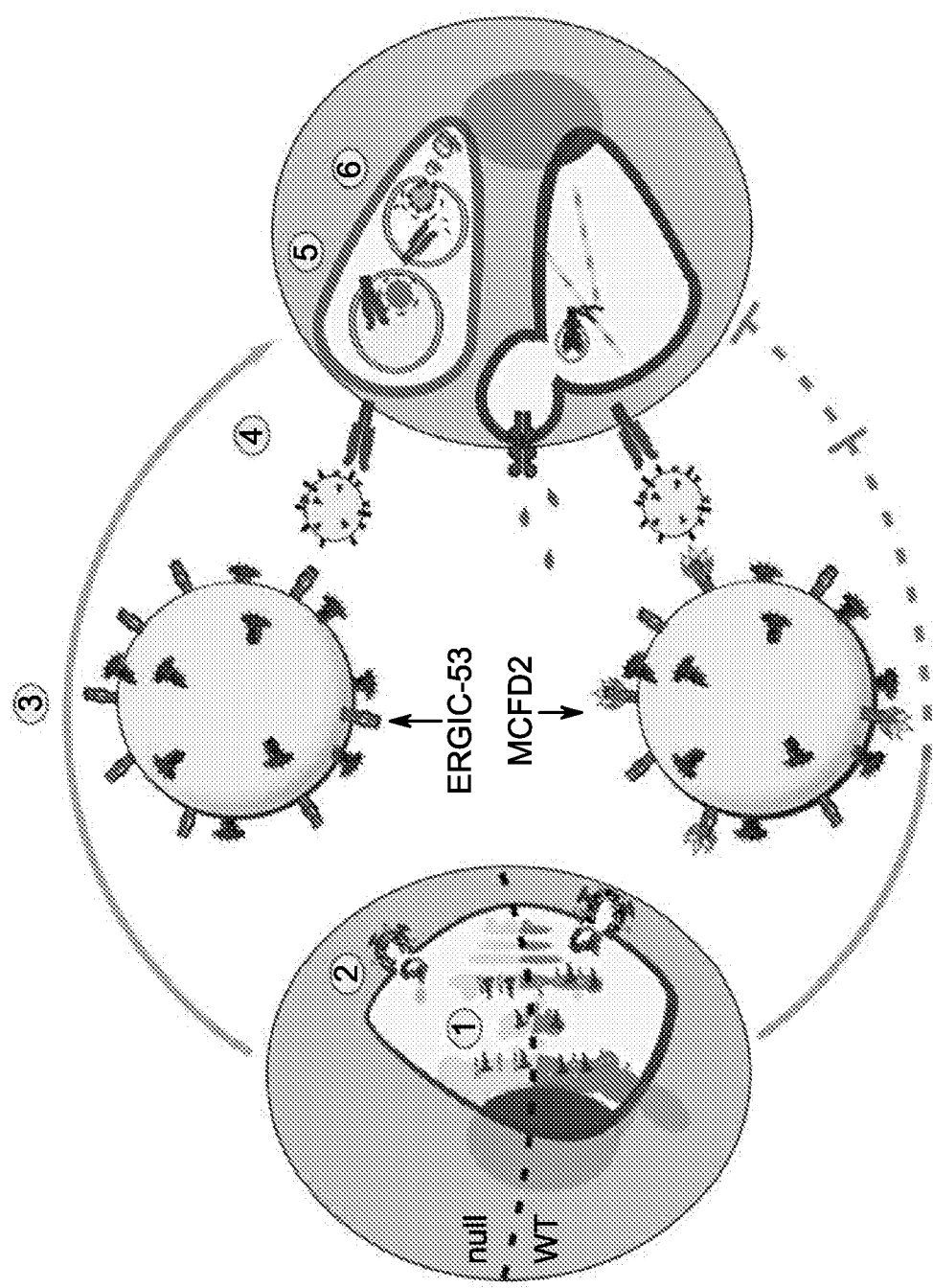
FIG. 5 is a schematic representation of the arenavirus lifecycle and specific stages where MCFD2 can exert an effect. Soluble MCFD2 (sMCFD2) interacts with extracellular ERGIC-53 and arenaviruses to inhibit infectivity. The bottom WT cell (shown below the dashed line in left-hand cell) represents a scenario where MCFD2 is present in abundance. The interaction between ERGIC-53/MCFD2 and GP is likely to occur early during synthesis in the ER/ERGIC (1) where the proteins are concentrated. Binding of MCFD2 to the complex may alter an intracellular maturation event leading up (folding, proteolysis, glycan maturation) to budding and release (2). MCFD2 interacts with ERGIC-53 in the context of viral particles (3) when added exogenously, and presumably during endogenous secretion, where it interferes with steps of arenavirus entry. MCFD2 binding may act at the level of receptor binding (4) either through blocking of arenavirus receptors, by changing ERGIC-53's sugar preference, or by ligation of an unknown MCFD2-specific receptor. If the entry defect is post-attachment, the targeting and trafficking (5), and fusion cascade (6) may also be disrupted.

Results indicated that soluble MCFD2 (sMCFD2) interacted with extracellular ERGIC-53 and arenaviruses to inhibit infectivity. FIG. 5 is a schematic representation of the arenavirus lifecycle that illustrates specific stages where MCFD2 can exert an effect. The oval elements at the left and right of the FIG. 5 are representative of null and WT cells. The cell shows activities of both null and WT, with the null activity illustrated above the dashed line around the diagramed cell center and the WT activity illustrated below the dashed line. In the image, the WT cell activity (shown below the dashed line in left-hand cell) represents a scenario where MCFD2 is present in abundance. The interaction between ERGIC-53/MCFD2 and GP is likely to occur early during synthesis in the ER/ERGIC (1) where the proteins are concentrated. Binding of MCFD2 to the complex may alter an intracellular maturation event leading up (folding, proteolysis, glycan maturation) to budding and release (2). MCFD2 interacts with ERGIC-53 in the context of viral particles (3) when added exogenously, and presumably during endogenous secretion, where it interferes with steps of arenavirus entry. MCFD2 binding may act at the level of receptor binding (4) either through blocking of arenavirus receptors, by changing ERGIC-53's sugar preference, or by ligation of an unknown MCFD2-specific receptor. If the entry defect is post-attachment, the targeting and trafficking (5), and fusion cascade (6) may also be disrupted.

Figure 6A:
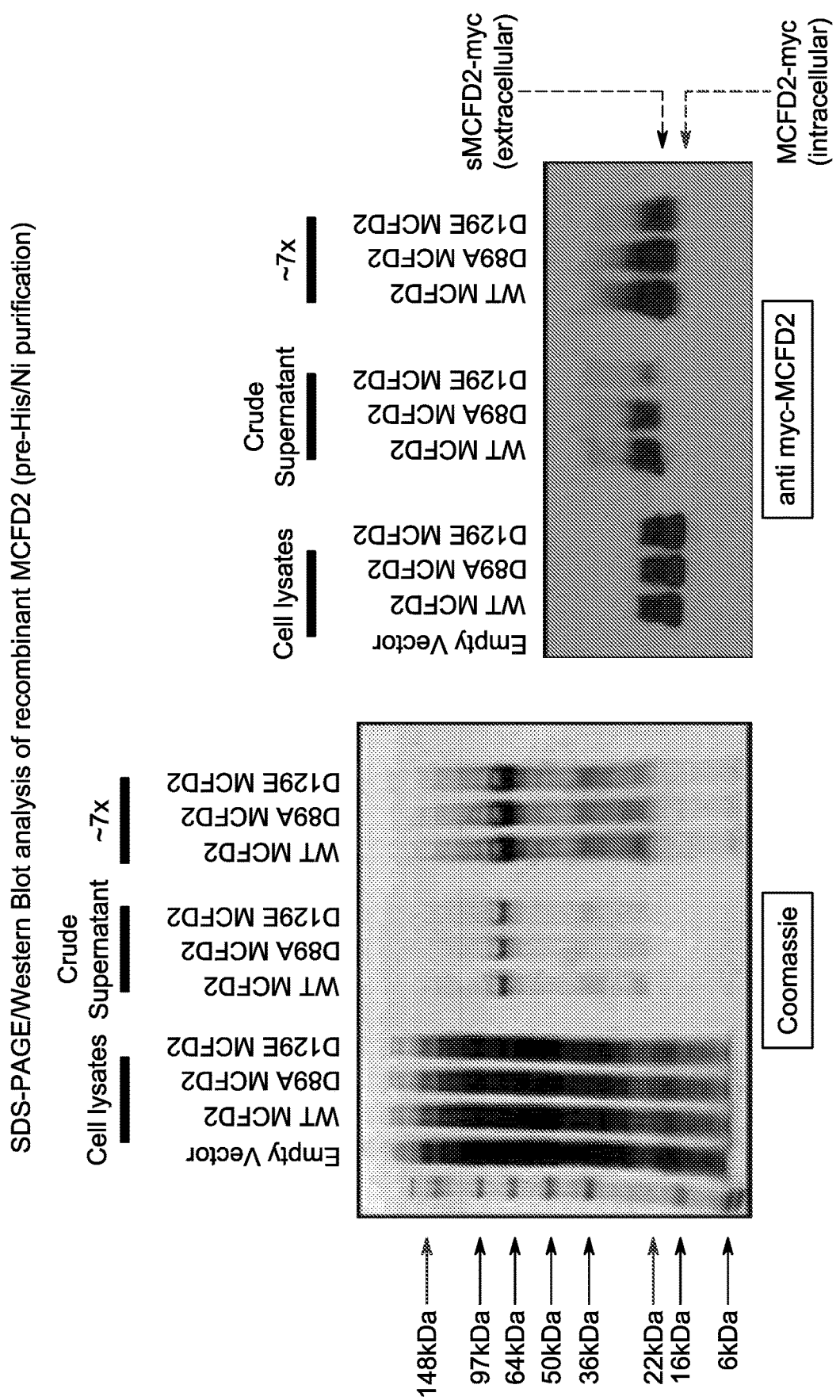
FIG. 6A-B provides blots and a graph of results from analysis of sMCFD2 production.
Figure 6B:
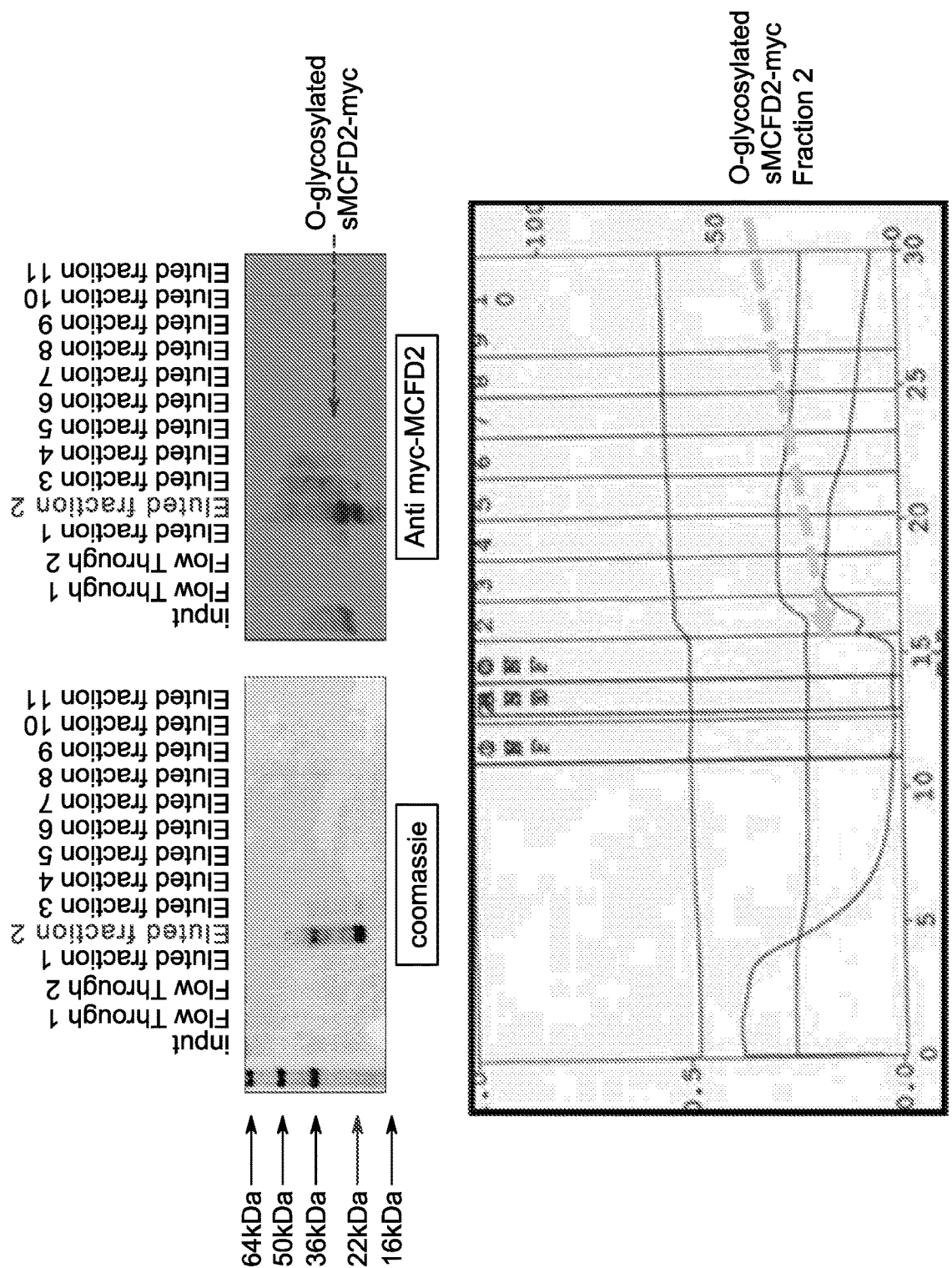

FIG. 6A-B illustrates results from analysis of sMCFD2 production. FIG. 6A provides results of SDS-PAGE/Western Blot analysis of recombinant MCFD2 (pre-His/Ni purification) and FIG. 6B provides results of SDS-PAGE/Western Blot analysis of recombinant MCFD2 (post-His/Ni purification).

Overall, experimental results indicated antiviral activity of MCFD2. This unexpected MCFD2 antiviral activity was demonstrated based on several lines of evidence. First, cells from MCFD2 null F5F8D patients were more adept at producing infectious JUNV (FIG. 1D), in contrast to previous studies on ERGIC-53 null cells (Klaus, J. et al. 2013 Cell Host & Microbe 14:522-534). Second, plasmid-driven overexpression of MCFD2 was able to inhibit the production of bonafide NW and OW arenavirus particles (FIG. 1A-C), and it was possible to restrict the impact of MCFD2 overexpression on viral propagation to the arenavirus GP independent of the remaining arenavirus core (FIG. 2A-B). VSV pseudoparticles bearing not only arenavirus, but also coronavirus, filovirus, and hantavirus GPs were likewise inhibited by the increased expression of MCFD2 in a GP specific manner which indicates a basic and highly conserved mechanism of action (FIG. 2A-B). Third, infection with an arenavirus greatly enhanced the expression of MCFD2, and concentrated it in the structure previously identified as the ERGIC (FIG. 1F) (Hauri, H. P. et al., 2000 J Cell Sci 113 (Pt 4):587-596). Lastly, exogenously supplied soluble MCFD2 was able to interact with individual arenavirus particles, visualized at sub-diffraction limited resolution, and precomplexed virus was deficient in its ability to successfully initiate a new round of propagation (FIG. 4A).

The binding of an arenavirus GP to a site within the CRD that is distinct from the sugar-binding region, preserves the lectin function of ERGIC-53, presumably to the benefit of the virus. Accordingly, when the CRD was removed from ERGIC-53 expressed in a viral challenge assay, a concomitant reduction in arenavirus propagation occurred (FIG. 3A). Likewise, when the ΔCRD, Δβ4, and N156A mutants were expressed in addition to MCFD2 overexpression, a dampening in the MCFD2-mediated regulation occurred (FIG. 3A-B), suggesting MCFD2 acts through the CRD to alter arenavirus propagation.

The experimental results provide support for a finding that ERGIC-53's lectin activity may be targeted via its cofactor MCFD2, as a therapeutic approach for treating arenavirus infections (FIG. 4A-C). Given the conservation of the MCFD2-dependent antiviral activity with not only arenaviruses, but also coronaviruses, filoviruses, and hantaviruses (FIG. 2A-B), the results indicate that the molecule may represent a valuable broad-spectrum antiviral target.

EQUIVALENTS

Although several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto; the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

All references, patents and patent applications and publications that are cited or referred to in this application are incorporated herein in their entirety herein by reference.

What is claimed is:

1. A method of reducing infectivity of a virus particle comprising an ERGIC-53 polypeptide, the method comprising:
    contacting the virus particle comprising the ERGIC-53 polypeptide with an MCFD2 polypeptide that does one or more of: specifically binds in and sterically blocks the coding region determinant (CRD) of the ERGIC-53 polypeptide sequence thereby reducing infectivity of the virus particle.

2. The method of claim 1, wherein the virus particle and the ERGIC-53 polypeptide are external to a cell and the binding in or sterically blocking the CRD of the ERGIC-53 polypeptide reduces one or more of the propagation of the virus particle, infectivity of the virus particle, and delivery of the virus particle into the cell.

3. The method of claim 1, wherein the virus particle is in a subject, wherein the subject is suspected of being or known to be infected with the virus particle, and reducing the infectivity of the virus particle treats the viral infection in the subject.

4. The method of claim 1, wherein the virus particle comprising the ERGIC-53 polypeptide is an arenavirus particle, a coronavirus particle, or a filovirus particle.

5. The method of claim 1, wherein the MCFD2 polypeptide is soluble MCFD2 polypeptide.

6. The method of claim 1, wherein the MCFD2 polypeptide is O-glycosylated.

7. The method of claim 1, wherein the MCFD2 polypeptide is a recombinant polypeptide.

8. The method of claim 1, wherein the virus particle comprising the ERGIC-53 polypeptide is inside of a cell and spans the cell membrane with the ERGIC-53-containing portion of the virus particle positioned external to the cell, and the binding in or sterically blocking the CRD of the ERGIC-53 polypeptide reduces one or more of the propagation of the virus particle, infectivity of the virus particle, and release of the virus particle from the cell.

9. The method of claim 1, wherein the virus particle comprising the ERGIC-53 polypeptide is internal to a cell, and the binding in or sterically blocking the CRD of the ERGIC-53 polypeptide reduces one or more of the propagation of the virus particle, infectivity of the virus particle, and release of the virus particle from the cell.

* * * * *